(12) United States Patent
Leonardi et al.

(10) Patent No.: US 8,580,962 B2
(45) Date of Patent: Nov. 12, 2013

(54) SPIROHETEROCYCLIC COMPOUNDS AS MGLU5 ANTAGONISTS

(75) Inventors: Amedeo Leonardi, Milan (IT); Gianni Motta, Barlassina (IT); Carlo Riva, Varese (IT); Luciano Guarneri, Garbagnate Milanese (IT); Davide Graziani, Milan (IT); Carlo De Toma, Milan (IT); Katia Dimitrova Karamfilova, Sesto San Giovanni (IT)

(73) Assignee: Recordati Ireland Ltd., Milan (IT)

( * ) Notice: Subject to any disclaimer, the term of this patent is extended or adjusted under 35 U.S.C. 154(b) by 198 days.

(21) Appl. No.: 13/180,166

(22) Filed: Jul. 11, 2011

(65) Prior Publication Data
US 2012/0059015 A1 Mar. 8, 2012

Related U.S. Application Data

(60) Provisional application No. 61/362,944, filed on Jul. 9, 2010.

(51) Int. Cl.
*A61K 31/44* (2006.01)
*C07D 213/00* (2006.01)

(52) U.S. Cl.
USPC ............................................. 546/15; 514/278

(58) Field of Classification Search
None
See application file for complete search history.

(56) References Cited

FOREIGN PATENT DOCUMENTS

| WO | 2005/030723 A1 | 4/2005 |
|---|---|---|
| WO | 2006/114260 A1 | 11/2006 |
| WO | 2008/032191 A2 | 3/2008 |

OTHER PUBLICATIONS

International Search Report for International Application No. PCT/EP2011/061690 mailed Sep. 16, 2011.

*Primary Examiner* — Janet Andres
*Assistant Examiner* — Heidi Reese
(74) *Attorney, Agent, or Firm* — Merchant & Gould P.C.

(57) ABSTRACT

The invention is directed to methods of using antagonists selective for the metabotropic mGlu5 receptor to treat conditions of neuromuscular dysfunction of the lower urinary tract in a mammal. Provided are methods of treating a mammal suffering from a condition of neuromuscular dysfunction of the lower urinary tract by administering a selective mGlu5 antagonist. The selective mGlu5 antagonist may be administered alone or in combination with one or more additional therapeutic agents for treating such a condition. Also provided are methods of identifying selective mGlu5 antagonists that are useful for treating neuromuscular dysfunction of the lower urinary tract in a mammal. Methods for treating migraine and gastroesophageal reflux disease (GERD) using selective mGlu5 antagonists are also disclosed.

16 Claims, No Drawings

SPIROHETEROCYCLIC COMPOUNDS AS MGLU5 ANTAGONISTS

This application claims benefit of U.S. Ser. No. 61/362,944, filed 9 Jul. 2010 and which application is incorporated herein by reference. To the extent appropriate, a claim of priority is made to the above disclosed application.

FIELD OF THE INVENTION

This invention relates to novel spiroheterocyclic compounds having selective affinity for the mGlu5 subtype, of metabotropic receptors, to pharmaceutical compositions comprising such compounds, and to methods of treatment therewith.

BACKGROUND OF THE INVENTION

Lower urinary tract disorders encompass an assortment of syndromes that affect normal micturition. Lower urinary tract disorders may develop through combination of pathological and/or age-related changes of the urogenital system, or other etiology, e.g., neurological disorders. Individuals suffering from lower urinary tract disorders suffer from impaired quality of life, including embarrassment, poor self-perception, and a general reduction in emotional well-being, social function, and general health. Lower urinary tract disorders, moreover, may be associated with other physical ailments, including cellulitis, pressure ulcers, urinary tract infections, falls with fractures, sleep deprivation, social withdrawal, depression, and sexual dysfunction. Older individuals suffering from lower urinary tract disorders may require more care from health care providers, both family and professional, which may be a factor in decisions to place them in institutions.

According to the U.S. National Institutes of Health (NIH), up to 35 million Americans are estimated to suffer from lower urinary tract disorders. Lower urinary tract disorders are more common among women than men (2:1) until age 80, after which men and women are equally affected. The prevalence of lower urinary tract disorders increases with age. By the age 65, lower urinary tract disorders affect 15% to 30% of all individuals and approximately 50% of individuals in long-term care.

Agents with various modes of action have been used to treat lower urinary tract disorders. These include agents that act directly on the lower urinary tract, e.g., antimuscarinics and alpha-1 antagonists, and agents that act through the central nervous system, e.g., serotonin and/or noradrenaline reuptake inhibitors. According to the NIH, however, while some progress has been made in the diagnosis, management, and treatment of lower urinary tract disorders, these disorders frequently remain intractable. Thus, there is a continued need for improved agents, formulations and therapies to treat lower urinary tract disorders.

Glutamic acid, an excitatory amino acid, is present at synapses throughout the central nervous system and is known to act on at least two types of receptors: ionotropic and metabotropic glutamate receptors. The principle function of ionotropic glutamate receptors is that their activation forms ligand-gated ion channels and, thereby, they directly mediate electrical signaling of nerve cells, producing rapid and relatively large conductance changes in the post-synaptic membranes. Metabotropic glutamate receptors (mGluRs) regulate electrical signaling indirectly, by influencing intracellular metabolic processes via G-proteins. Changes in the post-synaptic cell that are mediated through mGluRs are consequently relatively slow over time and are not linked to rapid and large changes in neuronal membrane conductance.

Three subtypes of ionotropic glutamate receptors have been described, i.e., the NMDA, AMPA and kainate subtypes.

Eight subtypes of metabotropic glutamate receptors have been cloned. The subtypes are classified into three groups on the basis of sequence similarities, and pharmacological and biochemical properties (Spooren et al., *Trends Pharmacol. Sci.* 22: 331-337, 2001): Group I mGlu receptors (mGlu1 and mGlu5), Group II mGlu receptors (mGlu2 and mGlu3) and Group III mGlu receptors (mGlu4, mGlu6, mGlu7 and mGlu8).

Group I receptor mGlu5 (either human or rat) is known to comprise at least two subtypes, "a" and "b". Subtype "b" is longer than subtype "a", because of an alternative splicing of a 32-amino-acid stretch in the C-terminal (intracellular) domain, 50 residues downstream of the beginning of the domain. The human mGlu5b is 1212 amino acids long, while the "a" form lacks the amino acids from 877 to 908 (n. 828 being the first of the intracellular domain). The rat mGlu5b is 1203 amino acids long, while the "a" form lacks the amino acids from 876 to 907 (n. 827 being the first of the intracellular domain). (Hermans and Challis, *Biochem. J.* 359: 465-484, 2001).

The mGlu receptors, belonging to family 3 of GPCRs, are characterized by two distinct topological domains: a large extracellular N-terminal domain containing a Venus fly-trap module responsible for agonist binding and the 7-TM domain plus intracellular C-terminal domain that is involved in receptor activation and G-protein coupling.

The 7-TMD of mGlu Group I receptors has been shown to form a binding pocket for positive and negative allosteric modulators; the negative ones have been identified thanks to high throughput screening technologies and act as non-competitive antagonists, having no effect on agonist binding. The most interesting property of these molecules, in addition to their high potency, is their remarkable subtype selectivity.

The 7-TM binding region is located in a pocket-lined by TM-III, TM-V, TM-VI and TM-VII; this site corresponds to the retinal binding pocket in rhodopsin.

Allosteric modulators of mGlu5 represent an exciting advance in demonstrating the potential for developing novel research tools and therapeutic agents that regulate activity of specific mGluR subtypes.

The compounds of the instant invention include those reported herein as mGlu5 antagonists, which in many cases are actually negative allosteric modulators acting at the 7-TM binding region.

WO 00/63166 discloses tricyclic carbamic acid derivatives useful for the treatment of different diseases, including urinary incontinence. The derivatives are disclosed to be agonists or antagonists of Group I mGlu receptors with specificity for the mGlu1 receptor.

WO 01/32632 discloses pyrimidine derivatives useful for the treatment of different diseases, including urinary incontinence. The derivatives are disclosed as selective antagonists of the mGlu1 receptor with at least 10-fold selectivity for the mGlu1 receptor over the mGlu 5 receptor.

WO 01/27070 discloses new bisarylacetamides useful for the treatment of urinary incontinence, among other conditions. The molecules are disclosed to be agonists or antagonists selective for the mGlu1 receptor.

U.S. Pat. No. 6,369,222 discloses heterocycloazepinyl pyrimidine derivatives useful for the treatment of urinary incontinence, among other conditions. The derivatives are disclosed to be antagonists of the mGlu1 receptor.

The aforementioned applications and patent, therefore, disclose mGlu1 receptor antagonists as useful for treating urinary incontinence. None of the references, however, provide experimental support for treatment of urinary incontinence, either in human patients or in an animal model for lower urinary tract disease.

We have tested the activity of selective mGlu1 and selective mGlu5 antagonists, in a rat model useful to detect activity on the lower urinary tract. Surprisingly, good activity was found for antagonists selective for the mGlu5 receptor, whereas two commercially available antagonists selective for mGlu1 receptor failed to exhibit an effect. An antagonist selective for Group II mGluR receptors also failed to exhibit an effect in the rat model. Given these results, selective mGlu5 antagonists can be an effective means to treat lower urinary tract disorders.

There is a need in the art to develop novel compounds and compositions for the treatment of lower urinary tract disorders and for the alleviation of the symptoms associated with such disorders. The present inventors have addressed this need through the development of novel heterocyclic compounds that are selective mGlu5 modulators, including selective mGlu5 antagonists. The compounds of the present invention provide potent inhibition of the micturition reflex through a novel mechanism of action.

SUMMARY OF THE INVENTION

The invention is based on the finding that selective mGlu5 modulators, including, selective mGlu5 antagonist compounds are useful in the treatment of lower urinary tract disorders, such as neuromuscular dysfunction of the lower urinary tract, and in the treatment of migraine and in gastroesophageal reflux disease (GERD) in mammals. mGlu5 modulator compounds are also useful in the treatment of anxiety disorder in mammals, and in the treatment of substance abuse, substance dependence and substance withdrawal disorders in mammals. Another use of mGlu5 modulator compounds is related to the treatment of fragile X syndrome disorders.

In one embodiment, the selective mGlu5 modulator compounds of the present invention are the novel compounds represented by Formula I, which are preferably selective mGlu5 antagonists.

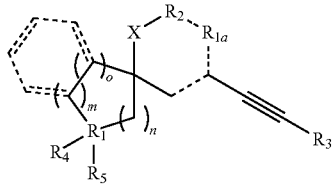

I wherein:
X is oxygen or sulfur;
$R_1$ is carbon, nitrogen, oxygen or sulfur;
$R_{1a}$ is CH, $CH_2$, N, or NH;
$R_2$ is a bond, a CH group or a $CH_2$ group;
$R_3$ is an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group;

$R_4$ is absent is hydrogen, or is an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, an optionally substituted alkyl group, hydroxy, alkoxy, thiol, thioalkyl, amino, N-alkylamino, or N,N-dialkylamino or a halogen atom;

$R_5$ is absent is hydrogen, hydroxyl, thiol, amino, or is optionally substituted alkyl, alkoxy, thioalkyl, alkylamino, dialkylamino, cyano, aminocarbonyl, alkylaminocarbonyl, arylcarbonyl, dialkylaminocarbonyl, N-alkoxy-N-alkylaminocarbonyl, alkoxycarbonyl, aryloxycarbonyl, heteroaryloxycarbonyl, heterocyclylcarbonyl, heteroarylcarbonyl, or heterocyclylaminocarbonyl, or a halogen atom; or when $R_1$ is a carbon atom, R4 and R5 are joined together to form an optionally substituted methylene group, a keto group, an oxime each one optionally substituted with alkyl, cycloalkyl, halogen or a heterocyclic group; or when $R_1$ is a carbon atom, $R_4$ and $R_5$ are each carbon, oxygen, nitrogen, or sulfur linked to each other through an optionally substituted $C_1$-$C_3$ alkylene group;
m is 1-2;
n is 1-2;
o is 0-1; and
---- is a single or double bond;

is an optionally substituted phenyl group which is optionally present when m is 1, n is 1-2, and o is 1; and enantiomers, diastereomers, and N-oxides thereof; and pharmaceutically acceptable salts thereof.

In a more preferred embodiment, the novel compounds are represented by Formula Ia

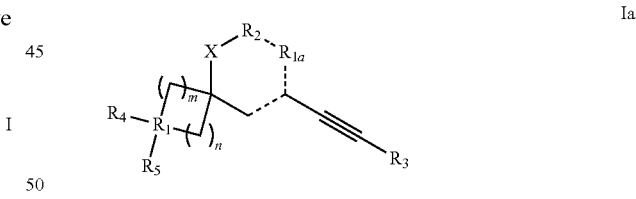

Ia wherein:
X is oxygen or sulfur;
$R_1$ is carbon, nitrogen, oxygen or sulfur;
$R_{1a}$ is CH, $CH_2$, N, or NH;
$R_2$ is a bond, a CH group or a $CH_2$ group;
$R_3$ is an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group;
$R_4$ is absent or is an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, an optionally substituted alkyl group, hydroxy, alkoxy, thiol, thioalkyl, amino, N-alkylamino, or N,N-dialkylamino or a halogen atom;

$R_5$ is absent or is optionally substituted alkyl, hydroxy, alkoxy, thiol, thioalkyl, amino, alkylamino, dialkylamino, cyano, aminocarbonyl, alkylaminocarbonyl, dialkylaminocarbonyl, N-alkoxy-N-alkylaminocarbonyl, alkoxycarbonyl, aryloxycarbonyl, heteroaryloxycarbonyl, heterocyclylcarbonyl, heteroarylcarbonyl, heterocyclyaminocarbonyl heterocyclylaminocarbonyl, each one optionally substituted or a halogen atom; or when $R_1$ is a carbon atom, $R_4$ and $R_5$ are joined together $R_1$ to form an optionally substituted methylene group, a keto group, or an optionally substituted oxime wherein the optional substituents is alkyl, cycloalkyl, halogen or a heterocyclic group; or when $R_1$ is a carbon atom, $R_4$ and $R_5$ are each carbon, oxygen, nitrogen, or sulfur linked to each other through an optionally substituted $C_1$-$C_3$ alkylene group;

m is 1-2;

n is 1-2;

o is 0-1; and

---- is a single or double bond; and enantiomers, diastereomers, and N-oxides thereof; and pharmaceutically acceptable salts thereof.

In one embodiment, the selective mGlu5 modulator, preferably antagonist, compounds of the present invention are used to treat a disorder of the lower urinary tract in a mammal. In this embodiment, the mGlu5 modulator, preferably antagonist, compounds of the present invention can be used to treat at least one symptom of a disorder of the lower urinary tract in a mammal.

Thus, the present invention provides a method of treating a symptom of urinary incontinence in a subject suffering from a lower urinary tract disorder, comprising administering to said subject a therapeutically effective amount of one or more of the compounds of the invention, alone or in combination with other therapeutic agents to treat urge incontinence, stress incontinence, mixed incontinence or overflow incontinence.

In certain embodiments, the compounds of the present invention are used for the treatment of a lower urinary tract disorder selected from the group consisting of overactive bladder (OAB), interstitial cystitis, prostatitis, prostadynia and benign prostatic hyperplasia (BPH). In preferred embodiments, the invention provides treatment of urinary incontinence caused by or associated with such disorders.

In another embodiment, the selective mGlu5 modulator, preferably antagonist, compounds of the present invention are used for the treatment of migraine.

In a further embodiment, the selective mGlu5 modulator, preferably antagonist, compounds of the present invention are used for the treatment of gastroesophageal reflux disease (GERD) in mammals.

In a further embodiment, the selective mGlu5 modulator, preferably antagonist, compounds of the present invention are used for the treatment of anxiety in mammals.

In a further embodiment, the selective mGlu5 modulator, preferably antagonist compounds of the present invention are used for the treatment of abuse, substance dependence and substance withdrawal disorders in mammals.

In a further embodiment, the selective mGlu5 modulator, preferably antagonist compounds of the present invention are used for the treatment of fragile X syndrome disorders in mammals.

DETAILED DESCRIPTION OF THE INVENTION

We have tested the activity of selective mGlu1 and selective mGlu5 modulators in a rat model that is useful to detect activity on the lower urinary tract. Surprisingly, good activity was found for modulators selective for the mGlu5 receptor, whereas two commercially available antagonists selective for mGlu1 receptor failed to exhibit an effect. A modulator, preferably antagonist selective for Group II mGluR receptors also failed to exhibit an effect in the rat model. Given these results, selective mGlu5 antagonists can be an effective means to treat lower urinary tract disorders.

Accordingly, the present inventors have unexpectedly found that administration of negative allosteric modulators of the glutamate mGlu5 receptor, which include "mGlu5 antagonists," provide a potent inhibition of the micturition reflex. Without wishing to be bound by any particular theory or mechanism of action, these novel compounds of present invention are thought to act in the CNS by negatively modulating the excitatory signaling to the bladder giving, as a final result, an increase of the bladder volume capacity. These modulators are thus useful for treatment of lower urinary tract disorders and symptoms thereof as described in, e.g., International Patent Application WO 04/067002 (Recordati), which is incorporated by reference herein in its entirety.

Novel Compounds of the Invention

The present invention is related to the compounds of formula I as disclosed above. The invention includes the enantiomers, diastereomers, N-oxides (e.g., piperidine N-oxides), crystalline forms, hydrates, solvates or pharmaceutically acceptable salts of the formula I compounds, as well as active metabolites of these compounds having a similar type type of activity. The novel compounds of the invention are selective mGlu5 modulators, preferably antagonists, useful in, for example, the treatment of lower urinary tract disorders and for the alleviation of the symptoms associated therewith.

Except where stated otherwise, the following definitions apply throughout the present specification and claims. These definitions apply regardless of the whether a term is used by itself or in combination with other terms. Hence the definition of "alkyl" applies to "alkyl" as well as to the "alkyl" portions of "alkoxy," "alkylamino," etc. Furthermore, all ranges described for chemical groups, for example, the ranges "from 1 to 20 carbon atoms" and "$C_1$-$C_6$ alkyl," include all combinations and subcombinations of ranges and specific numbers of carbon atoms therein.

As used above, and throughout the specification, the following terms, unless otherwise indicated, shall be understood to have the following meanings:

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain, which may be straight or branched. Branched means that one or more lower alkyl groups such as methyl, ethyl or propyl are attached to a linear alkyl chain. "Lower alkyl" means an alkyl group having about 1 to about 6 carbon atoms in the chain which may be straight or branched. The term "optionally substituted alkyl" means that the alkyl group may be substituted by one or more substituents preferably 1-6 substituents, which may be the same or different, each substituent being independently selected from the groups as defined below. Non-limiting examples of suitable alkyl groups include methyl, ethyl, n-propyl, isopropyl, sec-butyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain. More preferably about 2 to about 6 carbon atoms in the chain. Branched means that one or more lower alkyl groups such as methyl, ethyl or propyl, are attached to a linear alkenyl chain or that a lower alkenyl group is attached to a linear alkyl chain. "Lower alkenyl" means an alkenyl group having 2 to about 6 carbon atoms in the chain, which may be straight or branched. The term "optionally substituted alkenyl" means that the alkenyl group may be substituted by one or more substituents, preferably 1-6 substituents, which may be the same or different, each substituents being independently selected from the groups as defined below. Non-limiting examples of suitable alkenyl groups include ethenyl, propenyl, isopropenyl, n-butenyl, 1-hexenyl and 3-methylbut-2-enyl.

"Alkynyl" means an aliphatic hydrocarbon group comprising at least one carbon-carbon triple bond and which may be straight or branched and comprising 2 to about 15 carbon atoms in the chain. Preferred alkynyl groups have 2 to about 12 carbon atoms in the chain. More preferably 2 to about 6 carbon atoms in the chain. Branched alkynyl means that one or more lower alkyl groups such as methyl, ethyl or propyl, are attached to a linear alkynyl chain or that an alkyne group is attached to a linear alkyl group. "Lower alkynyl" means an alkynyl group having 2 to about 6 carbon atoms in the chain, which may be straight or branched. The term "optionally substituted alkynyl" means that the alkynyl group may be substituted by one or more substituents, preferably 1-6 substituents, which may be the same or different, each substituents being independently selected from the groups as defined below. Non-limiting examples of suitable alkynyl groups include ethynyl, propynyl and 2-butynyl.

"Mono-, bi- or tricyclic aryl" means an aromatic monocyclic, bicyclic or tricyclic ring system comprising 6 to 14 carbon atoms. Bi- and tricyclic aryl groups are fused at 2 or 4 points or joined at one point via a bond or a heteroatom linker (O, S, NH, or N($C_1$-$C_6$ alkyl) (e.g., biphenyl, 1-phenyl-napthyl, diphenyl ether). The aryl group can be optionally substituted on the ring with one or more substituents, preferably 1 to 6 substituents, which may be the same or different each substituent being independently selected from the groups as defined below. Non-limiting examples of suitable aryl groups include phenyl and naphthyl. The "mono, bi or tricyclic aryl" group can also be substituted by linking two adjacent carbons on its aromatic ring via a combination of 1 to 4 carbon atoms and 1 to 3 oxygen atoms such as, for example, methylenedioxy, ethylenedioxy, and the like. Also included within the scope of the term "aryl" as it is used herein is a group in which the aryl ring is fused at two points directly or joined at one point via a bond or a heteroatom linker (O, S, NH, or N($C_1$-$C_6$ alkyl), to one or two non-aromatic carbacyclic or heterocyclic or heteroaromatic rings. Non limiting examples include indenyl, 1-phenyl-1H-imidazole, 5-phenyl isoxazole, 4-phenyl-1,2,3 thiadiazole, 2-phenylpyrimidine, quinoline, 3,4-dihydro-2H-benzo[b][1,4]oxazine, benzo[d]thiazol-2(3H)-one, 1-phenylpyrrolidin-2-one, 1-phenylazetidin-2-one and the like.

"Mono-, bi-, or tricyclic heterocyclic" means an aromatic or non-aromatic saturated mono bi or tricyclic ring system having 2 to 14 ring carbon atoms, and containing 1-5 ring atoms chosen from NH, N—(CO)—$C_{1-6}$ alkyl, N$C_{1-6}$-alkyl, O, $SO_2$ and S, alone or in combination. Bi- and tricyclic heterocyclic groups are fused at 2 or 4 points or joined at one point via a bond or a heteroatom linker (O, S, NH, or N($C_1$-$C_6$ alkyl). The "mono-, bi-, or tricyclic heterocyclic" can be optionally substituted on the ring by replacing an available hydrogen on the ring by one or more substituents which may be the same or different, each being independently selected from the groups defined below. There are no adjacent oxygen and or sulfur atoms present in the ring system. The nitrogen or sulfur atom of the heterocyclic can be optionally oxidized to the corresponding N-oxide, S-oxide or S-dioxide. Non-limiting examples of suitable heterocyclic include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, or benzoisoxazolyl. Non Limiting examples of suitable heterocyclic rings include also aziridinyl, piperidinyl, pyrrolidinyl, piperazinyl, tetrahydropyranyl, tetrahydrofuranyl, tetrahydrothiophenyl, morpholinyl, thiomorpholinyl and the like. Also included with in the scope of the term "heterocyclic" as it is used herein is a group in which the heterocyclic ring is fused at two points or joined at one point via a bond or a heteroatom linker (O, S, NH, or N($C_1$-$C_6$ alkyl), to one aromatic, or cycloalkyl ring, non limiting examples include isoindoline-1,3-dione-1-methyl-2-phenyl-1H-pyrazole-3(2H)-one, indoline and the like.

"Mono-, bi-, or tricyclic heteroaromatic" is included within the group of Mono-, bi-, or tricyclic heterocyclic, and means an aromatic mono-, bi-, or tricyclic ring system having 1 to 14 ring carbon atoms, and containing 1-5 ring atoms chosen from N, NH, N—(CO)—$C_{1-6}$ alkyl, N$C_{1-6}$-alkyl, O, S, SO, $SO_2$ alone or in combination. Bi- and tricyclic aryl groups are fused at 2 or 4 points or joined at one or two points via a bond and/or a heteroatom linker (O, S, NH, or N($C_1$-$C_6$ alkyl). The "mono-, bi-, or tricyclic heteroaromatic" can be optionally substituted on the ring by replacing an available hydrogen on the ring by one or more substituents which may be the same or different, each being independently selected from the groups defined below. A nitrogen atom of the mono or bicyclic heteroaromatic can be optionally oxidized to the corresponding N-oxide. Non-limiting examples of suitable heteroaromatics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, or benzoisoxazolyl. Also included within the scope of the term "heteroaromatic", as it is used herein, is a group in which a heteroatomic ring is fused at two points or joined at one point via a bond or a heteroatom linker (O, S, NH, or N($C_1$-$C_6$ alkyl), to one nonaromatic, aromatic or heterocyclic rings where the radical or point of attachment is on the heteroaromatic ring. Non-limiting examples include tetrahydroquinolinyl, tetrahydroisoquinolinyl, 3-phenylpyridine, 3-cyclohexylpyridine, 3-(pyridin-3-yl)morpholine, 3-phenylisoxazole, 2-(piperidin-1-yl)pyrimidine and the like.

"Mono-, or bicyclic or multicyclic cycloalkyl" means a non aromatic mono-, bicyclic, or multicyclic ring system comprising 3 to about 14 carbon atoms, preferably 3-6 carbon atoms. The cycloalkyl group may optionally contain one or two double bonds within the ring (e.g., cyclohexenyl, cyclohexadiene). The cycloalkyl can be optionally substituted on the ring by replacing an available hydrogen on the ring by one or more substituents which may be the same or different, each being independently selected from the groups as defined below. Non-limiting examples of suitable monocyclic cycloalkyls include cyclopropyl, cyclopentyl, cyclohexyl, cycloheptyl and the like. Non-limiting examples of suitable multicyclic cycloalklys include 1-decalinyl, norbornyl, adamantyl and the like.

"Alkoxy" means an alkyl-O-group in which the alkyl group is as previously described. Non-limiting examples of suitable alkoxy groups include methoxy, ethoxy, n-propoxy and isopoxy. The alkyl group is linked to an adjacent moiety through the ether oxygen.

"Halogen" or "halo" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Oxo" means a =O moiety. A "keto group" means a —C(=O)— moiety

The term "alkanoyl" refers to radicals having a carbonyl radical as defined below, attached to an alkyl radical. Preferred alkanoyl radicals are "lower alkanoyl" radicals having 1-6 carbon atoms. The alkanoyl radicals may be substituted or unsubstituted, such as formyl, acetyl, propionyl (propanoyl), butanoyl (butyryl), isobutanoyl (isobutyryl), valeryl (pentanoyl), isovaleryl, pivaloyl, hexanoyl or the like.

The term "carbonyl", whether used alone or with other terms, such as "alkylcarbonyl", denotes —(C=O)—. The term "alkylcarbonyl" refers to radicals having a carbonyl radical substituted with an alkyl radical. More preferred alkylcarbonyl radicals are "lower alkylcarbonyl" radicals having one to six carbon atoms. Examples of such radicals include methylcarbonyl and ethylcarbonyl. The terms "alkanoyl" and "alkylcarbonyl" are synonymous.

The term "alkanoyloxy" refers to an "alkanoyl" radical as defined above linked to an oxygen radical, to generate an ester group.

The term "aminocarbonyl" when used by itself or with other terms such as "aminocarbonylalkyl", "N-alkylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$. The terms "N-alkylaminocarbonyl" and "N,N-dialkylaminocarbonyl" denote aminocarbonyl radicals in which the amino groups have been substituted with one alkyl radical and two alkyl radicals, respectively. Preferred are "lower alkylaminocarbonyl" having lower alkyl radicals as described above attached to an aminocarbonyl radical The term "alkylthio" refers to radicals containing a linear or branched alkyl radical, of one to ten carbon atoms, attached to a divalent sulfur atom. An example of "alkylthio" is methylthio, (CH$_3$—S—).

The term "amino" refers to the radical —NH$_2$.

The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to the nitrogen atom. Examples of "alkylamino" include N-methylamino, N-ethylamino, N,N-dimethylamino, N,N-diethylamino or the like.

The term "acyl", whether used alone, or within a term such as "acylamino", denotes a radical provided by the residue after removal of hydroxyl from an organic acid. The term "acylamino" refers an amino radical substituted with an acyl group. An examples of an "acylamino" radical is acetylamino or acetamido (CH$_3$C(=O)—NH—) where the amine may be further substituted with alkyl, aryl or aralkyl.

The term "aryloxy" refers to the radical —O-aryl. Examples of such radicals include phenoxy.

The term "cyano" refers to the radical —C≡N.

The term "nitro" refers to the radical —NO$_2$.

The term "heterocycloalkyl" refers to the radical -Alkyl-Heterocycle.

The term "hydroxy" refers to the radical —OH.

The term "optionally substituted" means optional substitution on a specified moiety with one or more, preferably 1-8 groups, radicals or moieties which have a molecular mass of less than 300 preferably less than 200 and more preferably less than 150; independently selected for each position capable of substitution on the specified moiety.

In specific embodiments, "optionally substituted" refers to substitution with one or more of alkyl, alkenyl, alkynyl, halo, hydroxy, nitro, cyano, amino, thiol, alkoxy, N-alkylamino, or N,N-dialkylamino.

Nonlimiting examples of optional substituents for the compounds of formulas I are independently hydroxy, nitro, cyano, amino, thiol, alkyl, alkenyl, alkynyl, alkoxy, N-alkylamino, or N,N-dialkylamino, halogen, oxo, aryloxy or heteroaryloxy, carbamoyl, sulfamoyl, (di)alkylaminocarbonyl, (di)alkylaminosulphonyl, alkoxycarbonyl, (poly)haloalkyl, $C_1$-$C_6$ alkylsulphonyl, $C_1$-$C_6$ alkylthio, (di)$C_1$-$C_6$ alkylthio, (di)$C_1$-$C_6$ alkylcarbonylamino, $C_1$-$C_6$ alkylcarbonyl or $C_1$-$C_6$ alkylcarbonyl-($C_1$-$C_6$)alkyl group, or or a group of the formula —NR*R* wherein each R* independently represents a hydrogen atom or a $C_1$-$C_6$ alkyl, $C_1$-$C_6$ alkylcarbonyl, phenyl or benzyl group, or $C_1$-$C_6$ alkyl, $C_2$-$C_6$ alkenyl, $C_2$-$C_6$ alkynyl or $C_1$-$C_6$ alkoxy group, each of which may optionally bear from 1 to 8 substitutents independently selected from oxo, halo, cyano, nitro, amino, hydroxy and phenyl; or $C_3$-$C_9$ mono- or bicycloalkyl group each of which may be optionally bear from 1 to 3 substituents independently selected from $C_1$-$C_6$ alkyl, oxo, halo, cyano, nitro, amino, hydroxy and phenyl substituents; or an optionally substituted mono- or bicyclic $C_1$-$C_9$ heterocyclic group containing from 1 to 3 heteroatoms selected from nitrogen, oxygen and sulfur; or an optionally substituted mono-, bi- or tricyclic $C_6$-$C_{14}$ aryl group, or an optionally substituted $C_3$-$C_7$ cycloalkyl group; or a group of the formula -A, —O-A, —C(O)-A, —(CH$_2$)$_q$-A, —NR-A, —C(O)NR-A, —NR**C(O)-A or —OC(O)-A, wherein A is a phenyl group or a $C_1$-$C_8$ heterocyclic group containing from 1 to 3 heteroatoms selected from N, O, and S; each group A of being optionally substituted with from 1 to 3 groups independently selected from halo, hydroxy, cyano, nitro and $C_1$-$C_6$ alkyl;

R** is independently selected from hydrogen and $C_1$-$C_6$ alkyl, and q is an integer from 1 to 6.

In some embodiments, preferred compounds of Formula I are those in which $R_4$ is null and $R_1$ is carbon or nitrogen and m and n are 2 and o is 0. Especially preferred are compounds of Formula II or III:

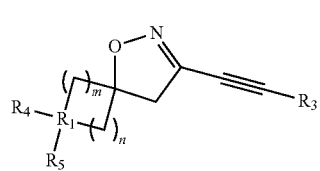

II

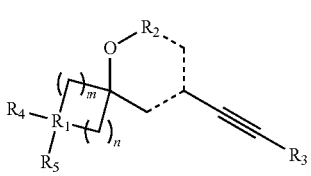

III wherein the groups $R_1$, $R_2$, $R_3$, $R_4$ and $R_5$ are as defined above.

Further specific compounds according to formulas I, Ia, II and III are where $R_1$ is nitrogen, $R_5$ is absent, and $R_4$ is an optionally substituted mono- or bicyclic or tricyclic $C_1$-$C_{13}$ heterocyclic group containing from 1 to 5 heteroatoms selected from N, O, and S.

In some embodiments, $R_4$ represents an optionally substituted mono-, bi- or tricyclic $C_1$-$C_9$ heterocyclic group containing 1 to 5 heteroatoms selected from N, O, and S. For example, $R_4$ is an optionally substituted group selected from phenyl, furanyl, thienyl, isoxazolyl, pyridinyl, and pyrazinyl. In some embodiments the optional substituent on the $R_4$ group is selected from one or more of halogen, alkyl, alkoxy, nitro, amino, hydroxyl, carboxyl, cyano, and trifluoromethyl. Even more preferably, $R_4$ is a pyridinyl group optionally substituted with one or more of alkyl and nitro, or a pyrazinyl optionally substituted with cyano.

Additional compounds according to formulas I, Ia, II and III are where $R_4$ is hydroxyl, and $R_5$ is heteroarylalkyl, more preferably pyridinylmethyl;

Further compounds according to formulas I, Ia, II or III are wherein $R_1$ is carbon, and $R_4$ and $R_5$ are linked together to form an optionally substituted methylene, an optionally substituted oxime, or a keto group. In some of these compounds, $R_4$ and $R_5$ are linked together to form an methylene optionally substituted with pyridyl, an oxime optionally substituted with alkyl, or a lactone, or a keto group In some compounds according to formulas I, Ia, II or III, $R_1$ is carbon and $R_5$ and $R_4$ are independently carbon, oxygen, NH, or S joined together through a $C_1$-$C_3$ alkylene group to form a spirocycle, or $R_4$ is cyano and $R_5$ is a monocyclic heteroaromatic containing 1-3 nitrogens. In more specific embodiments $R_4$ and $R_5$ are oxygen and the spirocyclic ring is an optionally substituted 1,3-dioxolanyl or 1,3-dioxanyl ring or a tetrahydrofuranyl ring. In still more specific embodiments $R_4$ is cyano and $R_5$ is a pyridinyl.

In other compounds according to formulas I, Ia, II or III, $R_3$ is $C_1$-$C_6$ alkyl or cycloalkyl, optionally substituted phenyl or optionally substituted monocyclic $C_1$-$C_6$ heteroaromatic group containing from 1 to 4 heteroatoms selected from the group consisting of N, S, and O. In more specific groups of compounds, $R_3$ is optionally substituted phenyl, thienyl, furanyl, thiazolyl, pyrazinyl, oxadiazolyl or pyridinyl In other groups of such compounds $R_3$ is optionally substituted phenyl or pyridinyl. Preferably, the optional substituent is selected from halogen, alkyl, alkoxy, nitro, amino, hydroxyl, carboxyl, cyano, and trifluoromethyl.

In other compounds according to formulas I, Ia, II or III, $R_4$ is an optionally substituted $C_1$-$C_6$ alkyl group, an optionally substituted mono-, bi- or tricyclic $C_1$-$C_{13}$ heterocyclic group containing 1 to 5 heteroatoms selected from the group consisting of N, S, and O; an optionally substituted mono-, bi-, or tricyclic $C_6$-$C_{14}$ aryl group, an optionally substituted $C_3$-$C_6$ cycloalkyl group, or an optionally substituted $C_3$-$C_6$ cycloalkenyl group.

In some embodiments, $R_4$ is an optionally substituted mono- bi- or tricyclic $C_1$-$C_{13}$ heterocyclic group containing 1 to 5 heteroatoms selected from the group consisting of N, S, and O; or an optionally substituted mono, bi or tricyclic $C_6$-$C_{14}$ aryl group. In more specific embodiments $R_4$ is a mono- or bicyclic $C_1$-$C_9$ heterocyclic group containing 1 to 3 heteroatoms selected from the group consisting of N, S, and O, and at least 2 adjacent carbon atoms.

In one embodiment, $R_4$ is an optionally substituted group selected from phenyl, pyridyl, pyrazinyl, and thienyl. Preferably, the optional substituent is selected from halogen, alkyl, alkoxy, nitro, amino, hydroxyl, carboxyl, cyano, and trifluoromethyl. Especially preferred amongst this group are compounds wherein $R_4$ is a pyridyl or phenyl group substituted with an electron withdrawing group, for example, a cyano or nitro group, and/or a methyl or methoxy group, with further substituents being optional. Most preferably, $R_4$ is 3-nitro-2-pyridyl, 6-methyl-3-nitro-2-pyridyl, 6-methyl-3-cyano-2-pyridyl, 4-methoxy-3-cyano-2-pyridyl, 3-cyano-2-thienyl, or 3-cyano-2-pyrazinyl.

In some compounds of Formulas I, II, and III, m is 1, n is 1; m is 2 and n is 2 and o is 0; m is 2 and n is 1; and m is 1, n is 1 and o is 1 and o is O.

In other compounds ft, is $CH_2$, $R_{1a}$ is CH and there is a double bond between $R_{1a}$ and the carbon substituted with the alkynyl, or there is a double bond between the carbon substituted with the alkynyl and the other adjacent carbon.

Specific embodiments are compounds selected from the group consisting of:

8-(6-Methyl-3-nitropyridin-2-yl)-3-(phenylethynyl)-1-oxa-2,8-diazaspiro[4.5]dec-2-ene;

8-(3-Nitropyridin-2-yl)-3-(phenylethynyl)-1-oxa-2,8-diazaspiro[4.5]dec-2-ene;

8-(6-Methyl-3-nitropyridin-2-yl)-3-[(6-methylpyridin-2-yl)ethynyl]-1-oxa-2,8-diazaspiro[4.5]dec-2-ene;

8-(6-Methyl-3-nitropyridin-2-yl)-3-(thien-2-ylethynyl)-1-oxa-2,8-diazaspiro[4.5]dec-2-ene;

8-(6-Methyl-3-nitropyridin-2-yl)-3-(pyridin-2-ylethynyl)-1-oxa-2,8-diazaspiro[4.5]dec-2-ene;

3-[(2-Fluorophenyl)ethynyl]-8-(6-methyl-3-nitropyridin-2-yl)-1-oxa-2,8-diazaspiro[4.5]dec-2-ene;

3-[(3-Fluorophenyl)ethynyl]-8-(6-methyl-3-nitropyridin-2-yl)-1-oxa-2,8-diazaspiro[4.5]dec-2-ene;

3-[(4-Fluorophenyl)ethynyl]-8-(6-methyl-3-nitropyridin-2-yl)-1-oxa-2,8-diazaspiro[4.5]dec-2-ene;

3-(2-Furylethynyl)-8-(6-methyl-3-nitropyridin-2-yl)-1-oxa-2,8-diazaspiro[4.5]dec-2-ene;

8-(6-Methyl-3-nitropyridin-2-yl)-3-[(2-methyl-1,3-thiazol-4-yl)ethynyl]-1-oxa-2,8-diazaspiro[4.5]dec-2-ene;

8-(6-Methyl-3-nitropyridin-2-yl)-3-prop-1-ynyl-1-oxa-2,8-diazaspiro[4.5]dec-2-ene;

3-[(3-Chlorophenyl)ethynyl]-8-(6-methyl-3-nitropyridin-2-yl)-1-oxa-2,8-diazaspiro[4.5]dec-2-ene;

8-(6-Methyl-3-nitropyridin-2-yl)-3-[(3-methylphenyl)ethynyl]-1-oxa-2,8-diazaspiro[4.5]dec-2-ene;

3-[(3-Methoxyphenyl)ethynyl]-8-(6-methyl-3-nitropyridin-2-yl)-1-oxa-2,8-diazaspiro[4.5]dec-2-ene;

3-{[8-(6-Methyl-3-nitropyridin-2-yl)-1-oxa-2,8-diazaspiro[4.5]dec-2-en-3-yl]ethynyl}benzonitrile;

8-(6-Methyl-3-nitropyridin-2-yl)-3-(thien-3-Ylethynyl)-1-oxa-2,8-diazaspiro[4.5]dec-2-ene;

8-(6-Methyl-3-nitropyridin-2-yl)-3-(pyridin-3-ylethynyl)-1-oxa-2,8-diazaspiro[4.5]dec-2-ene;

8-(6-Methyl-3-nitropyridin-2-yl)-3-[3-(3-methyl-[1,2,4]oxadiazol-5-yl)phenylethynyl]-1-oxa-2,8-diaza-spiro[4.5]dec-2-ene;

3-(3-Methylbut-1-ynyl)-8-(6-methyl-3-nitropyridin-2-yl)-1-oxa-2,8-diaza-spiro[4.5]dec-2-ene;

3-Hex-1-ynyl-8-(6-methyl-3-nitropyridin-2-yl)-1-oxa-2,8-diazaspiro[4.5]dec-2-ene;
2-{[8-(6-Methyl-3-nitropyridin-2-yl)-1-oxa-2,8-diazaspiro[4.5]dec-2-en-3-yl]ethynyl}benzonitrile;
3-[3-(3-Chlorophenylethynyl)-1-oxa-2,8-diazaspiro[4.5]dec-2-en-8-yl]pyrazine-2-carbonitrile;
8-(6-Methyl-3-nitropyridin-2-yl)-3-[(2-methylphenyl)ethynyl]-1-oxa-2,8-diazaspiro[4.5]dec-2-ene;
3-[(2-Chlorophenyl)ethynyl]-8-(6-methyl-3-nitropyridin-2-yl)-1-oxa-2,8-diazaspiro[4.5]dec-2-ene;
8-(6-Methyl-3-nitropyridin-2-yl)-3-(pyrazin-2-ylethynyl)-1-oxa-2,8-diazaspiro[4.5]dec-2-ene;
8-(6-Methyl-3-nitropyridin-2-yl)-3-(phenylethynyl)-1-oxa-8-azaspiro[4.5]dec-3-ene;
3-[(3-Chlorophenyl)ethynyl]-7-(6-methyl-3-nitropyridin-2-yl)-1-oxa-2,7-diazaspiro[4.4]non-2-ene;
7-[(3-Chlorophenyl)ethynyl]-2-(6-methyl-3-nitropyridin-2-yl)-5-oxa-2,6-diazaspiro[3.4]oct-6-ene;
9-(6-Methyl-3-nitropyridin-2-yl)-4-(2-phenylethynyl)-1-oxa-9-azaspiro[5.5]undec-4-ene;
9-(6-Methyl-3-nitropyridin-2-yl)-4-(2-phenylethynyl)-1-oxa-9-azaspiro[5.5]undec-3-ene;
3-[(3-Chlorophenyl)ethynyl]-1,9,12-trioxa-2-azadispiro[4.2.4.2]tetradec-2-ene;
3-[(3-Chlorophenyl)ethynyl]-1-oxa-2-azaspiro[4.5]dec-2-en-8-one;
3-[(3-Chlorophenyl)ethynyl]-8-methylene-1-oxa-2-azaspiro[4.5]dec-2-ene;
3-[(3-Chlorophenyl)ethynyl]-1-oxa-2-azaspiro[4.5]dec-2-en-8-one O-methyloxime;
7-(6-Methyl-3-nitropyridin-2-yl)-3-[(6-methylpyridin-2-yl)ethynyl]-1-oxa-2,7-diazaspiro[4.4]non-2-ene;
7-(6-Methyl-3-nitropyridin-2-yl)-3-(phenylethynyl)-1-oxa-2,7-diazaspiro[4.4]non-2-ene;
3-[(3-Fluorophenyl)ethynyl]-7-(6-methyl-3-nitropyridin-2-yl)-1-oxa-2,7-diazaspiro[4.4]non-2-ene;
2-(6-Methyl-3-nitropyridin-2-yl)-7-(phenylethynyl)-5-oxa-2,6-diazaspiro[3.4]oct-6-ene;
3-{[7-(6-Methyl-3-nitropyridin-2-yl)-1-oxa-2,7-diazaspiro[4.4]non-2-en-3-yl]ethynyl}phenol
7-[(3-Fluorophenyl)ethynyl]-2-(6-methyl-3-nitropyridin-2-yl)-5-oxa-2,6-diazaspiro[3.4]oct-6-ene;
3-[(3-Chlorophenyl)ethynyl]-8-(pyridin-2-ylmethylene)-1-oxa-2-azaspiro[4.5]dec-2-ene;
3-[(3-Chlorophenyl)ethynyl]-8-(pyridin-2-ylmethyl)-1-oxa-2-azaspiro[4.5]dec-2-en-8-one;
3-[(3-Chlorophenyl)ethynyl]-8-(pyridin-2-ylmethyl)-1-oxa-2-azaspiro[4.5]dec-2-en-8-one;
3-(Phenylethynyl)-1,9,12-trioxa-2-azadispiro[4.2.4.2]tetradec-2-ene;
3-(2-Phenylethynyl)-1-oxa-2-azaspiro[4.5]dec-2-en-8-one;
3-(2-Phenylethynyl)-1-oxa-2-azaspiro[4.5]dec-2-en-8-one oxime;
3-(Phenylethynyl)-1-oxa-2-azaspiro[4.5]dec-2-en-8-one O-(2-oxotetrahydrofuran-3-yl)oxime;
3-[(6-Methylpyridin-2-yl)ethynyl]-8-pyridin-2-yl-1-oxa-2-azaspiro[4.5]dec-2-ene-8-carbonitrile;
3-[(5-Fluoropyridin-2-yl)ethynyl]-1,9,12-trioxa-2-azadispiro[4.2.4.2]tetradec-2-ene;
3-[(6-Methylpyridin-2-yl)ethynyl]-1,9,12-trioxa-2-azadispiro[4.2.4.2]tetradec-2-ene;
3-[(6-Fluoropyridin-2-yl)ethynyl]-1,9,12-trioxa-2-azadispiro[4.2.4.2]tetradec-2-ene;
3-[(6-Fluoropyridin-2-yl)ethynyl]-1,9,12-trioxa-2-azadispiro[4.2.4.2]tetradec-2-ene;
3-[(3-Nitrophenyl)ethynyl]-1,9,12-trioxa-2-azadispiro[4.2.4.2]tetradec-2-ene;
3-[(2-Methyl-1,3-thiazol-4-yl)ethynyl]-1,9,12-trioxa-2-azadispiro[4.2.4.2]tetradec-2-ene;
3-[(3-Methoxyphenyl)ethynyl]-1,9,12-trioxa-2-azadispiro[4.2.4.2]tetradec-2-ene;
3-[(3-Chloro-5-fluorophenyl)ethynyl]-1,9,12-trioxa-2-azadispiro[4.2.4.2]tetradec-2-ene;
3-[(3-Methyphenyll)ethynyl]-1,9,12-trioxa-2-azadispiro[4.2.4.2]tetradec-2-ene;
3-[(3-Ethoxyphenyll)ethynyl]-1,9,12-trioxa-2-azadispiro[4.2.4.2]tetradec-2-ene
3-[(3-Trifluoromethoxyphenyl)ethynyl]-1,9,12-trioxa-2-azadispiro[4.2.4.2]tetradec-2-ene;
3-[(3-tert-Butylphenyl)ethynyl]-1,9,12-trioxa-2-azadispiro[4.2.4.2]tetradec-2-ene;
3-(1,9,12-Trioxa-2-azadispiro[4.2.4.2]tetradec-2-en-3-ylethynyl)benzonitrile;
3-[(3-Fluorophenyl)ethynyl]-1,9,12-trioxa-2-azadispiro[4.2.4.2]tetradec-2-ene;
3-[(3-Ethylphenyl)ethynyl]-1,9,12-trioxa-2-azadispiro[4.2.4.2]tetradec-2-ene;
3-[(3-Isopropylphenyl)ethynyl]-1,9,12-trioxa-2-azadispiro[4.2.4.2]tetradec-2-ene;
3-[(4-Chloropyridin-2-yl)ethynyl]-1,9,12-trioxa-2-azadispiro[4.2.4.2]tetradec-2-ene;
3-[(4-Methylpyridin-2-yl)ethynyl]-1,9,12-trioxa-2-azadispiro[4.2.4.2]tetradec-2-ene;
3-[(3-Trifluoromethylphenyl)ethynyl]-1,9,12-trioxa-2-azadispiro[4.2.4.2]tetradec-2-ene;
3-{[4-(Trifluoromethyl)pyridin-2-yl]ethynyl}-1,9,12-trioxa-2-azadispiro[4.2.4.2]tetradec-2-ene;
3-[(5-Chloropyridin-3-yl)ethynyl]-1,9,12-trioxa-2-azadispiro[4.2.4.2]tetradec-2-ene;
1-(2-Furyl)-3-(1,9,12-trioxa-2-azadispiro[4.2.4.2]tetradec-2-en-3-yl)prop-2-yn-1-one;
4-Hydroxy-2-({[3-(phenylethynyl)-1-oxa-2-azaspiro[4.5]dec-2-en-8-ylidene]amino}oxy)butanoic acid;
3-[(3-Chlorophenyl)ethynyl]-1,8-dioxa-2-azaspiro[4.5]dec-2-ene;
3-[(6-Methylpyridin-2-yl)ethynyl]-1,8-dioxa-2-azaspiro[4.5]dec-2-ene;
3-[(4-Chloropyridin-2-yl)ethynyl]-1,8-dioxa-2-azaspiro[4.5]dec-2-ene;
3-[(3-Chlorophenyl)ethynyl]-1-oxa-8-thia-2-azaspiro[4.5]dec-2-ene 8,8-dioxide;
3-[(3-Chlorophenyl)ethynyl]-1,7-dioxa-2-azaspiro[4.5]dec-2-ene;
3-[(3-Chlorophenyl)ethynyl]-1,9-dioxa-2-azadispiro[4.2.4.2]tetradec-2-ene;
3-[(3-Chlorophenyl)ethynyl]-1,9-dioxa-2-azadispiro[4.2.4.2]tetradec-2-ene;
3-[(3-Methylphenyl)ethynyl]-1,9-dioxa-2-azadispiro[4.2.4.2]tetradec-2-ene;
3-{[2-(6-Methyl-3-nitropyridin-2-yl)-5-oxa-2,6-diazaspiro[3.4]oct-6-en-7-yl]ethynyl}phenol;
3-{[2-(6-Methyl-3-nitropyridin-2-yl)-5-oxa-2,6-diazaspiro[3.4]oct-6-en-7-yl]ethynyl}benzonitrile;
3'-[(3-Chlorophenyl)ethynyl]-2,3-dihydro-4'H-spiro[indene-1,5'-isoxazol]-3-ol;
3'-[(3-Chlorophenyl)ethynyl]-4'H-spiro[indene-1,5'-isoxazol]-3(2H)-one;
3'-[(3-Chlorophenyl)ethynyl]-N-methoxy-4'H-spiro[indene-1,5'-[1,2]oxazol]-3(2H)-imine;
10-[(3-Chlorophenyl)ethynyl]-1,8-dioxa-9-azadispiro[3.2.4.2]tridec-9-ene (isomer 1);
10-[(3-Chlorophenyl)ethynyl]-1,8-dioxa-9-azadispiro[3.2.4.2]tridec-9-ene (isomer 2);

3-[(3-Chlorophenyl)ethynyl]-1,9,13-trioxa-2-azadispiro[4.2.5.2]pentadec-2-ene;
3'-[(6-Methylpyridin-2-yl)ethynyl]-2,3-dihydro-4'N-spiro[indene-1,5'-[1,2]oxazol]-3-ol;
3-[(3-Chlorophenyl)ethynyl]-1-oxa-2-azadispiro[4.2.4.2]tetradec-2-ene;
3-[(3-Chlorophenyl)ethynyl]-8,8-difluoro-1-oxa-2-azaspiro[4.5]dec-2-ene;
3-[(3-Methylphenyl)ethynyl]-1-oxa-2-azadispiro[4.2.4.2]tetradec-2-ene;
3-[(6-Methoxypyridin-3-yl)ethynyl]-1,9,12-trioxa-2-azadispiro[4.2.4.2]tetradec-2-ene;
3'-[(6-Methylpyridin-2-yl)ethynyl]-4'H-spiro[indene-1,5'-[1,2]oxazol]-3(2H)-one;
N-Methoxy-3'-[(6-methylpyridin-2-yl)ethynyl]-4'H-spiro[indene-1,5'-[1,2]oxazol]-3(2H)-imine;
3-[(3-Chlorophenyl)ethynyl]-N,N-dimethyl-1-oxa-2,7-diazaspiro[4.4]non-2-ene-7-carboxamide;
3-[(3-Chlorophenyl)ethynyl]-1-oxa-2,7-diazaspiro[4.4]non-2-ene-7-carboxamide;
9-[(3-Chlorophenyl)ethynyl]-7-oxa-8-azadispiro[3.1.4.1]undec-8-ene;
3-[(3-Methylphenyl)ethynyl]-1,9,13-trioxa-2-azadispiro[4.2.5.2]pentadec-2-ene;
7-[(3-Chlorophenyl)ethynyl]-5-oxa-6-azaspiro[3.4]oct-6-ene;
10-[(3-Chlorophenyl)ethynyl]-2,8-dioxa-9-azadispiro[3.2.4.2]tridec-9-ene;
3-[(4-Chloropyridin-2-yl)ethynyl]-8,8-difluoro-1-oxa-2-azaspiro[4.5]dec-2-ene;
Ethyl 3-[(6-methylpyridin-2-yl)ethynyl]-1-oxa-2-azaspiro[4.5]dec-2-ene-8-carboxylate;
3'-[(3-Chlorophenyl)ethynyl]-1H,4'H-spiro[isochromene-4,5'-[1,2]oxazole];
{3-[(3-Chlorophenyl)ethynyl]-1-oxa-2,7-diazaspiro[4.4]non-2-en-7-yl}(4-methylpiperazin-1-yl)methanone;
1-({3-[(3-Chlorophenyl)ethynyl]-1-oxa-2,7-diazaspiro[4.4]non-2-en-7-yl}carbonyl)imidazolidin-2-one;
[7-[2-(3-Chlorophenyl)ethynyl]-9-oxa-3,8-diazaspiro[4.4]non-7-en-3-yl]-pyrrolidin-1-yl-methanone;
[7-[2-(3-Chlorophenyl)ethynyl]-9-oxa-3,8-diazaspiro[4.4]non-7-en-3-yl]-(1-piperidyl)methanone;
1-[7-[2-(3-Chlorophenyl)ethynyl]-9-oxa-3,8-diazaspiro[4.4]non-7-ene-3-carbonyl]-3-methylsulfonyl-imidazolidin-2-one;
3-[(3-Chlorophenyl)ethynyl]-N-ethyl-N-(propan-2-yl)-1-oxa-2,7-diazaspiro[4.4]non-2-ene-7-carboxamide;
7-[2-(3-Chlorophenyl)ethynyl]-N-methoxy-N-methyl-9-oxa-3,8-diazaspiro[4.4]non-7-ene-3-carboxamide;
7-[2-(3-Chlorophenyl)ethynyl]-N-(4-pyridyl)-9-oxa-3,8-diazaspiro[4.4]non-7-ene-3-carboxamide;
Ethyl 3-[(3-chlorophenyl)ethynyl]-1-oxa-2,7-diazaspiro[4.4]non-2-ene-7-carboxylate;
8,8-Difluoro-2-[2-(6-methyl-2-pyridyl)ethynyl]-4-oxa-3-azaspiro[4.5]dec-2-ene;
6-[2-(3-Chlorophenyl)ethynyl]-2,8-dioxa-7-azaspiro[3.4]oct-6-ene;
2-[2-(3-Chlorophenyl)ethynyl]-4-oxa-3-azaspiro[4.5]dec-2-ene;
2-[2-(3-Chlorophenyl)ethynyl]-8-(difluoromethylene)-4-oxa-3-azaspiro[4.5]dec-2-ene;
2-[2-(3-Chlorophenyl)ethynyl]-4-oxa-3,8-diazaspiro[4.5]dec-2-ene-8-carboxamide;
[2-[2-(3-Chlorophenyl)ethynyl]-4-oxa-3,8-diazaspiro[4.5]dec-2-en-8-yl]-(2-furyl)methanone;
2-[2-(3-Chlorophenyl)ethynyl]-N-methoxy-N-methyl-4-oxa-3,8-diazaspiro[4.5]dec-2-ene-8-carboxamide;
2-[2-(3-Chlorophenyl)ethynyl]-N,N-diethyl-4-oxa-3,8-diazaspiro[4.5]dec-2-ene-8-carboxamide;
(3-Chlorophenyl)-[2-[2-(3-chlorophenyl)ethynyl]-4-oxa-3,8-diazaspiro[4.5]dec-2-en-8-yl]methanone;
Ethyl 2-[2-(3-chlorophenyl)ethynyl]-4-oxa-3,8-diazaspiro[4.5]dec-2-ene-8-carboxylate;
[2-[2-(3-Chlorophenyl)ethynyl]-4-oxa-3,8-diazaspiro[4.5]dec-2-en-8-yl]-pyrrolidin-1-yl-methanone;
2-[2-(3-Chlorophenyl)ethynyl]-N,N-dimethyl-4-oxa-3,8-diazaspiro[4.5]dec-2-ene-8-carboxamide;
Tert-butyl 2-[2-(3-chlorophenyl)ethynyl]-9-methoxy-4-oxa-3,7-diazaspiro[4.4]non-2-ene-7-carboxylate; and
Ethyl 2-[2-(3-chlorophenyl)ethynyl]-9-methoxy-4-oxa-3,7-diazaspiro[4.4]non-2-ene-7-carboxylate.

A combination of substituents or variables is permissible only if such a combination results in a stable or chemically feasible compound. A stable compound or chemically feasible compound is one in which the chemical structure is not substantially altered when kept a temperature of about 50° C. or less, in the absence of moisture or other chemically reactive conditions, for at least 7 days.

The present invention also provides for pharmaceutical compositions comprising one or more compounds of Formula I and a pharmaceutically acceptable excipient.

The present invention is based on the finding that selective mGlu5 modulator, preferably antagonist, compounds are useful in the treatment of lower urinary tract disorders, such as neuromuscular dysfunction of the lower urinary tract, and in the treatment of migraine and in astroesophageal reflux disease (GERD) in mammals. mGlu5 modulators, preferably antagonists are useful also in the treatment of anxiety disorder in mammals, and in the treatment of abuse, substance dependence and substance withdrawal disorders in mammals.

Another use of mGlu5 modulators, preferably antagonists is related to the treatment of fragile X syndrome disorder.

Thus, the compounds of the invention are mGlu5 modulators, preferably antagonists useful in the treatment of neuromuscular dysfunction of the lower urinary tract, migraine and in gastroesophageal reflux disease (GERD) in mammals. In jurisdictions in which methods of treatment of humans and animals are considered patentable, the invention extends to methods for the treatment of neuromuscular dysfunction of the lower urinary tract, for the treatment of migraine and for the treatment of gastroesophageal reflux disease (GERD) in mammals.

In one embodiment, the selective mGlu5 modulators, preferably antagonist compounds of the present invention are used to treat a disorder of the lower urinary tract in a mammal. In this embodiment, the mGlu5 modulators, preferably antagonist compounds of the present invention can be used to treat at least one symptom of a disorder of the lower urinary tract in a mammal.

Thus, the present invention provides a method of treating a symptom of urinary incontinence in a subject suffering from a lower urinary tract disorder, comprising administering to said subject a therapeutically effective amount of one or more of the compounds of the invention, alone or in combination with other therapeutic agents to treat urge incontinence, stress incontinence, mixed incontinence or overflow incontinence.

In certain embodiments, the compounds of the present invention are used for the treatment of a lower urinary tract disorder selected from the group consisting of overactive bladder (OAB), interstitial cystitis, prostatitis, prostadynia and benign prostatic hyperplasia (BPH). In preferred embodiments, the invention provides treatment of urinary incontinence caused by or associated with such disorders.

In another embodiment, the selective mGlu5 modulators, preferably antagonist compounds of the present invention are used for the treatment of migraine.

In a further embodiment, the selective mGlu5 modulators, preferably antagonist compounds of the present invention are used for the treatment of gastroesophageal reflux disease (GERD) in mammals.

In a further embodiment, the selective mGlu5 modulators, preferably antagonist compounds of the present invention are used for the treatment of anxiety in mammals.

In a further embodiment, the selective mGlu5 modulators, preferably antagonist compounds of the present invention are used for the treatment of abuse, substance dependence and substance withdrawal disorders in mammals.

In a further embodiment, the selective mGlu5 modulators, preferably antagonist compounds of the present invention are used for the treatment of fragile X syndrome disorder in mammals.

Salts, solvates, stereoisomers, derivatives, prodrugs and active metabolites of the novel compounds of the invention.

The present invention further encompasses salts, solvates, stereoisomers, prodrugs and active metabolites of the compounds of formula I, Ia, II or III.

The term "salts" can include acid addition salts or addition salts of free bases. Preferably, the salts are pharmaceutically acceptable. Examples of acids which may be employed to form pharmaceutically acceptable acid addition salts include, but are not limited to, salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, et al. "Pharmaceutical Salts," *J. Pharma. Sci.* 1977; 66:1).

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the federal or a state government or listed in the U.S. Pharmacopoeia or other generally recognized pharmacopeias for use in mammals, and more particularly in humans.

Typically, a pharmaceutically acceptable salt of a compound of formula I, Ia, II or III may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I and the resulting mixture evaporated to dryness (lyophilized) to obtain the acid addition salt as a solid. Alternatively, a compound of formula I, Ia, II or III may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the compounds of formula I, Ia, II or III may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Also included are both total and partial salts, that is to say salts with 1, 2 or 3, preferably 2, equivalents of base per mole of acid of a formula I, Ia, II or III compound or salt, with 1, 2 or 3 equivalents, preferably 1 equivalent, of acid per mole of base of a formula I, Ia, II or III compound.

For the purposes of isolation or purification it is also possible to use pharmaceutically unacceptable salts. However, only the pharmaceutically acceptable, non-toxic salts are used therapeutically and they are therefore preferred.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner. The free acid form may be regenerated by contacting the salt form with an acid and isolating the free acid.

Compounds of the invention may have both a basic and an acidic center and may therefore be in the form of zwitterions or internal salts.

Typically, a pharmaceutically acceptable salt of a compound of formula I, Ia, II or III may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I, Ia, II or III and the resulting mixture evaporated to dryness (lyophilized) to obtain the acid addition salt as a solid. Alternatively, a compound of formula I, Ia, II or III may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formulae I, Ia II, or III may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. *Polymorphism in Pharmaceutical solids*. Marcel Decker, New York, 1999.).

The present invention also encompasses N-oxides of the compounds of formulas I. The term "N-oxide" means that for heterocycles containing an otherwise unsubstituted sp$^2$N atom, the N atom may bear a covalently bound O atom, i.e., —N→O. Examples of such N-oxide substituted heterocycles include pyridyl N-oxides, pyrimidyl N-oxides, pyrazinyl N-oxides and pyrazolyl N-oxides.

Compounds of formula I, Ia, II or III may have one or more chiral centers and, depending on the nature of individual substituents, they can also have geometrical isomers. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has a chiral center, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomer respectively). A chiral compound can exist as either an individual enantiomer or as a mixture of enantiomers. A mixture containing equal proportions of the enantiomers is called a "racemic mixture". A mixture containing unequal portions of the enantiomers is described as having an "enantiomeric excess" (ee) of either the R or S compound. The excess of one enantiomer in a mixture is often described with a % enantiomeric excess (% ee) value determined by the formula:

% $ee=(R)-(S)/(R)+(S)$

The ratio of enantiomers can also be defined by "optical purity" wherein the degree at which the mixture of enantiomers rotates plane polarized light is compared to the individual optically pure R and S compounds. Optical purity can be determined using the following formula:

Optical purity=enant.$_{major}$/(enant.$_{major}$+enant.$_{minor}$)

The present invention encompasses all individual isomers of the compounds of formula I, Ia, II or III. The description or naming of a particular compound in the specification and claims is intended to include both individual enantiomers and mixtures, racemic or otherwise, thereof. Methods for the determination of stereochemistry and the resolution of stereoisomers are well-known in the art.

For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions. Those of skill in the art will further recognize that invention compounds may exist in polymorphic forms wherein a compound is capable of crystallizing in different forms. Suitable methods for identifying and separating polymorphisms are known in the art.

Diastereisomers differ in both physical properties and chemical reactivity. A mixture of diastereomers can be separated into enantiomeric pairs based on solubility, fractional crystallization or chromatographic properties, e.g., thin layer chromatography, column chromatography or HPLC.

Purification of complex mixtures of diastereomers into enantiomers typically requires two steps. In a first step, the mixture of diastereomers is resolved into enantiomeric pairs, as described above. In a second step, enantiomeric pairs are further purified into compositions enriched for one or the other enantiomer or, more preferably resolved into compositions comprising pure enantiomers. Resolution of enantiomers typically requires reaction or molecular interaction with a chiral agent, e.g., solvent or column matrix. Resolution may be achieved, for example, by converting the mixture of enantiomers, e.g., a racemic mixture, into a mixture of diastereomers by reaction with a pure enantiomer of a second agent, i.e., a resolving agent. The two resulting diastereomeric products can then be separated. The separated diastereomers are then reconverted to the pure enantiomers by reversing the initial chemical transformation.

Resolution of enantiomers can also be accomplished by differences in their non-covalent binding to a chiral substance, e.g., by chromatography on homochiral adsorbants. The noncovalent binding between enantiomers and the chromatographic adsorbant establishes diastereomeric complexes, leading to differential partitioning in the mobile and bound states in the chromatographic system. The two enantiomers therefore move through the chromatographic system, e.g, column, at different rates, allowing for their separation.

Chiral resolving columns are well known in the art and are commercially available (e.g., from MetaChem Technologies Inc., a division of ANSYS Technologies, Inc., Lake Forest, Calif.). Enantiomers can be analyzed and purified using, for example, chiral stationary phases (CSPs) for HPLC. Chiral HPLC columns typically contain one form of an enantiomeric compound immobilized to the surface of a silica packing material.

D-phenylglycine and L-leucine are examples of Type I CSPs and use combinations of π-π interactions, hydrogen bonds, dipole-dipole interactions, and steric interactions to achieve chiral recognition. To be resolved on a Type I column, analyte enantiomers must contain functionality complementary to that of the CSP so that the analyte undergoes essential interactions with the CSP. The sample should preferably contain one of the following functional groups: π-acid or π-base, hydrogen bond donor and/or acceptor, or an amide dipole. Derivatization is sometimes used to add the interactive sites to those compounds lacking them. The most common derivatives involve the formation of amides from amines and carboxylic acids.

The MetaChiral ODM™ is an example of a type II CSP. The primary mechanisms for the formation of solute-CSP complexes is through attractive interactions, but inclusion complexes also play an important role. Hydrogen bonding, π-π interactions, and dipole stacking are important for chiral resolution on the MetaChiral™ ODM. Derivatization may be necessary when the solute molecule does not contain the groups required for solute-column interactions. Derivatization, usually to benzylamides, may be required for some strongly polar molecules like amines and carboxylic acids, which would otherwise interact strongly with the stationary phase through non-specific-stereo interactions.

Compounds of formula I, Ia, II or III can be separated into diastereomeric pairs by, for example, separation by column chromatography or TLC on silica gel. These diastereomeric pairs are referred to herein as diastereomer with upper TLC Rf, and diastereomer with lower TLC Rf. The diastereomers can further be enriched for a particular enantiomer or resolved into a single enantiomer using methods well known in the art, such as those described herein.

The relative configuration of the diastereomeric pairs can be deduced by the application of theoretical models or rules (e.g. Cram's rule, the Felkin-Ahn model) or using more reliable three-dimensional models generated by computational chemistry programs. In many instances, these methods are able to predict which diasteromer is the energetically favoured product of a chemical transformation. As an alternative, the relative configuration of the diastereomeric pairs can be indirectly determined by discovering the absolute configurations of a single enantiomer in one (or both) of the diastereomeric pair(s).

The absolute configuration of the stereocenters can be determined by very well known method to those skilled in the art (e.g. X-Ray diffraction, circular dichroism). Determination of the absolute configuration can be useful also to confirm the predictability of theoretical models and can be helpful to extend the use of these models to similar molecules prepared by reactions with analogous mechanisms (e.g. ketone reductions and reductive amination of ketones by hydrides).

The present invention also encompasses stereoisomers of the Z-E type, and mixtures thereof due to $R_2$-$R_3$ substituents to the double bond not directly linked to the ring. Additional Z-E stereoisomers are encountered when m is not 1 and m and n are different. The Cahn-Ingold-Prelog priority rules are applied to determine whether the stereoisomers due to the respective position in the plane of the double bond of the doubly bonded substituents are Z or E. The stereoisomer is designated as Z (zusammen=together) if the 2 groups of highest priority lie on the same side of a reference plane passing through the C=C bond. The other stereoisomer is designated as E (entgegen=opposite).

Mixture of stereoisomers of E-Z type can be separated (and/or characterized) in their components using classical method of purification that are based on the different chemico-physical properties of these compounds. Included in these method are fractional crystallization, chromatography carried out by low, medium or high pressure techniques, fractional distillation and any other method very well known to those skilled in the art.

The present invention also encompasses prodrugs of the compounds of formula I, Ia, II or III, i.e., compounds which release an active parent drug according to formula I, Ia, II or III in vivo when administered to a mammalian subject. A prodrug is a pharmacologically active or more typically an inactive compound that is converted into a pharmacologically active agent by a metabolic transformation. Prodrugs of a compound of formula I are prepared by modifying functional groups present in the compound of formula I, Ia, II or III in such a way that the modifications may be cleaved in vivo to release the parent compound. In vivo, a prodrug readily undergoes chemical changes under physiological conditions (e.g., are acted on by naturally occurring enzyme(s)) resulting in liberation of the pharmacologically active agent. Prodrugs include compounds of formula I, Ia, II or III wherein a hydroxy, amino, or carboxy group of a formula I compound is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of formula I, Ia, II or III or any other derivative which upon being brought to the physiological pH or through enzyme action is converted to the active parent drug. Conventional procedures for the selection and preparation of suitable prodrug derivatives are described in the art (see, for example, Bundgaard. Design of Prodrugs. Elsevier, 1985).

Prodrugs may be administered in the same manner as the active ingredient to which they convert or they may be delivered in a reservoir form, e.g., a transdermal patch or other reservoir which is adapted to permit (by provision of an enzyme or other appropriate reagent) conversion of a prodrug to the active ingredient slowly over time, and delivery of the active ingredient to the patient.

Unless specifically indicated, the term "active ingredient" is to be understood as referring to a compound of formula I, Ia, II or III as defined herein.

The present invention also encompasses metabolites. "Metabolite" of a compound disclosed herein is a derivative of a compound which is formed when the compound is metabolised. The term "active metabolite" refers to a biologically active derivative of a compound which is formed when the compound is metabolised. The term "metabolised" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyses a variety of oxidative and reductive reactions while uridine diphosphate glucuronyltransferases catalyse the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996), pages 11-17.

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

Use of the Compounds of the Invention

Another embodiment of the present invention is method of treating diseases or disorders of the lower urinary tract, including neuromuscular dysfunctions of the lower urinary tract, comprising administering to a mammal in need of such treatment an effective amount of a compound according to Formula I, Ia, II or III or a pharmaceutically acceptable salt thereof.

Further preferred are where the aforementioned neuromuscular dysfunction is selected from the group consisting of urinary urgency, overactive bladder, increased urinary frequency, decreased urinary compliance (decreased bladder storage capacity), cystitis, interstitial cystitis, incontinence, urine leakage, enuresis, dysuria, urinary hesitancy and difficulty in emptying the bladder.

Another embodiment of the present invention is method of treating neuromuscular dysfunctions of the lower urinary tract comprising administering to a mammal in need of such treatment an effective amount of a compound of the invention or a pharmaceutically acceptable salt thereof, administered in combination with an antimuscarinic drug. Preferably the antimuscarinic drug is selected from the group consisting of oxybuynin, tolterodine, darifenicin, solifenacin, trospium, imidafenacin, fesoterodine and temiverine.

Another embodiment of the present invention is method of treating neuromuscular dysfunctions of the lower urinary tract comprising administering to a mammal in need of such treatment an effective amount of a compound of the invention or a pharmaceutically acceptable salt thereof, administered in combination with α1-adrenergic antagonists. Preferably the adrenergic antagonists is selected from the group consisting of prazosin, doxazosin, terazosin, alfuzosin, silodosin and tamsulosin.

Another embodiment of the present invention is method of treating neuromuscular dysfunctions of the lower urinary tract comprising administering to a mammal in need of such treatment an effective amount of a compound of the invention or a pharmaceutically acceptable salt thereof, administered in combination with a serotonin and/or noradrenalin reuptake inhibitor. Preferably the serotonin and/or noradrenalin reuptake inhibitor is selected form the group consisting of duloxetine, milnacipran, amoxapine, venlafaxine, des-venlafaxine, sibutramine, tesofensine and des-methylsibutramine.

Another embodiment of the present invention, is method of treating neuromuscular dysfunctions of the lower urinary tract comprising administering to a mammal in need of such treatment an effective amount of a compound of the invention or a pharmaceutically acceptable salt thereof, administered in combination with a selective or non-selective COX inhibitor. Preferably the selective or non-selective COX inhibitor is selected from the group consisting of ibuprofen, naproxen, benoxaprofen, flurbiprofen, fenoprfen, ketoprofen, indoprofen, pirprofen, carprofen, tioxaprofe, suprofen, tiaprofenic acid, fluprofen, indomethacin, sulindac, tolmetin, zomepirac, diclofenac, fenclofenac, ibufenac, acetyl salicylic acid, piroxicam, tenoxicam, nabumetone, ketorolac, azapropazone, mefenamic acid, tolfenamic acid, diflunisal, acemetacin, fentiazac, clidanac, meclofenamic acid, flufenamic acid, niflumic acid, flufenisal, sudoxicam, etodolac, salicylic acid, benorylate, isoxicam, 2-fluoro-α-methyl[1,1'-biphenyl]-4-acetic acid 4-(nitrooxy)butyl ester, meloxicam, parecoxib and nimesulide.

Another embodiment of the present invention is a method of treating migraine comprising administering to a mammal in need of such treatment an effective amount of a compound of the invention or a pharmaceutically acceptable salt thereof.

Another embodiment of the present invention is a method of treating GERD comprising administering to a mammal in need of such treatment an effective amount of a compound of the invention or a pharmaceutically acceptable salt thereof.

Another embodiment of the present invention is a method of treating anxiety disorder comprising administering to a mammal in need of such treatment an effective amount of a compound of the invention or a pharmaceutically acceptable salt thereof.

Another embodiment of the present invention is a method of treating abuse, substance dependence and substance withdrawal disorder comprising administering to a mammal in need of such treatment an effective amount of a compound of the invention or a pharmaceutically acceptable salt thereof.

Another embodiment of the present invention is a method of treating neuropathic pain disorder comprising administering to a mammal in need of such treatment an effective amount of a compound of the invention or a pharmaceutically acceptable salt thereof.

Another embodiment of the present invention is a method of treating fragile X syndrome disorders comprising administering to a mammal in need of such treatment an effective amount of a compound of the invention or a pharmaceutically acceptable salt thereof.

The present invention also includes the enantiomers, diastereomers, N-oxides, crystalline forms, hydrates, solvates and pharmaceutically acceptable salts of the compounds of general formula I, Ia, II or III that are selective antagonists of mGlu5 receptors.

The present invention also includes metabolites of the compounds of formula I, Ia, II or III that are selective mGlu5 antagonists, hereinafter referred to as active metabolites.

The present invention also contemplates prodrugs which are metabolised in the body to generate the compounds of formula I, Ia, II or III that are selective mGlu5 antagonists.

In another embodiment, the present invention provides pharmaceutical compositions comprising compounds of formula I, Ia, II or III that are selective mGlu5 antagonists and enantiomers, diastereomers, N-oxides, crystalline forms, hydrates, solvates or pharmaceutically acceptable salts thereof, in admixture with pharmaceutically acceptable excipients, diluents or carriers such as those disclosed.

The selectivity of the compounds of the invention may be measured by:
(a) Individually measuring the binding affinity of a test compound for the mGlu5 receptor, mGlu1 receptor and Group II mGlu receptors;
(b) Identifying those test compounds that:
   (1) Bind to a mGlu5 receptor with an affinity of at least $10^{-6}$ M, and
   (2) Bind to a mGlu5 receptor with an affinity at least 10-fold stronger than the affinity for the mGlu1 receptor and Group II mGlu receptors.
(c) Individually measuring the ability of each of the compounds identified in step (b) to act as an antagonist or inverse agonist at the mGlu5 receptor.

Preferably, the activity of compounds identified in steps (a), (b), and (c) above is confirmed by evaluating the activity of the compound in treatment of lower urinary tract disease in humans or an animal model system. More preferably the compounds identified exhibit activity in increasing bladder volume capacity in conscious rats.

As stated above, in certain embodiments a selective mGlu5 antagonist is used to treat the aforementioned disorders by administering the antagonist in combination with known antimuscarinic drugs or serotonin and/or noradrenalin reuptake inhibitors. Analogously, a selective mGlu5 antagonist may be administered in combination with α1-adrenergic antagonists, for the therapy of lower urinary tract symptoms, whether or not these are associated with BPH. To the same purpose, selective mGlu5 antagonists may be administered in combination with inhibitors of the enzyme cyclooxygenase (COX) which may be selective or non-selective for the COX-2 isozyme.

Lower-Urinary Tract Disorders

The nomenclature of lower urinary tract symptoms and pathologies used herein is set forth in Abrams et al., *Neurol. and Urodyn.* 21:167-178 (2002) and Andersson et al., *Pharmacol. Rev.* 56:581-631 (2004).

Voiding dysfunctions can be roughly classified as disturbances of storage or emptying. Storage symptoms are experienced during the storage phase of the bladder, and include increased daytime frequency, nocturia (the waking at night one or more times to void), urgency (a sudden, compelling desire to pass urine that is difficult to defer), and urinary incontinence (the any involuntary leakage of urine). Urinary incontinence may be further characterized according to symptoms. Stress urinary incontinence is the involuntary leakage on effort or exertion, or on sneezing or coughing. Urge urinary incontinence is the involuntary leakage of urine accompanied by or immediately preceded by urgency. Mixed urinary incontinence is the involuntary leakage of urine associated with urgency and also with exertion, effort, sneezing or coughing. Overflow incontinence is the involuntary leakage of urine occurring after the bladder capacity has been exceeded, e.g., from a failure to empty. Enuresis also refers to any involuntary loss of urine. Nocturnal enuresis is the loss of urine occurring during sleep.

Voiding symptoms include slow stream, splitting or spraying of the urine stream, intermittent stream (intermittency, i.e., the stopping and restarting of urine flow during micturition, hesitancy (difficulty in initiating micturition resulting in a delay in the onset of voiding after the individual is ready to pass urine), straining and terminal dribble (a prolonged final part of micturition, when the flow has slowed to a trickle/dribble).

Lower urinary tract disorders may further be categorized by a constellation of symptoms (i.e., a syndrome) or by etiology. Individuals suffering from overactive bladder (OAB) syndrome, e.g., typically suffer from symptoms of urgency, urge incontinence, increased daytime frequency or nocturia. OAB occurs as a result of detrusor muscle overactivity referred to as detrusor muscle instability. Detrusor muscle instability can arise from non-neurological abnormalities, such as bladder stones, muscle disease, urinary tract infection or drug side effects or can be idiopathic.

Neurogenic overactive bladder (or neurogenic bladder) is a type of overactive bladder which occurs as a result of detrusor muscle overactivity referred to as detrusor hyperreflexia, secondary to known neurological disorders. Patients with neurological disorders, such as stroke, Parkinson's disease, diabetes, multiple sclerosis, peripheral neuropathy, or spinal cord lesions often suffer from neurogenic overactive bladder.

Cystitis (including interstitial cystitis) is a lower urinary tract disorder of unknown etiology that predominantly affects young and middle-aged females, although men and children can also be affected. Symptoms of interstitial cystitis can include voiding symptoms, increased daytime frequency, urgency, nocturia or suprapubic or pelvic pain related to and relieved by voiding. Many interstitial cystitis patients also experience headaches as well as gastrointestinal and skin problems. In some cases, interstitial cystitis can also be associated with ulcers or scars of the bladder.

Prostatitis and prostadynia are other lower urinary tract disorders that have been suggested to affect approximately 2-9% of the adult male population. Prostatitis is an inflammation of the prostate, and includes bacterial prostatitis (acute and chronic) and non-bacterial prostatitis. Acute and chronic bacterial prostatitis are characterized by inflammation of the prostate and bacterial infection of the prostate gland, usually associated with symptoms of pain, increased daytime frequency and/or urgency. Chronic bacterial prostatitis is distinguished from acute bacterial prostatitis based on the recurrent nature of the disorder. Chronic non-bacterial prostatitis is characterized by inflammation of the prostate which is of unknown etiology accompanied by the presence of an excessive amount of inflammatory cells in prostatic secretions not currently associated with bacterial infection of the prostate gland, and usually associated with symptoms of pain, increased daytime frequency and/or urgency. Prostadynia is a disorder which mimics the symptoms of prostatitis absent inflammation of the prostate, bacterial infection of the prostate and elevated levels inflammatory cells in prostatic secretions. Prostadynia can be associated with symptoms of pain, increased daytime frequency and/or urgency.

Benign prostatic hyperplasia (BPH) is a non-malignant enlargement of the prostate that is very common in men over 40 years of age. BPH is thought to be due to excessive cellular growth of both glandular and stromal elements of the prostate. Symptoms of BPH can include increased frequency, urgency, urge incontinence, nocturia, and voiding symptoms, including slow stream, splitting or spraying of the urine stream, intermittency, hesitancy, straining and terminal dribble.

In certain embodiments, the present invention provides the use of an effective amount of a compound of Formula I, Ia, II or III, for treating lower urinary tract disorders, including those described above, in a patient in need of such treatment. For example, treatment of lower urinary tract disorders also includes treatment of increased daytime frequency, nocturia, urgency, urinary incontinence, including urge incontinence, stress incontinence, mixed incontinence and overflow incontinence, enuresis, including nocturnal enuresis, slow stream, splitting or spraying of the urine stream, intermittency, hesitancy, straining and terminal dribble.

Treatment of lower urinary tract disorders also includes treatment of OAB syndrome, including treatment of one or more symptoms of urgency, urge incontinence, daytime frequency or nocturia.

Treatment of lower urinary tract disorders further encompasses treatment of any of the aforementioned conditions, symptoms and/or syndromes when caused by or associated with cystitis, including interstitial cystitis, prostatitis, BPH, neurological disorders, decreased urinary compliance (i.e., decreased bladder storage capacity).

In certain preferred embodiments, the compounds of Formula I, Ia, II or III are used to treat the involuntary passage of urine, i.e., urinary incontinence, e.g., urge incontinence, stress incontinence, mixed incontinence or overflow incontinence. In further preferred aspects of the invention, a mGlu5 antagonists is used to treat the involuntary passage of urine, i.e., urinary incontinence, e.g., urge incontinence, stress incontinence, mixed incontinence or overflow incontinence, that is caused by and/or associated with OAB or BPH.

Pharmaceutical Compositions Comprising a Compound of Formula I, Formula Ia, Formula II, or Formula III Another embodiment of the present invention are pharmaceutical compositions comprising a pharmaceutically acceptable excipient or diluent and a therapeutically effective amount of a compound of the invention, or an enantiomer, diastereomer, N-oxide or pharmaceutically acceptable salt thereof.

While it is possible that a compound may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

Accordingly, in one aspect, the present invention provides a pharmaceutical composition comprising at least one compound of formulas I, Ia, II, III or a pharmaceutically acceptable derivative (e.g., a salt or solvate) thereof, and, optionally, a pharmaceutically acceptable carrier. In particular, the invention provides a pharmaceutical composition comprising a therapeutically effective amount of at least one compound of formulas I, IA, II, III or a pharmaceutically acceptable derivative thereof, and, optionally, a pharmaceutically acceptable carrier.

For the methods of the invention, a compound of formulas I, Ia, II or III may be used in combination with other therapies and/or active agents. Accordingly, the present invention provides, in a further aspect, a pharmaceutical composition comprising at least one compound of formulas I, Ia, II, III, or a pharmaceutically acceptable derivative thereof, a second active agent, and, optionally a pharmaceutically acceptable carrier.

When combined in the same formulation it will be appreciated that the two compounds must be stable and compatible with each other and the other components of the formulation.

When formulated separately they may be provided in any convenient formulation, conveniently in such manner as are known for such compounds in the art.

The phrase "pharmaceutically acceptable" refers to molecular entities and compositions that are generally regarded as safe. In particular, pharmaceutically acceptable carriers used in the pharmaceutical compositions of this invention are physiologically tolerable and do not typically produce an allergic or similar untoward reaction (for example, gastric upset, dizziness and the like) when administered to a patient. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E.W. Martin, 18th Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see WO 02/00196 (SmithKline Beecham).

Routes of Administration and Unit Dosage Forms

The routes for administration (delivery) include, but are not limited to, one or more of: oral (e.g., as a tablet, capsule, or as an ingestible solution), topical, mucosal (e.g., as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

Therefore, the compositions of the invention include those in a form especially formulated for, e.g., parenteral, oral, buccal, rectal, topical, implant, ophthalmic, nasal or genitourinary use. In preferred embodiments, the pharmaceutical compositions of the invention are formulated in a form that is suitable for oral delivery.

There may be different composition/formulation requirements depending on the different delivery systems. It is to be understood that not all of the compounds need to be administered by the same route. Likewise, if the composition comprises more than one active component, then those components may be administered by different routes. By way of example, the pharmaceutical composition of the present invention may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, the compound of Formulas I, Ia, II or III may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intravenously, intramuscularly or subcutaneously. For buccal or sublingual administration the compositions may be administered in the form of tablets or lozenges, which can be formulated in a conventional manner.

Where the composition of the invention is to be administered parenterally, such administration includes one or more of: intravenously, intraarterially, intraperitoneally, intrathecally, intraventricularly, intraurethrally, intrasternally, intracranially, intramuscularly or subcutaneously administering the agent; and/or by using infusion techniques.

Pharmaceutical compositions of the present invention can be administered parenterally, e.g., by infusion or injection. Pharmaceutical compositions suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, or ascorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound of formulas I, with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the aldosterone receptor antagonists and desired excipients for subsequent preparation of sterile solutions.

The compounds according to the invention may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing and/or dispersing agents. Alternatively the active ingredient may be in sterile powder form for reconstitution with a suitable vehicle, e.g., sterile, pyrogen-free water, before use.

The compounds of the invention can be administered (e.g., orally or topically) in the form of tablets, capsules, ovules, elixirs, solutions or suspensions, which may contain flavoring or coloring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavoring and coloring agents. Solid compositions such as tablets, capsules, lozenges, pastilles, pills, boluses, powder, pastes, granules, bullets or premix preparations may also be used. Solid and liquid compositions for oral use may be prepared according to methods well-known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The compositions may be administered orally, in the form of rapid or controlled release tablets, microparticles, mini tablets, capsules, sachets, and oral solutions or suspensions, or powders for the preparation thereof. In addition to the new solid-state forms of pantoprazole of the present invention as the active substance, oral preparations may optionally include various standard pharmaceutical carriers and excipients, such as binders, fillers, buffers, lubricants, glidants, dyes, disintegrants, odorants, sweeteners, surfactants, mold release agents, antiadhesive agents and coatings. Some excipients may have multiple roles in the compositions, e.g., act as both binders and disintegrants.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the compositions of the invention include, but are not limited to, magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include, but are not limited to, hydroxypropylmethylcellulose, hydroxypropylcellulose and acrylate-methacrylate copolymers.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulphate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

The compounds of the invention may also, for example, be formulated as suppositories e.g., containing conventional suppository bases for use in human or veterinary medicine or as pessaries e.g., containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colorants, and odorants.

Examples of pharmaceutically acceptable polymers suitable for such topical compositions include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include but are not limited to, mineral oils, silicone oils, fatty acids, alcohols, and glycols.

Examples of suitable pharmaceutically acceptable liquid carriers include, but are not limited to, water, alcohols or glycols such as ethanol, isopropanol, propylene glycol, hexylene glycol, glycerol and polyethylene glycol, or mixtures thereof in which the pseudopolymorph is dissolved or dispersed, optionally with the addition of non-toxic anionic, cationic or non-ionic surfactants, and inorganic or organic buffers.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetriacetic acid (EDTA), thiourea, tocopherol and butyl hydroxyanisole.

Suitable examples of pharmaceutically acceptable moisturizers include, but are not limited to, glycerine, sorbitol, urea and polyethylene glycol.

Suitable examples of pharmaceutically acceptable emollients include, but are not limited to, mineral oils, isopropyl myristate, and isopropyl palmitate.

The compounds may also be dermally or transdermally administered, for example, by use of a skin patch.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride.

As indicated, the compounds of the present invention can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1, 2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active material.

The active agents can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage forms comprising an effective amount of the present invention may be administered to an animal, preferably a human, in need of treatment of neuromuscular dysfunction of the lower urinary tract described by E. J. McGuire in "Campbell's UROLOGY", 5$^{th}$ Ed., 616-638, 1986, W.B. Saunders Company.

As used herein, the term "effective amount" refers to an amount that results in measurable amelioration of at least one symptom or parameter of a specific disorder. In a preferred embodiment, the compound treats disorders of the urinary tract, such as urinary urgency, overactive bladder, increased urinary frequency, reduced urinary compliance (reduced bladder storage capacity), cystitis (including interstitial cystitis), incontinence, urine leakage, enuresis, dysuria, urinary hesitancy and difficulty in emptying the bladder. In another preferred embodiment the compound treats migraine. In other preferred embodiment the compound is used to treat GERD.

In other preferred embodiment the compound is used to treat neuropathic pain.

In other preferred embodiment the compound is used to treat anxiety.

In other preferred embodiment the compound is used to treat fragile X syndrome disorders.

In other preferred embodiment the compound is used to treat substance abuse, substance dependence and substance withdrawal disorders.

The pharmaceutical composition or unit dosage form of the present invention may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the active agents of the present invention may vary according to a variety of factors such as underlying disease conditions, the individual's condition, weight, sex and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of urinary tract disorders is within the scope of the invention. Clinically significant attenuation or amelioration means perceptible to the patient and/or to the physician.

For example, a single patient may suffer from several symptoms of dysuria simultaneously, such as, for example, urgency and excessive frequency of urination or both, and these may be reduced using the methods of the present invention. In the case of incontinence, any reduction in the frequency or volume of unwanted passage of urine is considered a beneficial effect of the present method of treatment.

The amount of the agent to be administered can range between about 0.01 and about 25 mg/kg/day, preferably between about 0.1 and about 10 mg/kg/day and most preferably between 0.2 and about 5 mg/kg/day. It will be understood that the pharmaceutical formulations of the present invention need not necessarily contain the entire amount of the agent that is effective in treating the disorder, as such effective amounts can be reached by administration of a plurality of doses of such pharmaceutical formulations.

In a preferred embodiment of the present invention, the compounds I are formulated in capsules or tablets, preferably containing 10 to 200 mg of the compounds of the invention, and are preferably administered to a patient at a total daily dose of 10 to 300 mg, preferably 20 to 150 mg and most preferably about 50 mg, for relief of urinary incontinence and other dysfunctions.

A pharmaceutical composition for parenteral administration contains from about 0.01% to about 100% by weight of the active agents of the present invention, based upon 100% weight of total pharmaceutical composition.

Generally, transdermal dosage forms contain from about 0.01% to about 100% by weight of the active agents versus 100% total weight of the dosage form.

For treatment of lower urinary tract disorders, the compound of the invention may be administered in combination with at least one compound of an additional class of therapeutic agents. Such additional class could be that of antimuscarinic drugs such as, without limitation, oxybutynin, tolterodine, darifenacin, solifenacin, trospium, fesoterodine and temiverine.

Combination therapy with, e.g. at least one mGlu5 antagonist, may further include treatment with an alpha1-adrenergic antagonist. Preferred alpha1-adrenergic antagonists suitable for administration in combination with mGlu5 modulators, preferably antagonists, are, for example, and without limitation, prazosin, doxazosin, terazosin, alfuzosin, silodosin, and tamsulosin. Additional alpha1-adrenergic antagonists suitable for administration in combination with mGlu5 antagonists are described in U.S. Pat. Nos. 5,990,114; 6,306,861; 6,365,591; 6,387,909; and 6,403,594, incorporated herein by reference in their entireties.

Combination therapy with at least one mGlu5 modulators, preferably antagonists, may further include treatment with a serotonin and/or noradrenaline reuptake inhibitor. Examples of serotonin and/or noradrenaline reuptake inhibitors include, without limitation, duloxetine, milnacipran, amoxapine, venlafaxine, des-venlafaxine, sibutramine, tesofensine and desmethylsibutramine.

In certain embodiments, a serotonin and/or noradrenalin reuptake inhibitor suitable for administration in combination with mGlu5 modulators, preferably antagonists, is a selective serotonin reuptake inhibitor (i.e., an SSRI). In certain embodiments, a serotonin and/or noradrenalin reuptake inhibitors suitable for administration in combination with mGlu5 modulators, preferably antagonists, is a selective noradrenalin reuptake inhibitor (i.e., an NARI).

Combination therapy with at least one compound of the invention may further include treatment with a selective or non selective COX inhibitor. Examples of COX inhibitors include, without limitations, ibuprofen, naproxen, benoxaprofen, flurbiprofen, fenoprofen, fenbufen, ketoprofen, indoprofen, pirprofen, carprofen, tioxaprofen, suprofen, tiaprofenic acid, fluprofen, indomethacin, sulindac, tolmetin, zomepirac, diclofenac, fenclofenac, ibufenac, acetyl salicylic acid, piroxicam, tenoxicam, nabumetone, ketorolac, azapropazone, mefenamic acid, tolfenamic acid, diflunisal, acemetacin, fentiazac, clidanac, meclofenamic acid, flufenamic acid, niflumic acid, flufenisal, sudoxicam, etodolac, salicylic acid, benorylate, isoxicam, 2-fluoro-α-methyl[1,1'- biphenyl]-4-acetic acid 4-(nitrooxy)butyl ester (see Wenk et al. Europ. J. Pharmacol. 453, 319-324 (2002)), meloxicam, parecoxib, nimesulide.

The pharmaceutical composition or unit dosage form may be administered in a single daily dose, or the total daily dosage may be administered in divided doses. In addition, co-administration or sequential administration of another compound for the treatment of the disorder may be desirable. To this purpose, the combined active principles are formulated into a simple dosage unit.

For combination treatment where the compounds are in separate dosage formulations, the compounds can be administered concurrently, or each can be administered at staggered intervals. For example, the compound of the invention may be administered in the morning and the antimuscarinic compound may be administered in the evening, or vice versa. Additional compounds may be administered at specific intervals too. The order of administration will depend upon a variety of factors including age, weight, sex and medical condition of the patient; the severity and aetiology of the disorders to be treated, the route of administration, the renal and hepatic function of the patient, the treatment history of the patient, and the responsiveness of the patient. Determination of the order of administration may be fine-tuned and such fine-tuning is routine in the light of the guidelines given herein.

Synthesis of the Compounds of the Invention

Compounds of formulas I, Ia, II and III and enantiomers, diastereomers, N-oxides, and pharmaceutically acceptable salts thereof may be prepared by the general methods outlined hereinafter, said methods constituting a further aspect of the invention. In the following description, the groups $R_{1-6}$ have the meaning defined for the compounds of formula I, Ia, II, or III unless otherwise stated.

It will be appreciated by those skilled in the art that it may be desirable to use protected derivatives of intermediates used in the preparation of the compounds I. Protection and deprotection of functional groups may be performed by methods known in the art (see, for example, Green and Wuts *Protective Groups in Organic Synthesis*. John Wiley and Sons, New York, 1999.). Hydroxy or amino groups may be protected with any hydroxy or amino protecting group. The amino protecting groups may be removed by conventional techniques. For example, acyl groups, such as alkanoyl, alkoxycarbonyl and aroyl groups, may be removed by solvolysis, e.g., by hydrolysis under acidic or basic conditions. Arylmethoxycarbonyl groups (e.g., benzyloxycarbonyl) may be cleaved by hydrogenolysis in the presence of a catalyst such as palladium-on-charcoal.

The synthesis of the target compounds is completed by removing any protecting groups which may be present in the penultimate intermediates using standard techniques, which are well-known to those skilled in the art. The deprotected final products are then purified, as necessary, using standard techniques such as silica gel chromatography, HPLC on silica gel and the like, or by recrystallization. In one embodiment, the compounds of the invention may be prepared according to Scheme A.

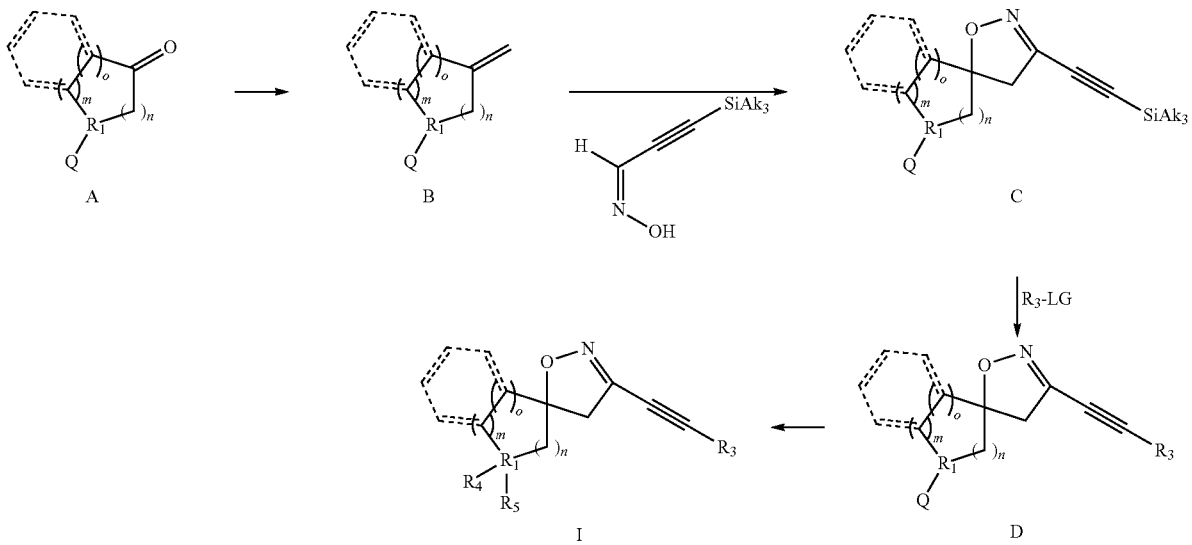

Q = Protecting Group (PG) or $R_4R_5$
LG = e.g., I, Br, Cl, OMs, OTf, or OTs

Starting material cyclic ketones A, are commercially available or easily prepared by standard methods known to those skilled in the art e.g. from piperidone (R1=N) with the carbonyl group that can or cannot be previously protected (e.g. as a ketal, for example as 1,3-dioxolane) by simple nucleophilic substitution of activated haloaryls, haloalkyls or haloheteroaryls, that can be carried out in a proper solvent like n-butanol or DMF or N-methylpyrrolidone or N,N-dimethylacetamide at a temperature between room temperature and the reflux of the selected solvent in the presence of a base, such as, for example, triethylamine or 4,4-dimethylaminopyridine. The reaction can be conducted also by the auxilium of microwave irradiation in a microwave apparatus to shorten the reaction time. An alternative general method for the preparation of piperidones from not activated haloaryls or haloheteroaryls (or triflates) is represented by the Buchwald-Hartwig amination using a palladium catalyst or by other metal catalyzed aminations. Very well known reductive amination procedures can be used where $R_4(R_5)$, is alkyl. Cyclic ketones A are reacted with the ylides, for example, obtained by the addition of a base (e.g. LiHMDS or potassium tert-butoxide in an aprotic solvent like THF or diethyl ether) to, e.g., methyltriphenylphosphonium bromide, to afford exomethylene derivatives B. Methylene derivatives B are, in turn, cyclized by using a 1,3-dipolar cycloaddition methodology to the alkynyl derivatives C (Hao-Wei Shih, Wei-Chie Cheng, Tetrahedron letters 49 (2008) 1008-1011, WO 20006/122770). To this end, trialkylsilylpropioladehydes oximes are converted in situ (or by isolating the intermediate) into the corresponding chloro or bromooximes (e.g. by the use of N-bromo succinimide or N-chlorosuccinimide or sodium ipochlorite or ipobromite or tert-butylipochlorite in a proper solvent such as dichloromethane or DMF with the addition or not of water), which are isolated or directly transformed inside the reaction vessel into the corresponding nitriloxides, by means of a mild base like $Na_2CO_3$ or triethylamine or etlymagnesium bromide or the like. Nitriloxide react quite easily with compounds 2 in a common solvent like dichloromethane or DMF usually at −78° C. to 0° up to r.t. or heating till to the reflux of the chosen solvent, yielding compounds C. These are then reacted with $R_3$-LG derivatives in a Sonogashira fashion to afford Compounds D.

The silyl protecting group of C is then removed by treatment with tetrabutylammonium fluoride in THF at a temperature in the range from ambient temperature to reflux or by hydrolysis with base ($K_2CO_3$ or KOH in MeOH) or other suitable method chosen from those reported in Greene-Wuts (Greene's Protective Groups in Organic Synthesis, 3rd Edition, Peter G. M. Wuts, Theodora W. Greene 1999, Wiley Interscience page 654-659) and well known by those skilled in the art. The so-obtained acetylenic compounds are then transformed into compounds D (not shown) by reacting them with $R_3$-LG following the well known Sonogashira procedure (Science of Synthesis, H. Heaney and S. Christie, October 2003, Vol. 3, Page 402 and following), that uses cuprous iodide and a palladium complex chosen from $(Ph_3P)_2PdCl_2$, $(Ph_3P)_2Pd(OAc)_2$, $(Ph_3P)_4Pd$ (which can also be generated in situ e.g. from triphenylphosphine and $Pd(OAc)_2$) and all the other palladium complexes cited in the literature and used for this kind of reaction, in the presence of a base such as TEA, DEA, DIPEA, TMA, butylamine, piperidine. Solvents are chosen among THF, DME, DMF, DMA, EtOAc, DMSO, toluene and others suitable for the purpose of the reaction; or the same base in excess can be used as the reaction solvent. If one carries out the reaction in DMF or DME, the isolation of compounds D can be avoided by adding the tetrabutylammonium fluoride or tetrabutylammonium chloride directly to the reaction medium containing C, before the coupling (Sorensen, U. S., Pombo-Villar, E. Tetrahedron 2005, 61, 2697-2703). The $R_3$ substituents are introduced using aryl or heteroaryl halides (preferred in decreasing order iodide, bromide, chloride), aryl or heteroaryl triflates, alkyl halogenides or acyl chlorides, aroyl chlorides, heteroaroyl chlorides. Triflates are synthesized using very well known method to people who have skills in the art, e.g. from phenols or hydroxyaryls (heteroaryls) using trifluoromethanesulphonic anhydride in a chlorinated solvent or using N-phenyltriflimide in toluene or a chlorinated solvent in the presence or not of a base (e.g. TEA). Both processes can be accelerated with the aid of microwaves performing the reaction in a microwave oven. Other suitable leaving groups LG for $R_3$-LG are nonaflates, tosylates and potassium trifluoborates.

Where $R_3$ is Ak an alternative procedure to Sonogashira coupling is the reaction of compounds D with lithium base (e.g. butyl lithium or LHDMS) in a proper solvent e.g. to produce the lithium alkinyl derivative, which on turn is reacted with a suitable electrophile like e.g. butyl iodide or the like in the same solvent or in alternative aprotic solvent like toluene at a temperature arnging from −20° C. to the reflux of the chosen solvent.

If compounds D are obtained, where Q is a protecting group, they need further deprotection and N-arylation/alkylation or other kinds of derivatization steps to afford Compound I.

Compounds D can be obtained by directly reacting compounds 2 with properly derivatized propioladehyde oxime where the $R_3$ group replace the trialkylsilyl group.

In some embodiments, the compounds of the invention, especially those of Formula Ia, II, and III, are generally prepared according to the following schemes:

Scheme 1

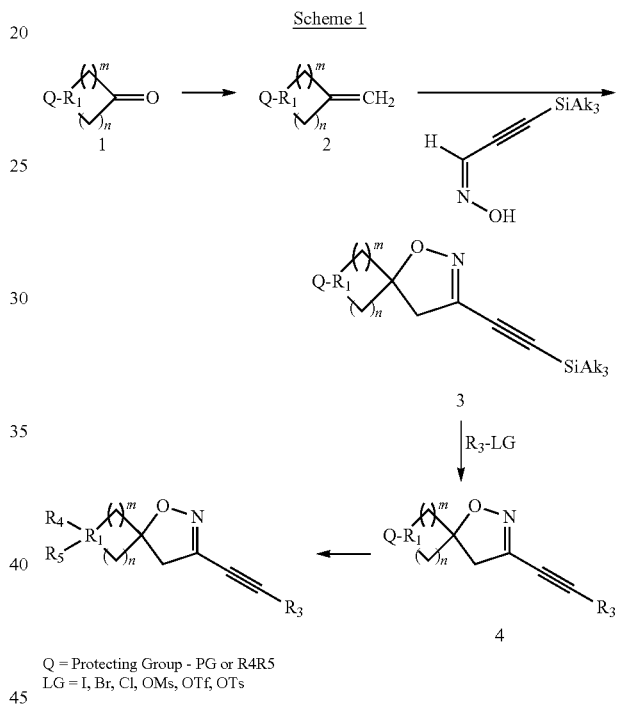

Q = Protecting Group - PG or R4R5
LG = I, Br, Cl, OMs, OTf, OTs

In Scheme 1, "Ak" represents a lower alkyl group, and the remaining variables are as defined for the general formula I or inside the scheme itself.

Starting material cyclic ketones 1, are commercially available or easily prepared by standard methods known to those skilled in the art e.g from piperidone (R1=N) with the carbonyl group that can or cannot be previously protected (e.g. as a ketal, for example as 1,3-dioxolane) by simple nucleophilic substitution of activated haloaryls, haloalkyls or haloheteroaryls, that can be carried out in a proper solvent like n-butanol or DMF or N-methylpyrrolidone or N,N-dimethylacetamide at a temperature between room temperature and the reflux of the selected solvent in the presence of a base, such as, for example, triethylamine or 4,4-dimethylaminopyridine. The reaction can be conducted also by the auxilium of microwave irradiation in a microwave apparatus to shorten the reaction time. An alternative general method for the preparation of piperidones from not activated haloaryls or haloheteroaryls (or triflates) is represented by the Buchwald-Hartwig amination using a palladium catalyst or by other metal catalyzed aminations. Very well known reductive amination procedures can be used where $R_4(R_5)_1$ is alkyl. Cyclic ketones 1 are reacted with the ylides, for example, obtained by the addition of a base (e.g. LiHMDS or potassium tert-butoxide in an aprotic solvent like THF or diethyl ether) to, e.g., methyltriphenylphosphonium bromide, to afford exomethylene derivatives 2. Methylene derivatives 2 are, in turn, cyclized by using a 1,3-dipolar cycloaddition methodology to the alkynyl derivatives 3 (Hao-Wei Shih, Wei-Chie Cheng, Tetrahedron letters 49 (2008) 1008-1011, WO 20006/122770). To this end, trialkylsilylpropioladehydes oximes are converted in situ (or by isolating the intermediate) into the corresponding chloro or bromooximes (e.g. by the use of N-bromo succinimide or N-chlorosuccinimide or sodium ipochlorite or ipobromite or tert-butylipochlorite in a proper solvent such as dichloromethane or DMF with the addition or not of water), which are isolated or directly transformed inside the reaction vessel into the corresponding nitriloxides, by means of a mild base like $Na_2CO_3$ or triethylamine or etlymagnesium bromide or the like. Nitriloxide react quite easily with compounds 2 in a common solvent like dichloromethane or DMF usually at $-78°$ C. to $0°$ up to r.t. or heating till to the reflux of the chosen solvent, yielding compounds 3. These are then reacted with $R_3$-LG derivatives in a Sonogashira fashion to afford Compounds 4.

The silyl protecting group of 3 is then removed by treatment with tetrabutylammonium fluoride in THF at a temperature in the range from ambient temperature to reflux or by hydrolysis with base ($K_2CO_3$ or KOH in MeOH) or other suitable method chosen from those reported in Greene-Wuts (Greene's Protective Groups in Organic Synthesis, 3rd Edition, Peter G. M. Wuts, Theodora W. Greene 1999, Wiley Interscience page 654-659) and well known by those skilled in the art. The so-obtained acetylenic compounds are then transformed into compounds 4 (not shown) by reacting them with $R_3$-LG following the well known Sonogashira procedure (Science of Synthesis, H. Heaney and S. Christie, October 2003, Vol. 3, Page 402 and following), that uses cuprous iodide and a palladium complex chosen from $(Ph_3P)_2PdCl_2$, $(Ph_3P)_2Pd(OAc)_2$, $(Ph_3P)_4Pd$ (which can also be generated in situ e.g. from triphenylphosphine and $Pd(OAc)_2$) and all the other palladium complexes cited in the literature and used for this kind of reaction, in the presence of a base such as TEA, DEA, DIPEA, TMA, butylamine, piperidine. Solvents are chosen among THF, DME, DMF, DMA, EtOAc, DMSO, toluene and others suitable for the purpose of the reaction; or the same base in excess can be used as the reaction solvent. If one carries out the reaction in DMF or DME, the isolation of compounds 4 can be avoided by adding the tetrabutylammonium fluoride or tetrabutylammonium chloride directly to the reaction medium containing 3, before the coupling (Sorensen, U. S., Pombo-Villar, E. Tetrahedron 2005, 61, 2697-2703). The $R_3$ substituents are introduced using aryl or heteroaryl halides (preferred in decreasing order iodide, bromide, chloride), aryl or heteroaryl triflates, alkyl halogenides or acyl chlorides, aroyl chlorides, heteroaroyl chlorides. Triflates are synthesized using very well known method to people who have skills in the art, e.g. from phenols or hydroxyaryls (heteroaryls) using trifluoromethanesulphonic anhydride in a chlorinated solvent or using N-phenyltriflimide in toluene or a chlorinated solvent in the presence or not of a base (e.g. TEA). Both processes can be accelerated with the aid of microwaves performing the reaction in a microwave oven. Other suitable leaving groups LG for $R_3$-LG are nonaflates, tosylates and potassium trifluoborates.

Where $R_3$ is Ak an alternative procedure to Sonogashira coupling is the reaction of compounds 4 with lithium base (e.g. butyl lithium or LHDMS) in a proper solvent e.g. to produce the lithium alkinyl derivative, which on turn is reacted with a suitable electrophile like e.g. butyl iodide or the like in the same solvent or in alternative aprotic solvent like toluene at a temperature arnging from $-20°$ C. to the reflux of the chosen solvent.

If compounds 4 are obtained, where Q is a protecting group, they need further deprotection and N-arylation/alkylation or other kinds of derivatization steps to afford Compound I.

Compounds 4 can be obtained by directly reacting compounds 2 with properly derivatized propioladehyde oxime where the $R_3$ group replace the trialkylsilyl group.

Scheme 2

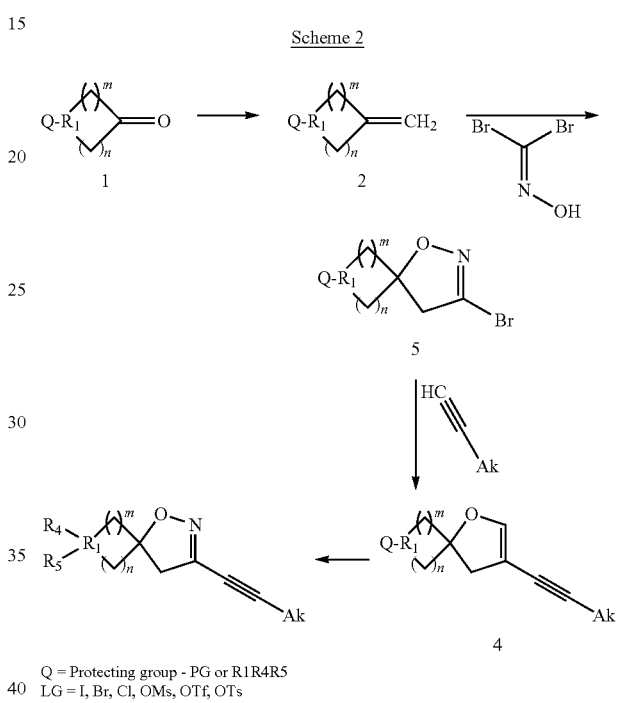

Q = Protecting group - PG or R1R4R5
LG = I, Br, Cl, OMs, OTf, OTs

In Scheme 2, "Ak" represents a lower alkyl group, and the remaining variables are as defined for the general formula I or inside the scheme itself.

Scheme 2 represents an alternative procedure to obtain compounds I where $R_3$ is Ak. Reacting dibromoformaldoxime as described above for the preparation of compounds 3, one can synthesize compounds 5. The bromooxazoline 5 can further be alkinylated by the use alkines, a proper base like sodium carbonate awith the aids of Cu/CuI co catalysis as described in details inside the experimental part. If compounds 6 are obtained, where Q is a protecting group, they need further deprotection and N-arylation/alkylation or other kinds of derivatization steps to afford Compound I.

Compounds 6 can be obtained by directly reacting compounds 2 with the proper alkylpropioladehyde oximes.

Other spiroheterocycle intermediates different from spirooxazolines can be synthesized following methods reported in the literature and cited in the experimental part as references.

The syntheses of other compounds not currently described in the general description above are well documented inside the experimental part of this invention which follows.

The free bases of formula I, their diastereomers or enantiomers can be converted to the corresponding pharmaceutically acceptable salts under standard conditions well known in the art. For example, the free base is dissolved in a suitable organic solvent, such as methanol, treated with, for example one equivalent of maleic or oxalic acid, one or two equivalents of hydrochloric acid or methanesulphonic acid, and then concentrated under vacuum to provide the corresponding pharmaceutically acceptable salt. The residue can then be purified by recrystallization from a suitable organic solvent or organic solvent mixture, such as methanol/diethyl ether.

The N-oxides of compounds of formula I can be synthesized by simple oxidation procedures well known to those skilled in the art.

EXAMPLES

The following examples represent synthesis of the compounds of Formula I as described generally above. These examples are illustrative only and are not intended to limit the scope of the invention. The reagents and starting materials are readily available to one of ordinary skill in the art.

Example 1

8-(6-Methyl-3-nitropyridin-2-yl)-3-(phenylethynyl)-1-oxa-2,8-diazaspiro[4.5]dec-2-ene 3-Phenylprop-2-ynal oxime (Compound 1a)

A mixture of phenylpropargylaldehyde (859 mg, 6.6 mmol), hydroxylamine hydrochloride (4.59 g, 66 mmol), EtOH (48 mL) and water (12 mL) was stirred at r.t. for 24 h. The reaction mixture was diluted with $H_2O$, extracted with $Et_2O$-EtOAc, washed with brine and evaporated to dryness in vacuo affording 0.96 g of the title compound (syn:anti 1:1) as a pasty brownish solid.
MS: $[M+H]^+$=146.11

Tert-butyl 3-(phenylethynyl)-1-oxa-2,8-diazaspiro[4.5]dec-2-ene-8-carboxylate (Compound 1b)

To a solution of Compound 1a (0.35 g, 2.41 mmol) in 3 mL of DMF stirred at r.t. was added N-chlorosuccinimide (0.386 g, 2.89 mmol) and the solution became orange coloured. After 2 h stirring, the solution became yellow and, after additional 2 h stirring, it was cooled to 0° C. and a solution of tert-butyl 4-methylenepiperidine-1-carboxylate (143 mg, 0.73 mmol) in 0.5 mL of DMF was added, followed by a solution of TEA in 0.5 mL of DMF. The cooling bath was removed and the reaction mixture was stirred at r.t. for 2 days. Afterwards, the reaction mixture was diluted with cold water, extracted with EtOAc. The extracts were washed with brine, dried over $Na_2SO_4$, evaporated to dryness in vacuo. The crude was purified by automated flash chromatography (SP1®TM-Biotage; gradient Petroleum Ether-EtOAc from 95:5 to 7:3) affording 210 mg of the title product. Yield: 85.5%.
MS: $[M+H]^+$=341.16

3-(Phenylethynyl)-1-oxa-2,8-diazaspiro[4.5]dec-2-ene (Compound 1c)

To a solution of Compound 1b (200 mg, 0.59 mmol) in $CH_2Cl_2$ (12 mL) stirred at 0° C. was added trifluoroacetic acid (452 µl, 5.87 mmol) and the reaction mixture was stirred at 25° C. for 24 h, until the complete conversion of the reactant was observed by LC-MS. Water was added followed by 3N aq. NaOH to give a alkaline pH. Separation of the organic layer and extraction of the aqueous layer with $CH_2Cl_2$, washing with brine and drying over $Na_2SO_4$ the combined organic layers, afforded the title compound as beige solid, used in the next step without further purification.
MS: $[M+H]^+$=241.29

8-(6-Methyl-3-nitropyridin-2-yl)-3-(phenylethynyl)-1-oxa-2,8-diazaspiro[4.5]dec-2-ene A solution of Compound 1c (50 mg, 0.21 mmol), 2-chloro-6-methyl-3-nitropyridine (39.5 mg, 0.23 mmol) and triethylamine (31.9 µL, 0.23 mmol) in N,N-dimethylacetamide (1.14 mL) was stirred at r.t. for 24 h and poured into water. The aqueous layer was extracted with EtOAc. The combined extracts were washed with water, dried over $Na_2SO_4$ and evaporated to dryness in vacuo. The crude product was purified by automated flash chromatography (SP1®TM-Biotage) eluting with a Petroleum Ether-$Me_2CO$ 95:5 mixture. A further purification with $CH_2Cl_2$ as eluent afforded 47.7 mg of the title compound (67.7%) as yellow solid.
MS: $[M+H]^+$=377.22
$^1$H-NMR: ($CDCl_3$, δ): 1.90-2.11 (m, 4H), 2.50 (s, 3H), 3.00 (s, 2H), 3.50-3.71 (m, 4H), 6.63 (d, J=8 Hz, 1H), 7.34-7.46 (m, 3H), 7.51-7.57 (m, 2H), 8.11 (d, 8 Hz, 1H).

Example 2

8-(3-Nitropyridin-2-yl)-3-(phenylethynyl)-1-oxa-2,8-diazaspiro[4.5]dec-2-ene 2-(4-Methylene-1-piperidyl)-3-nitropyridine (Compound 2a)

n-Butyllithium in hexanes (2.5 M, 4.93 mL, 12.3 mmol) was added dropwise over 10 min. into a suspension of 98% methyltriphenylphosphonium bromide (4.65 g, 12.8 mmol) in 40 mL of THF stirred at −70° C. After 0.5 h, a solution of 1-(3-nitro-2-pyridyl)-4-oxopiperidine (2 g, 8.5 mmol) in 16 mL of THF was added and the reaction mixture was allowed to warm up to r.t. After overnight resting, the mixture was quenched with an aqueous saturated solution of $NH_4Cl$, extracted with EtOAc, dried over $Na_2SO_4$, evaporated to dryness in vacuo. The crude product was purified by automated flash chromatography (SP1®TM-Biotage) eluting with a Petroleum Ether-EtOAc gradient from 1:0 to 9:1 yielding 1.23 g of the title compound as yellow solid.
MS: $[M+H]^+$=220.18

8-(3-Nitropyridin-2-yl)-3-(phenylethynyl)-1-oxa-2,8-diazaspiro[4.5]dec-2-ene

The title product was prepared as described for Compound 1b but replacing Compound 2a for tert-butyl 4-methylenepiperidine-1-carboxylate. After the usual work-up, the mixture was purified by automated flash chromatography (SP1®TM-Biotage) eluting with a Petroleum Ether-EtOAc gradient from 95:5 to 7:3 yielding 25 mg of the title compound. Yield:
MS: $[M+H]^+$=363.54
$^1$H-NMR: ($CDCl_3$, δ): 1.90-2.11 (m, 4H), 3.00 (s, 2H), 3.51-3.70 (m, 4H), 6.76-6.83 (m, 1H), 7.34-7.46 (m, 3H), 7.47-7.51 (m, 2H), 8.14-8.18 (m, 1H), 8.36-8.38 (m, 1H).

Example 3

8-(6-Methyl-3-nitropyridin-2-yl)-3-[(6-methylpyridin-2-yl)ethynyl]-1-oxa-2,8-diazaspiro[4.5]dec-2-ene

6-Methyl-2-(4-methylene-1-piperidyl)-3-nitropyridine (Compound 3a)

The title product was synthesized following the procedure reported for Compound 2a but replacing 1-(6-methyl-3-nitro-2-pyridyl)-4-oxopiperidine for 1-(3-nitro-2-pyridyl)-4-oxopiperidine. Yield: 62%.
MS: $[M+H]^+=233.12$

N-Hydroxy-3-trimethylsilyl-prop-2-ynimidoyl chloride (Compound 3b)

To a solution of 3-trimethylsilylprop-2-ynal oxime (Carreira, Erick M.; Lohse-Fraefel, Nina, Organic Letters, Volume 7, Issue 10, 2005, Pages 2011-20141, 68 g, 11.9 mmol) in 11.9 mL of DMF stirred at r.t. was added N-chlorosuccinimide (1.99 g, 14.8 mmol). After 4 h stirring, the solution was poured into water and extracted with $Et_2O$. After the usual work-up, the residue (2.09 g) was used as it was for the next step.

8-(6-Methyl-3-nitropyridin-2-yl)-3-(2-trimethylsilylethynyl)-1-oxa-2,8-diazaspiro[4.5]dec-2-ene (Compound 3c)

A solution of TEA (0.554 mL, 3.85 mmol) in 9.4 mL of dichloromethane was added dropwise into a solution of Compound 3b (1.67 g, 2.57 mmol) and Compound 3a (600 mg, 2.57 mmol) in 42 mL of dichloromethane stirred at 0° C. Afterwards, the reaction mixture was stirred at r.t. for 24 h; then it was diluted with cold water. The organic layer was washed with brine, dried over $Na_2SO_4$, evaporated to dryness in vacuo. The crude was purified by automated flash chromatography (SP1®TM-Biotage; gradient $CH_2Cl_2$-Petroleum Ether-EtOAc from 5:5 to 10:0) affording 641 mg of the title product. Yield: 67%.
MS: $[M+H]^+=273.43$

8-(6-Methyl-3-nitropyridin-2-yl)-3-[(6-methylpyridin-2-yl)ethynyl]-1-oxa-2,8-diazaspiro[4.5]dec-2-ene A suspension of Compound 3c (58 mg, 0.16 mmol), sodium acetate trihydrate (42.5 mg, 0.31 mmol), 2-bromo-6-methylpyridine (26.8 mg, 0.16 mmol), tetrabutylammonium fluoride (40.8 mg, 0.156 mmol) and tetrakis(triphenylphosphine)palladium(0) (15.8 mg, 0.014 mmol) in 2.05 ml of DMF flushed with nitrogen was heated in a microwave oven (Biotage) at 120° C. for 10 min. Dilution with EtOAc, washing with $H_2O$ and drying over $Na_2SO_4$ followed by evaporation and purification of the residue by automated flash liquid chromatography (Horizon®TM-Biotage) (Petroleum Ether-EtOAc gradient from 9:1 to 6:4) afforded 17.4 mg (28.5%) of the title compound as yellow oil.
MS: $[M+H]^+=392.33$
$^1$H-NMR: ($CDCl_3$, δ): 1.90-2.07 (m, 4H), 2.48 (s, 3H), 2.66 (s, 3H), 3.04 (s, 2H), 3.50-3.68 (m, 4H), 6.62 (d, J=8 Hz, 1H), 7.22-7.26 (m, 1H), 7.42-7.46 (m, 1H), 7.65-7.61 (m, 1H), 8.10 (d, J=8 Hz, 1H).

Example 4

8-(6-Methyl-3-nitropyridin-2-yl)-3-(thien-2-ylethynyl)-1-oxa-2,8-diazaspiro[4.5]dec-2-ene The title product was prepared replacing 2-bromothiophene for 2-bromo-6-methylpyridine following the procedure reported above for the compound of Example 3. Purification of the residue by automated flash liquid chromatography (Horizon®TM-Biotage) (Petroleum Ether-EtOAc gradient from 9:1 to 6:4). Yield: 26.7%.
MS: $[M+H]^+=383.52$

Example 5

8-(6-Methyl-3-nitropyridin-2-yl)-3-(pyridin-2-ylethynyl)-1-oxa-2,8-diazaspiro[4.5]dec-2-ene The title product was prepared replacing 2-iodopyridine for 2-bromo-6-methylpyridine following the procedure reported above for the compound of Example 3. Purification of the residue by automated flash liquid chromatography (Horizon®TM-Biotage) (Petroleum Ether-EtOAc gradient from 9:1 to 4:6). Yield: 49.6%.
MS: $[M+H]^+=378.46$
$^1$H-NMR: ($CDCl_3$, δ): 1.90-2.09 (m, 4H), 2.49 (s, 3H), 3.03 (s, 2H), 3.51-3.67 (m, 4H), 6.63 (d, J=8 Hz, 1H), 7.36-7.41 (m, 1H), 7.59-7.63 (m, 1H), 7.76-7.82 (m, 1H), 8.11 (d, J=8 Hz, 1H), 8.66-8.69 (m, 1H).

Example 6

3-[(2-Fluorophenyl)ethynyl]-8-(6-methyl-3-nitropyridin-2-yl)-1-oxa-2,8-diazaspiro[4.5]dec-2-ene The title product was prepared replacing 2-fluoroiodobenzene for 2-bromo-6-methylpyridine following the procedure reported above for the compound of Example 3. Purification of the residue by automated flash liquid chromatography (Horizon®TM-Biotage) (Petroleum Ether-EtOAc gradient from 95:5 to 7:3). Yield: 42.6%.
MS: $[M+H]^+=395.27$
$^1$H-NMR: ($CDCl_3$, δ): 1.90-2.11 (m, 4H), 2.50 (s, 3H), 3.02 (s, 2H), 3.50-3.70 (m, 4H), 6.63 (d, J=8 Hz, 1H), 7.09-7.21 (m, 2H), 7.36-7.45 (m, 1H), 7.49-7.57 (m, 1H), 8.11 (d, J=8 Hz, 1H).

Example 7

3-[(3-Fluorophenyl)ethynyl]-8-(6-methyl-3-nitropyridin-2-yl)-1-oxa-2,8-diazaspiro[4.5]dec-2-ene The title product was prepared replacing 3-fluoroiodobenzene for 2-bromo-6-methylpyridine and following the procedure reported above for the compound of Example 3. Yield: 42.4%
MS: $[M+H]^+=395.41$
$^1$H-NMR: ($CDCl_3$, δ): 1.90-2.11 (m, 4H), 2.50 (s, 3H), 2.99 (s, 2H), 3.50-3.70 (m, 4H), 6.63 (d J=8 Hz, 1H), 7.09-7.17 (m, 1H), 7.20-7.27 (m, 1H), 7.30-7.39 (m, 2H), 8.11 (d, 8 Hz, 1H).

Example 8

3-[(4-Fluorophenyl)ethynyl]-8-(6-methyl-3-nitropyridin-2-yl)-1-oxa-2,8-diazaspiro[4.5]dec-2-ene The title product was prepared replacing 4-fluoroiodobenzene for 2-bromo-6-methylpyridine, following the procedure reported above for the compound of Example 3. Yield: 37.7%

MS: [M+H]$^+$=395.27

$^1$H-NMR: (CDCl$_3$, δ): 1.90-2.10 (m, 4H), 2.50 (s, 3H), 2.99 (s, 2H), 3.50-3.70 (m, 4H), 6.63 (d J=8 Hz, 1H), 7.04-7.13 (m, 2H), 7.50-7.57 (m, 2H), 8.11 (d, J=8 Hz, 1H).

Example 9

3-(2-Furylethynyl)-8-(6-methyl-3-nitropyridin-2-yl)-1-oxa-2,8-diazaspiro[4.5]dec-2-ene The title product was prepared replacing 2-bromofuran for 2-bromo-6-methylpyridine following the procedure reported above for the compound of Example 3. Purification of the residue by automated flash liquid chromatography (Horizon®TM-Biotage) (Petroleum Ether-EtOAc gradient from 95:5 to 6:4). Yield: 12.6%.

MS: [M+H]$^+$=367.33

Example 10

8-(6-Methyl-3-nitropyridin-2-yl)-3-[(2-methyl-1,3-thiazol-4-yl)ethynyl]-1-oxa-2,8-diazaspiro[4.5]dec-2-ene The title product was prepared replacing 4-bromo-2-methylthiazole for 2-bromo-6-methylpyridine following the procedure reported above for the compound of Example 3. Purification of the residue by automated flash liquid chromatography (Horizon®TM-Biotage) (Petroleum Ether-EtOAc gradient from 9:1 to 5:5). Yield: 17.6%.

MS: [M+H]$^+$=398.35

Example 11

8-(6-Methyl-3-nitropyridin-2-yl)-3-prop-1-ynyl-1-oxa-2,8-diazaspiro[4.5]dec-2-ene

3-Ethynyl-8-(6-methyl-3-nitropyridin-2-yl)-1-oxa-2,8-diazaspiro[4.5]dec-2-ene (Compound 11a)

To a solution of Compound 3c (360 mg, 0.96 mmol) in 9 mL of THF was added tetrabutylammonium fluoride hydrate (269 mg, 0.963 mmol) and the reaction mixture was stirred at r.t. for 4 h. After overnight resting, quenching with water, extraction with EtOAc and evaporation to dryness, the crude was purified by automated flash liquid chromatography (Horizon®TM-Biotage) (Petroleum Ether-EtOAc gradient from 95:5 to 7:3), yielding 3-ethynyl-8-(6-methyl-3-nitropyridin-2-yl)-1-oxa-2,8-diaza-spiro[4.5]dec-2-ene (0.231 g, 80%).

MS: [M+H]$^+$=301.36

8-(6-Methyl-3-nitropyridin-2-yl)-3-prop-1-ynyl-1-oxa-2,8-diazaspiro[4.5]dec-2-ene Into a solution of Compound 11a (25 mg, 0.83 mmol) in THF (1.26 mL) kept under stirring at −78° C., Butyllithium in Hexane (2.5 M, 0.04 mL, 0.1 mmol) is added dropwise. After 30 min., methyl iodide (6.22 µL, 0.1 mmol) was added. The cold bath was removed and the orange solution was allowed to reach r.t. After overnight resting, it was quenched with a saturated aqueous NH$_4$Cl sol., extracted with EtOAc, washed with H$_2$O, dried on Na$_2$SO$_4$ and the solvent was evaporated to dryness in vacuo. The crude the crude was purified by automated flash liquid chromatography (Horizon®TM-Biotage) (Petroleum Ether-EtOAc gradient from 95:5 to 6:4) giving 6 mg of the title compound. Yield: 22.9%.

MS: [M+H]$^+$=315.32

Example 12

3-[(3-Chlorophenyl)ethynyl]-8-(6-methyl-3-nitropyridin-2-yl)-1-oxa-2,8-diazaspiro[4.5]dec-2-ene The title product was prepared replacing 3-chloroiodobenzene for 2-bromo-6-methylpyridine, following the procedure reported above for the compound of Example 3. Purification of the residue by automated flash liquid chromatography (Horizon®TM-Biotage) (Petroleum Ether-EtOAc gradient from 9:1 to 7:3). Yield: 55%.

MS: [M+H]$^+$=411.16

$^1$H-NMR: (CDCl$_3$, δ): 1.90-2.11 (m, 4H), 2.50 (s, 3H), 2.99 (s, 2H), 3.50-3.70 (m, 4H), 6.64 (d, J=8 Hz, 1H), 7.29-7.35 (m, 1H), 7.39-7.45 (m, 2H), 7.53 (m, 1H), 8.11 (d, 8 Hz, 1H).

Example 13

8-(6-Methyl-3-nitropyridin-2-yl)-3-[(3-methylphenyl)ethynyl]-1-oxa-2,8-diazaspiro[4.5]dec-2-ene The title product was prepared replacing 3-iodotoluene for 2-bromo-6-methylpyridine, following the procedure reported above for the compound of Example 3. Yellow solid. Yield: 59.6%

MS: [M+H]$^+$=391.42

$^1$H-NMR: (CDCl$_3$, δ): 1.91-2.11 (m, 4H), 2.37 (s, 3H), 2.51 (s, 3H), 2.99 (s, 2H), 3.52-3.70 (m, 4H), 6.64 (d, J=8 Hz, 1H), 7.20-7.27 (m, 2H), 7.29-7.38 (m, 2H), 8.12 (d, J=8 Hz, 1H).

Example 14

3-(3-Methoxyphenylethynyl)-8-(6-methyl-3-nitropyridin-2-yl)-1-oxa-2,8-diazaspiro[4.5]dec-2-ene The title product was prepared replacing 3-methoxyiodobenzene for 2-bromo-6-methylpyridine, following the procedure reported above for the compound of Example 3. Yellow solid. Yield: 41%

MS: [M+H]$^+$=407.27

$^1$H-NMR: (CDCl$_3$, δ): 1.90-2.09 (m, 4H), 2.49 (s, 3H), 3.00 (s, 2H), 3.52-3.70 (m, 4H), 3.84 (s, 3H), 6.63 (d, J=8 Hz, 1H), 6.95-7.00 (m, 1H), 7.06-7.08 (m, 1H), 7.12-7.16 (m, 1H), 7.26-7.32 (m, 1H), 8.11 (d, J=8 Hz, 1H).

Example 15

2-[8-(6-Methyl-3-nitropyridin-2-yl)-1-oxa-2,8-diazaspiro[4.5]dec-2-en-3-yl]ethynyl benzonitrile The title product was prepared replacing 3-iodobenzonitrile for 2-bromo-6-methylpyridine, following the procedure reported above for the compound of Example 3. Purification of the residue by automated flash liquid chromatography (Horizon®TM-Biotage) (Petroleum Ether-EtOAc gradient from 95:5 to 5:5). Yield: 66.5%.

MS: [M+H]$^+$=402.23

$^1$H-NMR: (CDCl$_3$, δ): 1.90-2.09 (m, 4H), 2.49 (s, 3H), 3.00 (s, 2H), 3.50-3.70 (m, 4H), 6.64 (d, J=8 Hz, 1H), 7.49-7.55 (m, 1H), 7.67-7.71 (m, 1H), 7.74-7.78 (m, 1H), 7.81-7.83 (s, 1H), 8.11 (d, J=8 Hz, 1H).

Example 16

8-(6-Methyl-3-nitropyridin-2-yl)-3-(thien-3-ylethynyl)-1-oxa-2,8-diazaspiro[4.5]dec-2-ene The title product was prepared replacing 3-bromothiophene for 2-bromo-6-methylpyridine following the procedure reported above for the compound of Example 3. Purification of the residue by automated flash liquid chromatography (Horizon™-Biotage) (Petroleum Ether-EtOAc gradient from 7:3 to 3:7). Yellow solid. Yield: 66.5%.

MS: [M+H]$^+$=383.22

$^1$H-NMR: (CDCl$_3$, δ): 1.90-2.01 (m, 4H), 2.49 (s, 3H), 2.98 (s, 2H), 3.50-3.70 (m, 4H), 6.62 (d, J=8 Hz, 1H), 7.19-7.22 (m, 1H), 7.32-7.35 (m, 1H), 7.62-7.63 (m, 1H), 8.11 (d, J=8 Hz, 1H).

Example 17

8-(6-Methyl-3-nitropyridin-2-yl)-3-(pyridin-3-ylethynyl)-1-oxa-2,8-diazaspiro[4.5]dec-2-ene The title compound was prepared following the procedure reported for the compound of Example 3, replacing 3-iodopyridine for 2-bromo-6-methylpyridine. After the usual work-up, the crude was purified by automated flash chromatography (SP1®TM-Biotage; gradient Petroleum Ether-EtOAc from 7:3 to 3:7) affording the title product as yellow solid. Yield: 66.7%.

MS: [M+H]$^+$=378.27

$^1$H-NMR: (CDCl$_3$, δ): 1.90-2.09 (m, 4H), 2.49 (s, 3H), 3.01 (s, 2H), 3.50-3.70 (m, 4H), 6.63 (d, J=8 Hz, 1H), 7.33-7.38 (m, 1H), 7.83-7.87 (m, 1H), 8.11 (d, J=8 Hz, 1H), 8.63-8.65 (m, 1H), 8.78-7.80 (s, 1H).

Example 18

8-(6-Methyl-3-nitropyridin-2-yl)-3-[3-(3-methyl-[1,2,4]oxadiazol-5-yl)phenylethynyl]-1-oxa-2,8-diazaspiro[4.5]dec-2-ene The title compound was prepared following the procedure reported for the compound of Example 3, replacing 5-(3-bromo-phenyl)-3-methyl-[1,2,4]oxadiazole for 2-bromo-6-methylpyridine. After the usual work-up, the crude was purified by automated flash chromatography (SP1®TM-Biotage; gradient Petroleum Ether-EtOAc from 95:5 to 6:4) affording the title product as yellow solid. Yield: 33.8%.

MS: [M+H]$^+$=459.11

$^1$H-NMR: (CDCl$_3$, δ): 1.92-2.11 (m, 4H), 2.50-2.52 (m, 6H), 3.01 (s, 2H), 3.52-3.70 (m, 4H), 6.64 (d, J=8 Hz, 1H), 7.54-7.59 (m, 1H), 7.72-7.76 (m, 1H), 8.10-8.17 (m, 2H), 8.29-8.31 (m, 1H).

Example 19

3-(3-Methylbut-1-ynyl)-8-(6-methyl-3-nitropyridin-2-yl)-1-oxa-2,8-diaza-spiro[4.5]dec-2-ene 3-Bromo-8-(6-methyl-3-nitro-2-pyridyl)-1-oxa-2.8-diazaspiro[4.5]dec-2-ene (Compound 19a)

A suspension of 1-(6-methyl-4-methylen-3-nitro-2-pyridyl)piperidine (Compound 3a, 350 mg, 1.5 mmol), sodium carbonate (1.26 g, 15 mmol) and dibromoformaldoxime (608 mg, 3 mmol) in 25 mL of EtOAc was stirred at r.t. for 2 days. Afterwards, the reaction mixture was washed with water, dried over sodium sulphate and evaporated to dryness in vacuo. The crude was purified by automated flash chromatography (SP1®TM-Biotage; gradient Petroleum Ether-EtOAc from 9:1 to 6:4) giving 377 mg of the title product. Yield: 70.8%.

MS: [M+H]$^+$=356.41

3-(3-Methylbut-1-ynyl)-8-(6-methyl-3-nitro-pyridin-2-yl)-1-oxa-2,8-diaza-spiro[4.5]dec-2-ene A mixture of Compound 19a (50 mg, 0.141 mmol), 3-methyl-1-butyne (48 mg, 0.705 mmol), sodium carbonate (74.6 mg, 0.704 mmol) and Cu (44.8 mg, 0.705 mmol) was heated in a sealed vessel at 120° C. for 32 h, adding every 8 h additional equal amounts of amounts of 3-methyl-1-butyne, sodium carbonate and Cu. Afterwards, the mixture was cooled, added with CH$_2$Cl$_2$, filtered on celite and evaporated to dryness in vacuo. The residue was purified by automated flash chromatography (SP1®TM-Biotage; gradient Petroleum Ether-EtOAc from 95:5 to 75:25 then isocratic Petroleum Ether-EtOAc from 9:1 giving 16 mg of the title product. Yield: 33.1%.

MS: [M+H]$^+$=343.20

$^1$H-NMR: (CDCl$_3$, δ): 1.26 (d, 6H, J=8 Hz), 1.86-2.05 (m, 4H), 2.49 (s, 3H), 2.73-2.81 (m, 1H), 2.86 (s, 2H), 3.48-3.65 (m, 4H), 6.62 (d, J=8 Hz, 1H), 8.10 (d, J=8 Hz, 1H).

Example 20

3-Hex-1-ynyl-8-(6-methyl-3-nitropyridin-2-yl)-1-oxa-2,8-diazaspiro[4.5]dec-2-ene The title product was synthesized following the method described for the compound of Example 19, but replacing hex-1-yne for 3-methyl-1-butyne. The residue was purified by automated flash chromatography (SP1®TM-Biotage; gradient Petroleum Ether-EtOAc from 95:5 to 85:15) giving 7.8 mg of the title product. Yield: 27.9%.

MS: [M+H]$^+$=357.27

$^1$H-NMR: (CDCl$_3$, δ): 0.95-0.99 (m, 3H), 1.26-1.65 (m, 4H), 1.86-2.03 (m, 4H), 2.38-2.45 (m, 2H), 2.48 (s, 3H), 2.86 (s, 2H), 3.48-3.65 (m, 4H), 6.61 (d, J=8 Hz, 1H), 8.10 (d, 8 Hz, 1H).

Example 21

2-{[8-(6-Methyl-3-nitropyridin-2-yl)-1-oxa-2,8-diazaspiro[4.5]dec-2-en-3-yl]-ethynyl}benzonitrile The title compound was prepared following the procedure reported for the compound of Example 3, replacing 2-bromobenzonitrile for 2-bromo-6-methylpyridine. After the usual work-up, the crude was purified by automated flash chromatography (SP1®TM-Biotage; gradient Petroleum Ether-EtOAc from 9:1 to 4:6) affording the title product as yellow oil. Yield: 74.8%.

MS: [M+H]$^+$=402.08

$^1$H-NMR: (CDCl$_3$, δ): 1.90-2.11 (m, 4H), 2.49 (s, 3H), 3.06 (s, 2H), 3.50-3.70 (m, 4H), 6.63 (d, J=8 Hz, 1H), 7.48-7.54 (m, 1H), 7.60-7.74 (m, 3H), 8.11 (d, J=8 Hz, 1H).

Example 22

3-[3-(3-Chlorophenylethynyl)-1-oxa-2,8-diazaspiro[4.5]dec-2-en-8-yl]pyrazine-2-carbonitrile tert-Butyl 3-(2-trimethylsilylethynyl)-1-oxa-2,8-diazaspiro[4.5]dec-2-ene-8-carboxylate (Compound 22a)

The title compound was synthesized following the method reported for Compound 3c substituting Compound 3a with tert-butyl 4-methylenepiperidine-1-carboxylate. After the usual work-up, the crude was purified by automated flash chromatography (SP1®TM -Biotage; gradient Petroleum Ether-EtOAc from 95:5 to 6:4) affording the title product as white solid. Yield: 43.3%.

MS: [M+H]$^+$=337.13 tert-Butyl 3-[2-(3-chlorophenyl)ethynyl]-1-oxa-2,8-diazaspiro[4.5]dec-2-ene-8-carboxylate (Compound 22b)

The title compound was synthesized following the method reported for the compound of Example 3, substituting 2-bromo-6-methylpyridine with 1-chloro-3-iodobenzene and Compound 3c with Compound 2a, with tert-butyl 4-methylenepiperidine-1-carboxylate. After the usual work-up, the crude was purified by automated flash chromatography (SP1®TM -Biotage; gradient Petroleum Ether-EtOAc from 95:5 to 6:4) affording the title product as white solid. Yield: 76.9%.

MS: [M+H]$^+$=375.14

3-[2-(3-Chlorophenyl)ethynyl]-1-oxa-2,8-diazaspiro[4.5]dec-2-ene (Compound 22c)

The title compound was synthesized following the method reported for the Compound 1c, substituting Compound 1b with Compound 22c. The crude residue was used without further purification in the next reaction. Yield: 90.4%.

MS: [M+H]$^+$=275.12

3-[3-(3-Chlorophenylethynyl)-1-oxa-2,8-diazaspiro[4.5]dec-2-en-8-yl]pyrazine-2-carbonitrile The title compound was prepared following the method described for the compound of Example 1, replacing Compound 1c with Compound 22d and 2-chloro-6-methyl-3-nitropyridine with 2-chloro-3-cyanopyrazine. Brownish dense oil. Yield: 83.3%.

MS: [M+H]$^+$=378.14

$^1$H-NMR: (CDCl$_3$, δ): 1.90-2.00 (m, 2H), 2.10-2.15 (m, 2H), 2.99 (s, 2H), 3.65-3.78 (m, 2H), 4.20-4.27 (m, 2H), 7.29-7.35 (m, 1H), 7.39-7.45 (m, 2H), 7.54 (s, 1H), 8.05 (s, 1H), 8.28 (s, 1H).

Example 23

8-(6-Methyl-3-nitropyridin-2-yl)-3-[(2-methylphenyl)ethynyl]-1-oxa-2,8-diazaspiro[4.5]dec-2-ene The title compound was prepared following the procedure reported for the compound of Example 3, replacing 2-bromotoluene for 2-bromo-6-methylpyridine. After the usual work-up procedure, the crude was purified by automated flash chromatography (SP1®TM -Biotage; gradient Petroleum Ether-EtOAc from 95:5 to 8:2) affording the title product as yellow solid. Yield: 29.6%.

MS: [M+H]$^+$=391.09

$^1$H-NMR: (CDCl$_3$, δ): 1.90-2.11 (m, 4H), 2.46-2.50 (2s, 6H), 3.01 (s, 2H), 3.50-3.70 (m, 4H), 6.63 (d J=8 Hz, 1H), 7.18-7.34 (m, 3H), 7.48-7.52 (m, 1H), 8.11 (d, J=8 Hz, 1H).

Example 24

3-[2-Chlorophenyl)ethynyl]-8-(6-methyl-3-nitropyridin-2-yl)-1-oxa-2,8-diazaspiro[4.5]dec-2-ene The title compound was prepared following the procedure reported for the compound of Example 3, but replacing 1-chloro-2-iodobenzene for 2-bromo-6-methylpyridine. After the usual work-up, the crude was purified by automated flash chromatography (SP1®TM -Biotage; gradient Petroleum Ether-EtOAc from 95:5 to 7:3) affording the title product as yellow oil. Yield: 57.2%.

MS: [M+H]$^+$=410.97

$^1$H-NMR: (CDCl$_3$, δ): 1.90-2.11 (m, 4H), 2.49 (s, 3H), 3.03 (s, 2H), 3.50-3.70 (m, 4H), 6.63 (d J=8 Hz, 1H), 7.26-7.38 (m, 2H), 7.44-7.48 (m, 1H), 7.56-7.60 (m, 1H), 8.11 (d, J=8 Hz, 1H).

Example 25

8-(6-Methyl-3-nitropyridin-2-yl)-3-(pyrazin-2-ylethynyl)-1-oxa-2,8-diazaspiro[4.5]dec-2-ene The title compound was prepared following the procedure reported for the compound of Example 3, but replacing 2-iodopyrazine for 2-bromo-6-methylpyridine. After the usual work-up, the crude was purified by automated flash chromatography (SP1®TM-Biotage; gradient Petroleum Ether-EtOAc from 8:2 to 3:7) affording the title product as yellow solid. Yield: 28.1%.

MS: [M+H]$^+$=379.22

$^1$H-NMR: (CDCl$_3$, δ): 1.93-2.11 (m, 4H), 2.51 (s, 3H), 3.03 (s, 2H), 3.51-3.71 (m, 4H), 6.64 (d J=8 Hz, 1H), 8.12 (d, J=8 Hz, 1H), 8.60 (dd, J=16 Hz, 4 Hz, 2H), 8.80 (s, 1H).

Example 26

8-(6-Methyl-3-nitropyridin-2-yl)-3-(phenylethynyl)-1-oxa-8-azaspiro[4.5]dec-3-ene Ethyl 3-hydroxy-3-(2-phenylethynyl)-1-oxa-8-azaspiro[4.5]decane-8-carboxylate (Compound 26a)

To a solution of ethyl 2-oxo-4-oxa-8-azaspiro[4.5]decane-8-carboxylate (Edwin S. C. Wu, Ronald C. Griffith, James T. Loch III, Alex Kover, Robert J. Murray, George B. Mullen, James C. Blosser, Anthony C. Machulskis, Sally A. McCreedy, *J. Med. Chem.*, 1995, 38 (9), pp 1558-1570, 82 mg, 0.362 mmol) in THF (4 mL) was added dropwise a 1M solution of phenylethynylmagnesium bromide in THF (0.724 mL, 0.724 mmol), stirring at r.t. under anhydrous nitrogen atmosphere. The reaction mixture was stirred at r.t. for 4 h, then at 60° C. for 6 h, then it was quenched with a saturated aqueous solution of ammonium chloride, extracted with EtOAc. The combined organic layers were washed with brine, dried over sodium sulphate and evaporated to dryness in vacuo. The crude was purified by automated flash chromatography (SP1®TM-Biotage; gradient Petroleum Ether-EtOAc from 75:25 to 4:6) affording the title product as yellow solid. Yield: 87.2%.

MS: [M+H]$^+$=330.33

Ethyl 3-(phenylethynyl)-1-oxa-8-azaspiro[4.5]dec-3-ene-8-carboxylate (Compound 26b)

To a solution of Compound 26a (93 mg, 0.282 mmol) stirred in pyridine (4 mL) at 0° C. was added thionyl chloride (0.103 mL, 1.141 mmol) and the reaction mixture was stirred at 0° C. to r.t. for 2 h. Afterwards, it was poured into water, acidified with 1M HCl and extracted with chloroform. The organic layers were combined, washed with brine, dried over sodium sulphate and evaporated to dryness to afford a crude, which was purified by automated flash chromatography (SP1®TM-Biotage; gradient Petroleum Ether-EtOAc from 92:8 to 75:25) to give 18 mg of the title compound.

MS: [M+H]$^+$=312.34

3-(Phenylethynyl)-1-oxa-8-azaspiro[4.5]dec-3-ene (Compound 26c)

A mixture of Compound 26c (25 mg, 0.803 mmol), KOH (80 mg, 1.43 mmol), water (2 mL) and MeOH (4 mL) was stirred at reflux for 2 h. Afterwards it was extracted with EtOAc. The organic layer was washed with brine, dried over sodium sulphate and evaporated to dryness in vacuo. The crude residue (19.2 mg) was used without any kind of purification in the next step.

MS: [M+H]$^+$=240.10

8-(6-Methyl-3-nitropyridin-2-yl)-3-(phenylethynyl)-1-oxa-8-azaspiro[4.5]dec-3-ene The title compound was prepared following the method described for the compound of Example 1, replacing Compound 1c with Compound 26c. The crude was purified by automated flash chromatography (SP1®TM-Biotage; gradient Petroleum Ether-EtOAc from 98:2 to 9:1) to give 8 mg of the title compound. Yield: 51%

MS: [M+H]$^+$=376.14

$^1$H-NMR: (CDCl$_3$, δ): 1.75-1.87 (m, 2 H), 1.87-1.98 (m, 2 H), 2.48 (s, 3 H), 3.49 (ddd, J=13.39, 10.70, 3.06 Hz, 2 H), 3.68 (dt, J=13.45, 4.16 Hz, 2 H), 4.76 (d, J=2.20 Hz, 2 H), 6.13 (t, J=2.20 Hz, 1 H), 6.58 (d, J=8.31 Hz, 1 H), 7.32-7.40 (m, 3 H), 7.43-7.50 (m, 2 H), 8.08 (d, J=8.07 Hz, 1 H).

Example 27

3-[(3-Chlorophenyl)ethynyl]-7-(6-methyl-3-nitropyridin-2-yl)-1-oxa-2,7-diazaspiro[4.4]non-2-ene tert-Butyl 3-methylenepyrrolidine-1-carboxylate (Compound 27a)

The title compound was synthesised following the method described here for Compound 2a using 1-Boc-3-pyrrolidinone instead of 1-(3-nitro-2-pyridyl)-4-oxopiperidine. After the usual work-up procedure, the crude product was purified by automated flash chromatography (Horizon®TM-Biotage) eluting with a Petroleum Ether-EtOAc gradient from 95:5 to 7:3, yielding the title compound as brownish oil. Yield: 75.8%.

MS: [M+H]$^+$=184.53 tert-Butyl 3-(2-trimethylsilylethynyl)-1-oxa-2,7-diazaspiro[4.4]non-2-ene-7-carboxylate (Compound 27b)

The title compound was synthesised following the method described here for Compound 3c using Compound 27a instead of Compound 3a. After the usual work-up procedure, the crude product was purified by automated flash chromatography (Horizon®TM-Biotage) eluting with a Petroleum Ether-EtOAc gradient from 95:5 to 75:25 yielding the title compound. Yield: 82.9%.

MS: [M+H]$^+$=323.45

Tert-butyl 3-[(3-chlorophenyl)ethynyl]-1-oxa-2,7-diazaspiro[4.4]non-2-ene-7-carboxylate (Compound 27c)

The title compound was prepared following the procedure reported for the compound of Example 3, but replacing 1-chloro-3-iodobenzene for 2-bromo-6-methylpyridine. After the usual work-up, the crude was purified by automated flash chromatography (SP1®TM -Biotage; gradient Petroleum Ether-EtOAc from 95:5 to 6:4) affording the title product as yellow oil. Yield: 14%.

MS: [M+H]$^+$=361.13

3-[(3-Chlorophenyl)ethynyl]-1-oxa-2,7-diazaspiro[4.4]non-2-ene (Compound 27d)

The title compound was synthesized following the method reported for the Compound 1c, substituting Compound 1b with Compound 27c. The crude residue was used without further purification in the next reaction.

MS: [M+H]$^+$=261.11

3-[(3-Chlorophenyl)ethynyl]-7-(6-methyl-3-nitropyridin-2-yl)-1-oxa-2,7-diazaspiro[4.4]non-2-ene The title compound was prepared following the method described for the compound of Example 1, substituting Compound 1c with Compound 27d. The crude was purified by automated flash chromatography (SP1®TM-Biotage; gradient Petroleum Ether-Acetone from 95:5 to 9:1) to give the title compound as a dense yellow oil. Yield: 68.5%.

$^1$H-NMR: (CDCl$_3$, δ): 2.13-2.25 (m, 1 H), 2.46 (dd, J=12.84, 6.48 Hz, 1 H), 2.52 (s, 3 H), 3.17-3.34 (m, 2 H), 3.42 (d, J=12.47 Hz, 1 H), 3.69 (t, J=9.78 Hz, 1H), 3.82 (d, J=12.47 Hz, 1H), 3.98 (td, J=10.94, 6.97 Hz, 1 H), 6.61 (d, J=8.07 Hz, 1 H), 7.30-7.36 (m, 1 H), 7.37-7.45 (m, 2 H), 7.53 (s, 1 H), 8.07 (d, J=8.31 Hz, 1 H).

Example 28

7-[(3-Chlorophenyl)ethynyl]-2-(6-methyl-3-nitropyridin-2-yl)-5-oxa-2,6-diazaspiro[3.4]oct-6-ene tert-Butyl 3-methyleneazetidine-1-carboxylate (Compound 28a)

To a suspension of methyltriphenylphosphonium bromide (1.56 g, 4.37 mmol) in 30 mL of Et$_2$O stirred at 0° C. was added potassium tert-butylate (0.459 g, 4.09 mmol). After 0.5 h the cold bath was removed and the mixture was stirred for 1 h at r.t. Afterwards, it was cooled off in water-ice bath, and 3-oxo-azetidine-1-carboxylic acid tert-butyl ester (500 mg, 2.92 mmol) was added. The cold bath was removed. After overnight resting, the reaction mixture was quenched with a saturated solution of $NH_4Cl$ in water, extracted with $Et_2O$, dried on $Na_2SO_4$, evaporated to dryness in vacuo, dissolvent. The residual crude was purified by automated flash chromatography (SP1®TM-Biotage; gradient Petroleum Ether-Acetone from 10:0 to 7:3) to give the title compound (426 mg) as a dense colourless oil. Yield: 86.2%

MS: $[M+H]^+$=170.45 tert-Butyl 7-(2-trimethylsilylethynyl)-5-oxa-2,6-diazaspiro[3.4]oct-6-ene-2-carboxylate (Compound 28b)

The title compound was synthesised following the method described here for Compound 3c, using Compound 28a instead of Compound 3a. After the usual work-up procedure, the crude product was purified by automated flash chromatography (Horizon®TM-Biotage) eluting with a Petroleum Ether-EtOAc gradient from 95:5 to 6:4, yielding the title compound. Yield: 62%.

MS: $[M+H]^+$=309.16 tert-Butyl 7-[(3-chlorophenyl)ethynyl]-5-oxa-2,6-diazaspiro[3.4]oct-6-ene-2-carboxylate (Compound 28c)

The title compound was prepared following the procedure reported for the compound of Example 3, but replacing 1-chloro-3-iodobenzene for 2-bromo-6-methylpyridine. After the usual work-up, the crude was purified by automated flash chromatography (SP1®TM -Biotage; gradient Petroleum Ether-EtOAc from 8:2 to 65:35) affording the title product as yellow oil. Yield: 24.3%.

MS: $[M+H]^+$=347.09

7-[(3-Chlorophenyl)ethynyl]-5-oxa-2,6-diazaspiro[3.4]oct-6-ene (Compound 28d)

The title compound was synthesized following the method reported for the Compound 1c, substituting Compound 1b with Compound 27c. The crude residue was used without further purification in the next reaction step.

MS: $[M+H]^+$=247.13

7-[(3-Chlorophenyl)ethynyl]-2-(6-methyl-3-nitropyridin-2-yl)-5-oxa-2,6-diazaspiro[3.4]oct-6-ene The title compound was prepared following the method described for the compound of Example 1, replacing Compound 1c with Compound 28c. The crude was purified by automated flash chromatography (SP1®TM-Biotage; Petroleum Ether-Dichloromethane 1:9) to give the title compound as a dense yellow oil. Yield: 68.5%

MS: $[M+H]^+$=383.08

$^1$H-NMR: ($CDCl_3$, J): 2.51 (s, 3 H), 3.49 (s, 2 H), 4.38 (d, J=10.76 Hz, 2 H), 4.49 (d, J=11.00 Hz, 2 H), 6.65 (d, J=8.31 Hz, 1 H), 7.33 (t, J=8.10 Hz, 1 H), 7.42 (t, J=8.07 Hz, 2 H), 7.54 (s, 1 H), 8.17 (d, J=8.31 Hz, 1 H).

Example 29 and 30

9-(6-Methyl-3-nitropyridin-2-yl)-4-(2-phenylethynyl)-1-oxa-9-azaspiro[5.5]undec-4-ene and

9-(6-Methyl-3-nitropyridin-2-yl)-4-(2-phenylethynyl)-1-oxa-9-azaspiro[5.5]undec-3-ene tert-Butyl 4-methylene-1-oxa-9-azaspiro[5.5]undecane-9-carboxylate (Compound 29a)

To a solution of 1-Boc-piperidone (2.39 g, 12 mmol) and ethoxytrimethylsilane (3.75 mL, 24 mmol) in 80 mL of $CCl_4$ under stirring at 0° C. was added trimethylsilyl trifluoromethylsulfonate (217 µL, 1.2 mmol) and trimethyl-(2-methylene-4-trimethylsilyloxybutyl)silane (E. I. Marko et al., Journal of Organic Chemistry 1992, 57, 2211-2213) dissolved in in 23 mL of $CCl_4$. After stirring at 0-5° C. for 6 h and overnight resting at 0° C., the reaction mixture was washed with water, dried on $Na_2SO_4$, filtered and the solvent was evaporated to dryness in vacuo. The residual 6.5 g of colourless oil was purified by means of automated flash chromatography (SP1®TM-Biotage; Petroleum Ether-EtOAc gradient from 99:1 to 85:15) to give 3.2 g of the title compound as colourless oil. Yield: 1000%

MS: $[M+H]^+$=268.62 tert-Butyl 4-oxo-1-oxa-9-azaspiro[5.5]undecane-9-carboxylate (Compound 29b)

To a solution of Compound 29a (1.6 g, 5.99 mmol) in a mixture of dioxane-water (32.9 mL and 11 mL respectively) under stirring at r.t. was added a 4% sol. of osmium tetroxide in water (0.762 µL, 0.125 mmol). After 2 h, was added portionwise milled sodium metaperiodate (2.56 g, 12 mmol) affording a suspension that tended to become clear gray from brownish. After 4 h $H_2O$ was added, extracting with EtOAc, washing with $H_2O$, drying over $Na_2SO_4$, evaporating the solvent to dryness. The residual tawny semi-solid was purified by means of automated flash chromatography (SP1®TM-Biotage; Petroleum Ether-EtOAc 7:3) to give 0.96 g of the title compound as a grey solid. Yield: 59.5%

MS: $[M+H]^+$=270.33 tert-Butyl 4-hydroxy-4-(2-phenylethynyl)-1-oxa-9-azaspiro[5.5]undecane-9-carboxylate (Compound 29c)

The title compound was prepared following the method reported here for Compound 26a, substituting ethyl 2-oxo-4-oxa-8-azaspiro[4.5]decane-8-carboxylate with Compound 29b. After the usual work-up procedure the oily residue was purified by means of automated flash chromatography (SP1®TM-Biotage; Petroleum Ether-EtOAc gradient 9:1 to 6:4) to give 0.96 g of the title compound as a grey solid. Yield: 57.3%

MS: $[M+H]^+$=372.14

4-(Phenylethynyl)-1-oxa-9-azaspiro[5.5]undec-3-ene and 4-(Phenylethynyl)-1-oxa-9-azaspiro[5.5]undec-4-ene (Compounds 29d)

The title compounds was prepared following the method reported here for Compound 26c, substituting Compound 26b with Compound 29c. After the usual work-up procedure, the residual oil was purified by means of automated flash chromatography (SP1®TM-Biotage; Petroleum Ether-EtOAc gradient 9:1 to 8:2) to give 0.49 g (33.6%) of the title compounds, used in the next step without separating them as a brownish oil.

MS: [M+H]⁺=254.17

9-(6-Methyl-3-nitropyridin-2-yl)-4-(2-phenylethynyl)-1-oxa-9-azaspiro[5.5]undec-4-ene and

9-(6-Methyl-3-nitropyridin-2-yl)-4-(2-phenylethynyl)-1-oxa-9-azaspiro[5.5]undec-3-ene The title compound was prepared following the method described for the compound of Example 1, replacing Compound 1c with Compound 29d. The crude was purified by automated flash chromatography (SP1®TM-Biotage; gradient Petroleum Ether-$CH_2Cl_2$ from 4:6 to 3:7) to give 5 mg of the compound of Example 29 and 1 mg of the compound of Example 30.

Example 29

MS: [M+H]⁺=390.29
¹H-NMR (CDCl₃, δ): 1.73-1.90 (m, 4 H), 2.32-2.39 (m, 2 H), 2.47 (s, 3 H), 3.38-3.50 (m, 2 H), 3.60-3.72 (m, 2 H), 3.87 (t, J=5.38 Hz, 2 H), 6.07 (s, 1H), 6.57 (d, J=8.31 Hz, 1 H), 7.30-7.37 (m, 3H), 7.42-7.50 (m, 2 H), 8.08 (d, J=8.07 Hz, 1 H).

Example 30

MS: [M+H]⁺=390.16
¹H-NMR: (CDCl₃, δ): 1.69-1.79 (m, 2 H), 1.95 (d, J=13.20 Hz, 2 H), 2.26 (d, J=1.96 Hz, 2 H), 2.48 (s, 3 H), 3.36-3.50 (m, 2 H), 3.58-3.70 (m, 2 H), 4.30 (d, J=2.69 Hz, 2 H), 6.20 (br. s., 1 H), 6.58 (d, J=8.31 Hz, 1 H), 7.31-7.41 (m, 3 H), 7.45 (dd, J=6.60, 2.93 Hz, 2 H), 8.08 (d, J=8.31 Hz, 1 H).

Example 31

3-[(3-Chlorophenyl)ethynyl]-1,9,12-trioxa-2-aza-dispiro[4.2.4.2]tetradec-2-ene

8-Methylene-1,4-dioxaspiro[4.5]decane (Compound 31a)

The title compound was prepared following the method reported here for Compound 2a, but using lithium-bis-trimethylsilylamide instead of buthyl lithium and carrying out the reaction at −20° C. As starting material 1,4-dioxaspiro[4.5] decan-8-one replaced 1-(3-nitro-2-pyridyl)-4-oxopiperidine. After the usual work-up procedure the residue was purified by means of automated flash chromatography (Horizon®TM-Biotage; Petroleum Ether EtOAc 95:5) to give the title compound as fluid colourless oil. Yield: 99.3%.

MS: [M+H]⁺=155.13

3-(2-Trimethylsylylethynyl)-1,9,12-trioxa-2-aza-dispiro[4.2.4.2]tetradec-2-ene (Compound 31b)

The title compound was synthesized using the method reported here for Compound 3c, but replacing Compound 31a for Compound 3a. After the usual work-up procedure the residue was purified by means of automated flash chromatography (Horizon®TM -Biotage; gradient Petroleum Ether-EtOAc from 98:2 to 9:1) to give the title compound.

3-[(3-Chlorophenyl)ethynyl]-1,9,12-trioxa-2-aza-dispiro[4.2.4.2]tetradec-2-ene The title compound was prepared following the method reported here for the compound of Example 3, but replacing 1-chloro-3-iodobenzene for 2-bromo-6-methylpyridine. After the usual work-up procedure, the residue was purified by means of automated flash chromatography (Horizon®TM-Biotage; Petroleum Ether-EtOAc 85:15) to give the title compound as a grey solid. Yield: 80.1%.
Alternative Procedure:

1-Chloro-3-(3,3-diethoxyprop-1-ynyl)benzene (compound 31c)

A mixture of 1-chloro-3-iodobenzene (4 g, 16.8 mmol), propargylaldehyde diethyl acetal (2.66 mL, 18.5 mmol), bis(trifenilphosphine)palladium(II)dichloride (295 mg, 0.42 mmol), cuprous iodide (160 mg, 0.84 mmol) and triethylamine (60 mL) was stirred at r.t. for 3 h. After 4 h, the reaction mixture was quenched with $H_2O$, extracted with EtOAc, which was washed with brine, dried over $Na_2SO_4$, and evaporated to dryness in vacuo. The residue was purified by automated flash chromatography (Horizon®TM-Biotage; Petroleum Ether-EtOAc 97:3) to give 4 g of the title compound as a fluid yellowish oil. Yield: 100%.

MS: [M+H]⁺=239.32

3-(3-chlorophenyl)prop-2-ynal (Compound 31d)

A solution of Compound 31c (4 g, 16.7 mmol) in $CH_2Cl_2$ was added with 38.8 mL of water and 7.7 mL of trifluoroacetic acid. After 4 h under stirring, further 4 eq. of trifluoroacetic acid was added. After 24 h, the conversion was completed, the 2 layers were separated, the organic layer was washed with water, dried over $Na_2SO_4$ and evaporated to dryness in vacuo, to afford the title compound as yellow-brownish oil, used in the next step without further purification.

MS: [M+H]⁺=165.35

3-(3-Chlorophenyl)prop-2-ynal oxime (Compound 31e)

The title compound was prepared following the method here described for Compound 1a, using Compound 31d instead of phenylpropiolaldehyde. The pale brown residue was used in the next step without further purification. Yield: 96.4%.

MS: [M+H]⁺=180.16

3-(3-Chlorophenyl)-N-hydroxy-prop-2-ynimidoyl chloride (Compound 31J)

The title compound was prepared following the method herein described for Compound 3b, using Compound 31e instead of 3-trimethylsilylprop-2-ynal oxime. The pale brown residue was used in the next step without further purification. Yield: 96.4%.

3-[(3-Chlorophenyl)ethynyl]-1,9,12-trioxa-2-aza-dispiro[4.2.4.2]tetradec-2-ene The title compound was prepared following the procedure described for Compound 3c, using Compound 31f instead of Compound 3b and Compound 31a instead of Compound 3a. After the usual work-up procedure, the residue was purified by means of automated flash chromatography (Horizon®TM-Biotage; gradient Petroleum Ether-Acetone from 95:5 to 9:1) to give the title compound as a grey solid. Yield: 64.8%

MS: [M+H]$^+$=332.14

$^1$H-NMR: (CDCl$_3$, δ): 1.63-1.74 (m, 2 H), 1.88 (dd, J=13.94, 2.45 Hz, 2 H), 1.96-2.10 (m, 4 H), 2.92 (s, 2 H), 3.92-4.05 (m, 4 H), 7.32 (d, J=7.58 Hz, 1 H), 7.35-7.44 (m, 2 H), 7.52 (s, 1 H)

Example 32

3-[(3-Chlorophenyl)ethynyl]-1-oxa-2-azaspiro[4.5]dec-2-en-8-one

A solution of the compound of Example 31 (0.76 g, 2.3 mmol) in 5 mL of trifluoroacetic acid was diluted with water (0.21 mL) and stirred at 0-4° C. for 4 h, alkalinized with 3N NaOH, extracted with EtOAc, washed with water, dried over Na$_2$SO$_4$ and evaporated to dryness in vacuo to afford the title compound as yellow-brownish oil. The residue was purified by means of automated flash chromatography (Horizon®TM-Biotage; Petroleum Ether-EtOAc 8:2) to give the title compound as a grey solid. Yield: 53.8%

MS: [M+H]$^+$=288.14

$^1$H-NMR: (CDCl$_3$, δ): 1.99-2.10 (m, 2 H), 2.28-2.44 (m, 4 H), 2.78-2.90 (m, 2 H), 3.03 (s, 2 H), 7.33 (t, J=7.60 Hz, 1 H), 7.38-7.46 (m, 2 H), 7.53 (s, 1 H).

Example 33

3-[(3-Chlorophenyl)ethynyl]-8-methylene-1-oxa-2-azaspiro[4.5]dec-2-ene

The title compound was synthesized using the same methodology described for Compound 31a, but starting from the compound of Example 32 instead of 1,4-dioxaspiro[4.5]decan-8-one. After the usual work-up procedure, the residue was purified by means of automated flash chromatography (Horizon®TM-Biotage; gradient Petroleum Ether-Acetone EtOAc from 95:5 to 9:1) to give the title compound as a grey solid. Yield: 67.3%

MS: [M+H]$^+$=286.14

$^1$H-NMR: (CDCl$_3$, δ): 1.64-1.78 (m, 2 H) 1.93-2.06 (m, 2 H), 2.16-2.25 (m, 2 H), 2.50 (ddd, J=13.75, 9.60, 4.52 Hz, 2 H), 2.93 (s, 2 H), 4.74 (s, 2 H), 7.29-7.34 (m, 1 H), 7.35-7.43 (m, 2 H), 7.47-7.57 (m, 1 H).

Example 34

3-[(3-Chlorophenyl)ethynyl]-1-oxa-2-azaspiro[4.5]dec-2-en-8-one O-methyloxime

A mixture of the compound of Example 31 (80 mg, 0.28 mmol), O-methyl hydroxylamine hydrochloride (30.2 g, 0.361 mmol), MeOH (12 mL) and triethylamine (58 μL, 0.42 mmol) was stirred at r.t. for 12 h. The reaction mixture was diluted with H2O, extracted with EtOAc, washed with brine, dried over sodium sulphate and evaporated to dryness in vacuo. The residue was purified by means of automated flash chromatography (Horizon®TM-Biotage; gradient Petroleum Ether-EtOAC from 9:1 to 8:2) to give 56 mg of the title compound as yellow oil. Yield: 63.6%

MS: [M+H]$^+$=317.18

$^1$H-NMR: (CDCl$_3$, δ): 1.70-1.89 (m, 2 H), 2.04-2.20 (m, 2 H), 2.34 (dt, J=14.37, 4.68 Hz, 1H), 2.48 (ddd, J=14.92, 11.25, 5.38 Hz, 1 H), 2.61 (ddd, J=14.49, 11.31, 5.01 Hz, 1 H), 2.88-2.94 (m, 1 H), 2.95 (s, 2 H), 3.86 (s, 3 H), 7.29-7.35 (m, 1 H), 7.36-7.44 (m, 2 H), 7.51-7.54 (m, 1 H).

Example 35

7-(6-Methyl-3-nitropyridin-2-yl)-3-[(6-methylpyridin-2-yl)ethynyl]-1-oxa-2,7-diazaspiro[4.4]non-2-ene tert-Butyl 3-[(6-methylpyridin-2-yl)ethynyl]-1-oxa-2,7-diazaspiro[4.4]non-2-ene-7-carboxylate (Compound 35a)

The title compound was prepared following the procedure reported for the compound of Example 3, but replacing Compound 27b for Compound 3c. After the usual work-up, the crude was purified by automated flash chromatography (SP1®TM-Biotage; gradient Petroleum Ether-EtOAc from 75:25 to 40:60) affording the title product as colourless oil. Yield: 66.2%.

MS: [M+H]$^+$=342.51

3-[(6-Methylpyridin-2-yl)ethynyl]-1-oxa-2,7-diazaspiro[4.4]non-2-ene (Compound 35b)

The title compound was synthesized following the method reported for the Compound 1c, substituting Compound 1b with Compound 35a and running the reaction in chloroform. The crude brownish oily residue was used without further purification in the next reaction step. Yield: 94.5%.

MS: [M+H]$^+$=242.33

7-(6-Methyl-3-nitropyridin-2-yl)-3-[(6-methylpyridin-2-yl)ethynyl]-1-oxa-2,7-diazaspiro[4.4]non-2-ene The title compound was prepared following the method described for the compound of Example 1, replacing Compound 1c with Compound 35b. The crude was purified by automated RP chromatography (SP1®TM-Biotage; gradient MeCN—H$_2$O from 4:6 to 7:3) to give the title compound as yellow solid. Yield: 41.5%.

MS: [M+H]$^+$=378.62

$^1$H-NMR: (CDCl$_3$, δ): 2.17 (d, 1H), 2.43 (dd, 1 H), 2.49 (s, 3 H), 2.63 (s, 3 H), 3.21-3.35 (m, 2 H), 3.42 (d, 1H), 3.63 (t, 1 H), 3.79 (d, 1H), 3.97 (m, 1H), 6.59 (d, 1H), 7.22 (d, 1H), 7.41 (d, 1H), 7.65 (t, 1H), 8.05 (d, 1H).

Example 36

7-(6-Methyl-3-nitropyridin-2-yl)-3-(phenylethynyl)-1-oxa-2,7-diazaspiro[4.4]non-2-ene tert-Butyl 3-(phenylethynyl)-1-oxa-2,7-diazaspiro[4.4]non-2-ene-7-carboxylate (Compound 36a)

The title compound was prepared following the procedure reported for the compound of Example 3, but replacing Compound 27b for Compound 3c and iodobenzene for 2-bromo-6-methylpyridine. After the usual work-up, the crude was purified by automated flash chromatography (SP1®TM-Biotage; gradient Petroleum Ether-EtOAc from 95:5 to 60:40) affording the title product as colourless oil. Yield: 40.9%.

MS: [M+H]$^+$=327.35

3-(Phenylethynyl)-1-oxa-2,7-diazaspiro[4.4]non-2-ene (Compound 36b)

The title compound was synthesized following the method reported for the Compound 1c, substituting Compound 1b with Compound 36a and running the reaction in chloroform. The crude brownish oily residue was used without further purification in the next reaction step. Yield: 91.3%.
MS: [M+H]$^+$=227.33

7-(6-Methyl-3-nitropyridin-2-yl)-3-(phenylethynyl)-1-oxa-2,7-diazaspiro[4.4]non-2-ene The title compound was prepared following the method described for the compound of Example 1, replacing Compound 1c with Compound 36b. The crude was purified by automated chromatography (SP1®TM-Biotage; gradient Petroleum Ether-EtOAc from 95:5 to 70:30) to give the title, compound as yellow solid. Yield: 26.3%.
MS: [M+H]$^+$=363.44
$^1$H-NMR: (CDCl$_3$, δ): 2.12-2.23 (m, 1 H), 2.39-2.53 (m, 1 H), 2.49 (s, 3 H), 3.18-3.32 (m, 2 H), 3.40 (d, 1 H), 3.65 (dd, 1 H), 3.78 (d, 1 H), 3.96 (m, 1 H), 6.59 (d, 1 H), 7.34-7.46 (m, 3H), 7.54 (dd, 2 H), 8.05 (d, 1 H).

Example 37

3-[(3-Fluorophenyl)ethynyl]-7-(6-methyl-3-nitropyridin-2-yl)-1-oxa-2,7-diazaspiro[4.4]non-2-ene tert-Butyl 3-[(3-fluorophenyl)ethynyl]-1-oxa-2,7-diazaspiro[4.4]non-2-ene-7-carboxylate (Compound 37a)

The title compound was prepared following the procedure reported for the compound of Example 3, but replacing Compound 27b for Compound 3c and 1-fluoro-3-iodobenzene for 2-bromo-6-methylpyridine. After the usual work-up, the crude was purified by automated flash chromatography (SP1®TM-Biotage; gradient Petroleum Ether-EtOAc from 95:5 to 60:40) affording the title product as colourless oil. Yield: 46.9%.
MS: [M+H]$^+$=345.40

3-[(3-Fluorophenyl)ethynyl]-1-oxa-2,7-diazaspiro[4.4]non-2-ene (Compound 37b)

The title compound was synthesized following the method reported for the Compound 1c, substituting Compound 1b with Compound 37a and running the reaction in chloroform. The crude brownish oily residue was used without further purification in the next reaction step. Yield: 91.8%.
MS: [M+H]$^+$=245.36

3-[(3-Fluorophenyl)ethynyl]-7-(6-methyl-3-nitropyridin-2-yl)-1-oxa-2,7-diazaspiro[4.4]non-2-ene The title compound was prepared following the method described for the compound of Example 1, replacing Compound 1c with Compound 37b. The crude was purified by automated RP chromatography (SP1®TM-Biotage; gradient MeCN-ammonium carbonate buffer from 4:6 to 7:3) to give the title compound as yellow solid. Yield: 74.9%.
MS: [M+H]$^+$=381.54
$^1$H-NMR: (CDCl$_3$, δ): 2.13-2.25 (m, 1 H), 2.45 (dd, 1 H), 2.52 (s, 3 H), 3.18-3.33 (m, 2 H), 3.41 (d, 1 H), 3.64-3.73 (m, 1 H), 3.81 (d, 1 H), 3.98 (t, 1 H), 6.61 (d, 1 H), 7.10-7.17 (m, 1 H) 7.21-7.27 (m, 1 H), 7.30-7.40 (m, 2 H), 8.07 (d, 1 H).

Example 38

2-(6-Methyl-3-nitropyridin-2-yl)-7-(phenylethynyl)-5-oxa-2,6-diazaspiro[3.4]oct-6-ene tert-Butyl 7-(phenylethynyl)-5-oxa-2,6-diazaspiro[3.4]oct-6-ene-2-carboxylate (Compound 38a)

The title compound was prepared following the procedure reported for the compound of Example 3, but replacing Compound 28b for Compound 3c and 1-iodobenzene for 2-bromo-6-methylpyridine. After the usual work-up, the crude was purified by automated flash chromatography (SP1®TM-Biotage; gradient Petroleum Ether-EtOAc from 8:2 to 65:35) affording the title product as colourless oil. Yield: 28.7%.
MS: [M+H]$^+$=313.36

7-(Phenylethynyl)-5-oxa-2,6-diazaspiro[3.4]oct-6-ene (Compound 38b)

The title compound was synthesized following the method reported for Compound 1c, substituting Compound 1b with Compound 38a and running the reaction in chloroform. The crude brownish oily residue was used without further purification in the next reaction step. Yield: 100%.
MS: [M+H]$^+$=213.25

2-(6-Methyl-3-nitropyridin-2-yl)-7-(phenylethynyl)-5-oxa-2,6-diazaspiro[3.4]oct-6-ene The title compound was prepared following the method described for the compound of Example 1, replacing Compound 1c with Compound 37b. The crude was purified by automated flash chromatography (SP1®TM-Biotage; gradient Petroleum Ether-EtOAc from 1:0 to 7:3) to give the title compound as yellow oil. Yield: 20.9%.
MS: [M+H]$^+$=349.36
$^1$H-NMR: (CDCl$_3$, δ): 2.50 (s, 3 H), 3.49 (s, 2 H), 4.38 (d, J=10.76 Hz, 2 H), 4.49 (d, J=11.00 Hz, 2 H), 6.64 (d, J=8.31 Hz, 1 H), 7.34-7.48 (m, 3 H), 7.55 (d, J=6.60 Hz, 2 H), 8.17 (d, J=8.31 Hz, 1 H).

Example 39

3-{[7-(6-Methyl-3-nitropyridin-2-yl)-1-oxa-2,7-diazaspiro[4.4]non-2-en-3-yl]ethynyl}phenol tert-Butyl 3-[(3-hydroxyphenyl)ethynyl]-1-oxa-2,7-diazaspiro[4.4]non-2-ene-7-carboxylate (Compound 39a)

The title compound was prepared following the procedure reported for the compound of Example 3, but replacing Compound 27b for Compound 3c and 3-iodophenol for 2-bromo-6-methylpyridine. After the usual work-up, the crude was purified by automated flash chromatography (SP1®TM-Biotage; gradient Petroleum Ether-EtOAc from 95:5 to 60:40) affording the title product as colourless oil. Yield: 31.4%.
MS: [M+H]$^+$=343.51

3-(1-Oxa-2,7-diazaspiro[4.4]non-2-en-3-ylethynyl)phenol (Compound 39b)

The title compound was synthesized following the method reported for the Compound 1c, substituting Compound 1b with Compound 39a and running the reaction in chloroform. The crude brownish oily residue was used without further purification in the next reaction step. Yield: 84.8%.

MS: [M+H]$^+$=243.28

3-{[7-(6-Methyl-3-nitropyridin-2-yl)-1-oxa-2,7-diazaspiro[4.4]non-2-en-3-yl]ethynyl}phenol The title compound was prepared following the method described for the compound of Example 1, replacing Compound 1c with Compound 39b. The crude was purified by automated RP chromatography (SP1®TM-Biotage; gradient MeCN-ammonium carbonate buffer from 4:6 to 7:3) to give the title compound as yellow solid. Yield: 42.6%.

MS: [M+H]$^+$=379.40

$^1$H-NMR: (CDCl$_3$, δ): 2.18 (dd, 1 H), 2.45 (dd, 1H), 2.51 (s, 3H), 3.17-3.33 (m, 2 H), 3.40 (d, 1H), 3.67 (t, 1H), 3.80 (d, 1H), 3.98 (t, 1H), 6.60 (d, 1H), 6.87-6.95 (m, 1H), 6.97-7.03 (m, 1 H), 7.12 (d, 1H), 7.21-7.31 (m; 1 H), 8.06 (d, 1H)

Example 40

7-[(3-Fluorophenyl)ethynyl]-2-(6-methyl-3-nitropyridin-2-yl)-5-oxa-2,6-diazaspiro[3.4]oct-6-ene tert-Butyl 7-[(3-fluorophenyl)ethynyl]-5-oxa-2,6-diazaspiro[3.4]oct-6-ene-2-carboxylate (Compound 40a)

The title compound was prepared following the procedure reported for the compound of Example 3, but replacing Compound 28b for Compound 3c and 1-fluoro-3-iodobenzene for 2-bromo-6-methylpyridine. After the usual work-up, the crude was purified by automated flash chromatography (SP1®TM-Biotage; gradient Petroleum Ether-EtOAc from 1:0 to 60:40) affording the title product as colourless oil. Yield: 15.5%.

MS: [M+H]$^+$=331.35

7-[(3-Fluorophenyl)ethynyl]-5-oxa-2,6-diazaspiro[3.4]oct-6-ene (Compound 40b)

The title compound was synthesized following the method reported for Compound 1c, substituting Compound 1b with Compound 40a and running the reaction in chloroform. The crude brownish oily residue was used without further purification in the next reaction step. Yield: 33.4%.

MS: [M+H]$^+$=231.24

7-[(3-Fluorophenyl)ethynyl]-2-(6-methyl-3-nitropyridin-2-yl)-5-oxa-2,6-diazaspiro[3.4]oct-6-ene The title compound was prepared following the method described for the compound of Example 1, replacing Compound 1c with Compound 40b. The crude was purified by automated flash chromatography (SP1®TM-Biotage; gradient Petroleum Ether-EtOAc from 9:1 to 5:5) to give the title compound as yellow oil. Yield: 36.9%.

MS: [M+H]$^+$=367.35

$^1$H-NMR: (CDCl$_3$, δ): 2.54 (s, 3 H) 3.50 (s, 2 H) 4.40-4.57 (m, 5 H) 6.66 (d, J=8.31 Hz, 1 H) 7.11-7.18 (m, 1 H) 7.25 (d, J=9.54 Hz, 1 H) 7.31-7.42 (m, 2 H) 8.19 (d, J=8.31 Hz, 1 H).

Example 41, 42, 43

3-[(3-Chlorophenyl)ethynyl]-8-(pyridin-2-ylmethylene)-1-oxa-2-azaspiro[4.5]dec-2-ene 3-[(3-Chlorophenyl)ethynyl]-8-(pyridin-2-ylmethyl)-1-oxa-2-azaspiro[4.5]dec-2-en-8-ol-isomer 1

3-[(3-Chlorophenyl)ethynyl]-8-(pyridin-2-ylmethyl)-1-oxa-2-azaspiro[4.5]dec-2-en-8-ol-isomer 2

To a suspension of triphenyl(2-pyridylmethyl)phosphonium chloride (81.1 mg, 0.19 mmol) stirred at −20° C. under anhydrous nitrogen atmosphere, in 2.5 mL was added dropwise lithium-bis-trimethylsilylamide (1M sol. in THF, 0.415 mL, 0.415 mmol). After 30', a solution of the compound of Example 32 (50 mg, 0.173 mmol) in 0.92 mL of anhydrous THF and the reaction mixture was stirred at −20° C. for 1 hour and at r.t. Then the reaction was heated at 65° C. for 2 h, cooled to r.t and quenched with NH$_4$Cl aqueous saturated solution, extracted with EtOAc, dried over sodium sulphate and evaporated to dryness. The crude was purified by automated flash chromatography (SP1®TM-Biotage; gradient Petroleum Ether-EtOAc from 7:3 to 3:7) to give 24.5 mg of the compound of Example 41 (24.5%) plus 6.1 mg of the compound of Example 42 and 3.3 mg of the compound of Example 43.

Example 41

MS: [M+H]$^+$=363.27

$^1$H-NMR: (CDCl$_3$, J): 1.72-1.91 (m, 2 H), 1.98-2.08 (m, 1 H), 2.08-2.18 (m, 1 H), 2.31-2.43 (m, 1 H), 2.71 (t, J=9.78 Hz, 1 H), 2.81-3.06 (m, 4 H), 6.42 (br. s., 1 H), 7.14 (br. s., 1 H), 7.21 (d, J=7.58 Hz, 1 H), 7.32 (d, J=7.58 Hz, 1 H), 7.35-7.45 (m, 2 H), 7.53 (br. s., 1 H), 7.68 (br. s., 1 H), 8.61 (br. s., 1 H).

Example 42

MS: [M+H]$^+$=381.18

$^1$H-NMR: (CDCl$_3$, δ): 1.56 (d, J=12.72 Hz, 2 H), 1.76-1.90 (m, 4 H), 1.95-2.11 (m, 2 H), 2.90 (s, 2 H), 2.96 (s, 2 H), 7.16 (d, J=7.82 Hz, 1 H), 7.18-7.25 (m, 1 H), 7.31 (d, J=7.58 Hz, 1H), 7.35-7.44 (m, 2 H), 7.51 (s, 1 H), 7.62-7.74 (m, 1H), 8.52 (d, J=4.65 Hz, 1 H)

Example 43

MS: [M+H]$^+$=381.18

$^1$H-NMR: (CDCl$_3$, δ): 1.37-1.49 (m, 2 H), 1.62-1.72 (m, 2 H), 1.82 (d, J=13.45 Hz, 2 H), 2.23 (td, J=12.35, 3.67 Hz, 2 H), 2.93 (s, 2 H), 2.96 (s, 2 H), 7.16 (d, J=7.82 Hz, 1 H), 7.20-7.26 (m, 1 H), 7.32 (d, J=7.82 Hz, 1 H), 7.35-7.43 (m, 2H), 7.51 (s, 1 H), 7.69 (t, J=7.58 Hz, 1 H), 8.54 (d, J=4.65 Hz, 1 H).

Example 44

3-(Phenylethynyl)-1,9,12-trioxa-2-azadispiro[4.2.4.2]tetradec-2-ene

The title compound was synthesized using the same method described for Compound 1b but using Compound 31a instead of N-Boc-4-methylenepiperidine. After the usual work-up procedure, the title product was purified by automated RP chromatography (Isolera®TM-Biotage; gradient buffer NH$_4$HCO$_3$-MeCN from 40-60 a 20-80. Yield: 44.9%.

MS: [M+H]$^+$=298.2

$^1$H-NMR: (CDCl$_3$, δ): 1.64-1.73 (m, 2 H), 1.82-1.90 (m, 2 H), 1.96-2.10 (m, 4 H), 2.94 (s, 2 H), 3.92-4.04 (m, 4 H), 7.33-7.43 (m, 3 H), 7.53 (d, J=7.8, 2H).

Example 45

3-(2-Phenylethynyl)-1-oxa-2-azaspiro[4.5]dec-2-en-8-one

The title compound was synthesized using the same method described for the compound of Example 32, but starting from the compound of Example 44 instead of the compound of Example 31. The crude was purified by automated flash chromatography (SP1®TM-Biotage; Petroleum Ether-EtOAc 8:2) to give the title product as white solid. Yield: 80%.

MS: [M+H]$^+$=254.2

$^1$H-NMR: (CDCl$_3$, δ): 2.00-2.10 (m, 2 H), 2.29-2.44 (m, 4 H), 2.78-2.90 (m, 2 H), 3.05 (s, 2 H), 7.35-7.47 (m, 3 H), 7.55 (d, J=6.36 Hz, 2 H).

Example 46

3-(2-Phenylethynyl)-1-oxa-2-azaspiro[4.5]dec-2-en-8-one oxime

The title product was prepared from the compound of Example 45, using the same method described here for the preparation of Compound Ia. The crude was purified by automated flash chromatography (SP1®TM-Biotage; Petroleum Ether-EtOAc 6:4) to give the title product. Yield: 80%.

MS: [M+H]$^+$=269.2

$^1$H-NMR: (CDCl$_3$, δ): 1.71-1.89 (m, 2 H), 2.05-2.22 (m, 2 H), 2.31-2.41 (m, 1 H), 2.44-2.58 (m, 1 H), 2.58-2.69 (m, 1 H), 2.97 (s, 2 H), 2.97-3.05 (m, 1 H), 7.34-7.46 (m, 3 H), 7.54 (d, J=7.09 Hz, 2 H).

Example 47

3-(Phenylethynyl)-1-oxa-2-azaspiro[4.5]dec-2-en-8-one O-(2-oxotetrahydrofuran-3-yl)oxime To a solution of the compound of Example 46 (50 mg, 0.186 mmol) in THF (5 mL) was added sodium hydride (60% oil dispersion, 7.81 mg, 0.195 mmol) and the mixture was stirred at r.t. for 1 h. Afterwards, 2-bromo-gamma-butyrolactone (17.2 μL, 0.186 mmol) was added and the reaction was stirred overnight, quenched with water, extracted with EtOAc. The combined organic layers were washed with brine, evaporated to dryness in vacuo to afford a crude, which was purified by automated RP chromatography (Isolera®TM-Biotage; gradient buffer NH$_4$HCO$_3$-MeCN from 40-60 a 30-70. Yield: 32%

MS: [M+H]$^+$=353.2

$^1$H-NMR: (CDCl$_3$, δ): 1.73-1.88 (m, 2 H), 2.05-2.22 (m, 2 H), 2.30-2.41 (m, 1 H), 2.41-2.70 (m, 4 H), 2.95-3.05 (m, 3 H), 4.27-4.37 (m, 1 H), 4.43-4.53 (m, 1 H), 4.80-4.94 (m, 1 H), 7.34-7.45 (m, 3 H), 7.50-7.60 (m, 2 H).

Example 48

3-[(6-Methylpyridin-2-yl)ethynyl]-8-pyridin-2-yl-1-oxa-2-azaspiro[4.5]dec-2-ene-8-carbonitrile 4-methylene-1-(2-pyridyl)cyclohexanecarbonitrile (Compound 48a)

The title compound was prepared following the method described for the compound of Example 2a, replacing 1-(3-nitro-2-pyridyl)-4-oxopiperidine with 4-oxo-1-(2-pyridyl)cyclohexanecarbonitrile. The crude was purified by automated flash chromatography (SP1®TM-Biotage; gradient Petroleum ether-EtOAc from 95:5 to 85:15) to give the title compound as yellow oil. Yield: 92.8%.

MS: [M+H]$^+$=199.25

8-(2-Pyridyl)-2-(2-trimethylsilylethynyl)-4-oxa-3-azaspiro[4.5]-2-ene-8-carbonitrile (Compound 48b)

The title compound was prepared following the method described for the compound of Example 1b, replacing Compound 48a for tert-butyl 4-methylenepiperidine-1-carboxylate and Compound 3b for Compound 1a, The crude was purified by automated flash chromatography (SP1®TM-Biotage; gradient Petroleum ether-EtOAc from 95:5 to 85:15) to give the title compound as yellow oil. Yield: 43.7%.

MS: [M+H]$^+$=338.34

3-[(6-Methylpyridin-2-yl)ethynyl]-8-pyridin-2-yl-1-oxa-2-azaspiro[4.5]dec-2-ene-8-carbonitrile The title compound was prepared following the method described for the compound of Example 3, replacing Compound 3c with Compound 48b. The crude was purified by automated flash chromatography (SP1®TM-Biotage; gradient Petroleum ether-EtOAc from 65:35 to 4:6) to give the title compound as yellow oil. Yield: 43.4%.

MS: [M+H]$^+$=357.17

$^1$H-NMR: (CDCl3, δ): 2.06-2.25 (m, 6 H), 2.47-2.58 (m, 2 H), 2.61 (s, 3 H), 3.03 (s, 2 H), 7.20 (d, J=7.82 Hz, 1 H), 7.25-7.32 (m, 1 H), 7.40 (d, J=7.58 Hz, 1 H), 7.57 (d, J=8.07 Hz, 1 H), 7.62 (t, J=7.70 Hz, 1 H), 7.72-7.81 (m, 1 H), 8.66 (d, J=4.65 Hz, 1 H).

Example 49

3-[(5-Fluoropyridin-2-yl)ethynyl]-1,9,12-trioxa-2-azadispiro[4.2.4.2]tetradec-2-ene The title compound was prepared following the method described for the compound of Example 3, replacing Compound 31b for Compound 3c and 2-bromo-5-fluoropyridine for 2-bromo-6-methylpyridine. The crude was purified by automated flash chromatography (SP1®TM-Biotage; gradient Petroleum ether-EtOAc from 65:35 to 4:6) to give the title compound as yellow solid. Yield: 30.2%.

MS: [M+H]$^+$=317.13

$^1$H-NMR: (CDCl$_3$, δ): 1.58-1.78 (m, 2 H), 1.88 (dd, J=13.82, 2.32 Hz, 2 H), 1.95-2.09 (m, 4 H), 2.95 (s, 2 H), 3.92-4.04 (m, 4 H), 7.45 (td, J=8.19, 2.93 Hz, 1 H), 7.58 (dd, J=8.68, 4.52 Hz, 1 H), 8.51 (d, J=2.93 Hz, 1 H).

Example 50

3-[(6-Methylpyridin-2-yl)ethynyl]-1,9,12-trioxa-2-azadispiro[4.2.4.2]tetradec-2-ene The title compound was prepared following the method described for the compound of Example 3, replacing Compound 31b for Compound 3c. The crude was purified by automated flash chromatography (SP1®TM-Biotage; gradient Petroleum Ether-EtOAc from 65:35 to 4:6) to give the title compound as yellow solid. Yield: 47.1%.

MS: $[M+H]^+$=313.08

$^1$H-NMR: (CDCl$_3$, δ): 1.63-1.72 (m, 2 H), 1.80-1.91 (m, 2 H), 1.95-2.09 (m, 4 H), 2.61 (s, 3 H), 2.95 (s, 2 H), 3.92-4.04 (m, 4 H), 7.19 (d, J=7.82 Hz, 1 H), 7.39 (d, J=7.58 Hz, 1 H), 7.62 (t, J=7.70 Hz, 1 H).

Example 51

3-[(6-Fluoropyridin-2-yl)ethynyl]-1,9,12-trioxa-2-azadispiro[4.2.4.2]tetradec-2-ene The title compound was prepared following the method described for the compound of Example 3, replacing Compound 31b for Compound 3c and 2-bromo-6-fluoropyridine for 2-bromo-6-methylpyridine. The crude was purified by automated flash chromatography (SP1®TM-Biotage; gradient Petroleum ether-EtOAc from 65:35 to 4:6) to give the title compound as yellow solid. Yield: 51.1%.

MS: $[M+H]^+$=317.00

$^1$H-NMR: (CDCl$_3$, δ): 1.62-1.75 (m, 2 H), 1.88 (dd, J=13.69, 2.45 Hz, 2 H), 1.95-2.13 (m, 4 H), 2.94 (s, 2 H), 3.88-4.06 (m, 4 H), 6.99 (dd, J=8.31, 2.69 Hz, 1 H), 7.45 (dd, J=7.46, 2.08 Hz, 1 H), 7.82 (q, J=7.91 Hz, 1 H).

Example 52

3-[(6-Fluoropyridin-3-yl)ethynyl]-1,9,12-trioxa-2-azadispiro[4.2.4.2]tetradec-2-ene The title compound was prepared following the method described for the compound of Example 3, replacing Compound 31b for Compound 3c and 5-bromo-2-fluoropyridine for 2-bromo-6-methylpyridine. The crude was purified by automated flash chromatography (SP1®TM-Biotage; gradient Petroleum ether-EtOAc from 8:2 to 5:5) to give the title compound as yellow solid. Yield: 37.2%.

MS: $[M+H]^+$=317.00

$^1$H-NMR: (CDCl$_3$, δ): 1.64-1.77 (m, 2 H), 1.89 (dd, J=13.94, 2.45 Hz, 2 H), 1.96-2.12 (m, 4 H), 2.94 (s, 2 H), 3.87-4.08 (m, 4 H), 6.98 (dd, J=8.44, 3.06 Hz, 1 H), 7.83-8.00 (m, 1 H), 8.41 (d, J=1.96 Hz, 1 H).

Example 53

3-[(3-Nitrophenyl)ethynyl]-1,9,12-trioxa-2-azadispiro[4.2.4.2]tetradec-2-ene The title compound was prepared following the method described for the compound of Example 3, replacing Compound 31b for Compound 3c and 3-bromonitrobenzene for 2-bromo-6-methylpyridine. The crude was purified by automated flash chromatography (SP1®TM-Biotage; gradient Petroleum ether-EtOAc from 8:2 to 5:5) to give the title compound as yellow solid. Yield: %.

MS: $[M+H]^+$=343.08

$^1$H-NMR: (CDCl$_3$, δ): 1.67-1.76 (m, 2 H), 1.82-1.93 (m, 2 H), 1.96-2.11 (m, 4 H), 2.95 (s, 2 H), 3.93-4.05 (m, 4 H), 7.58 (t, J=8.07 Hz, 1 H), 7.83 (d, J=7.58 Hz, 1 H), 8.26 (dd, J=8.31, 1.22 Hz, 1 H), 8.38 (s, 1 H).

Example 54

3-[(2-Methyl-1,3-thiazol-4-yl)ethynyl]-1,9,12-trioxa-2-azadispiro[4.2.4.2]tetradec-2-ene The title compound was prepared following the method described for the compound of Example 3, replacing Compound 31b for Compound 3c and 4-bromo-2-methylthiazole for 2-bromo-6-methylpyridine. The crude was purified by automated flash chromatography (SP1®TM-Biotage; gradient Petroleum ether-EtOAc from 6:4 to 5:5) to give the title compound as yellow solid. Yield: 60.6%.

MS: $[M+H]^+$=319.23

$^1$H-NMR: (CDCl$_3$, δ): 1.63-1.77 (m, 2 H), 1.86 (dd, J=13.57, 2.32 Hz, 2 H), 1.92-2.11 (m, 4 H), 2.75 (s, 3 H), 2.92 (s, 2 H), 3.91-4.06 (m, 4 H), 7.48 (s, 1 H).

Example 55-69

Following the method described for the compound of Example 3, replacing Compound 31b for Compound 3c and using the proper haloderivatives, the Compounds of Example 55-69 were synthesised. Purification was made by using automated flash chromatography (SP1®TM-Biotage). The following Table 1 describes the structure and the analytical characterization of the included Examples.

| Example | Structure | Reagent | MS: $[M+H]^+$ | 1H-NMR CDCl3(δ). |
|---|---|---|---|---|
| 55 | 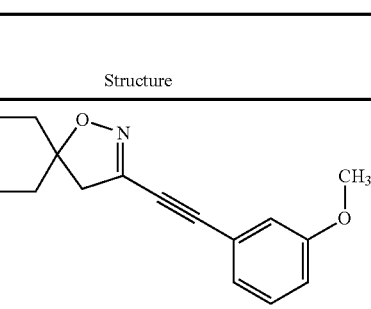 | 3-iodo-methoxy-benzene | 328.15 | 1.64-1.73 (m, 2H), 1.88 (d, J = 13.20 Hz, 2H), 1.96-2.10 (m, 4H), 2.94 (s, 2H), 3.83 (s, 3H), 3.94-4.04 (m, 4H), 6.93-6.99 (m, 1H), 7.05 (s, 1H), 7.13 (d, 7.58 Hz, 1H), 7.25-7.32 (m, 1H) |

-continued

| Example | Structure | Reagent | MS: [M+H]+ | 1H-NMR CDCl3(δ). |
|---|---|---|---|---|
| 56 | 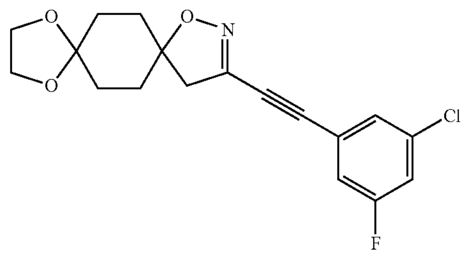 [SMILES: Fc1cc(Cl)cc(C#CC2=NOC3(CCC4(CC3)OCCO4)C2)c1] | 3-chloro-5-fluoro-bromo-benzene | 349.89 | 1.64-1.74 (m, 2H), 1.82-1.92 (m, 2H), 1.95-2.09 (m, 4H), 2.92 (s, 2H), 3.94-4.04 (m, 4H), 7.10-7.18 (m, 2H), 7.32 (s, 1H) |
| 57 | 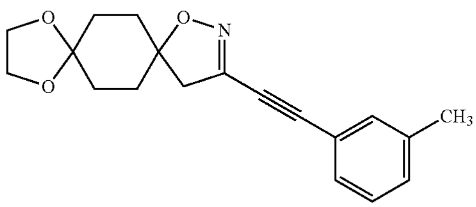 [SMILES: Cc1cccc(C#CC2=NOC3(CCC4(CC3)OCCO4)C2)c1] | 3-methyliodo-benzene | 312.2 | 1.64-1.73 (m, 2H), 1.81-1.91 (m, 2H), 1.96-2.11 (m, 4H), 2.37 (s, 3H), 2.93 (s, 2H), 3.93-4.04 (m, 4H), 7.19-7.30 (m, 2H), 7.31-7.38 (m, 2H) |
| 58 | 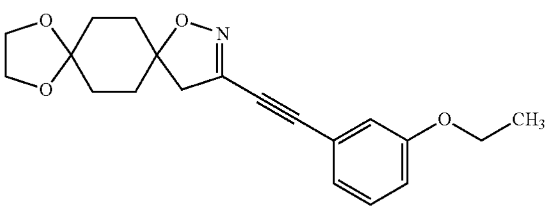 [SMILES: CCOc1cccc(C#CC2=NOC3(CCC4(CC3)OCCO4)C2)c1] | 3-ethoxy-bromo-benzene | 342.14 | 1.44 (t, J = 6.97 Hz, 3H), 1.64-1.74 (m, 2H), 1.80-1.92 (m, 2H), 1.95-2.10 (m, 4H), 2.93 (s, 2H), 3.93-4.02 (m, 4H), 4.05 (q, J = 7.09 Hz, 2H), 6.91-6.98 (m, 1H), 7.04 (s, 1H), 7.11 (d, J = 7.58 Hz, 1H), 7.26 (t, J = 8.30 Hz, 1H) |
| 59 | 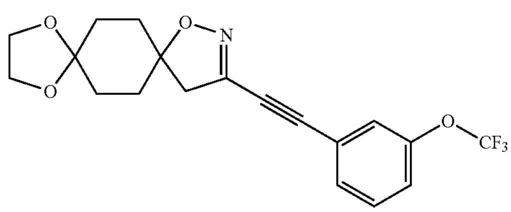 [SMILES: FC(F)(F)Oc1cccc(C#CC2=NOC3(CCC4(CC3)OCCO4)C2)c1] | 3-trifluoro-methoxy-iodobenzene | 382.01 | 1.64-1.74 (m, 2H), 1.82-1.92 (m, 2H), 1.96-2.11 (m, 4H), 2.94 (s, 2H), 3.93-4.05 (m, 4H), 7.26 (d, J = 8.07 Hz, 2H), 7.36-7.49 (m, 3H) |
| 60 | 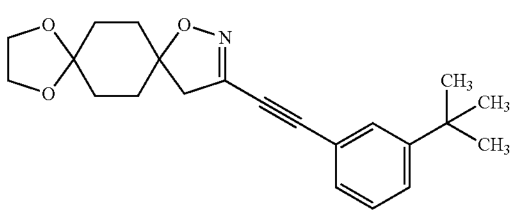 [SMILES: CC(C)(C)c1cccc(C#CC2=NOC3(CCC4(CC3)OCCO4)C2)c1] | 3-tert-butyliodo-benzene | 354.1 | 1.34 (s, 9H), 1.63-1.74 (m, 2H), 1.81-1.92 (m, 2H), 1.97-2.11 (m, 4H), 2.94 (s, 2H), 3.93-4.04 (m, 4H), 7.26-7.38 (m, 2H), 7.44 (d, J = 7.58 Hz, 1H), 7.56 (s, 1H) |
| 61 | 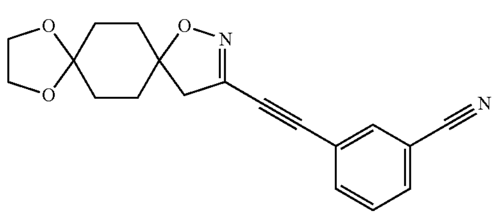 [SMILES: N#Cc1cccc(C#CC2=NOC3(CCC4(CC3)OCCO4)C2)c1] | 3-iodobenzo-nitrile | 323.22 | 1.64-1.74 (m, 2H), 1.82-1.93 (m, 2H), 1.96-2.11 (m, 4H), 2.93 (s, 2H), 3.92-4.05 (m, 4H), 7.51 (t, J = 7.95 Hz, 1H), 7.68 (d, J = 7.82 Hz, 1H), 7.74 (d, J = 7.82 Hz, 1H), 7.80 (s, 1H) |
| 62 | 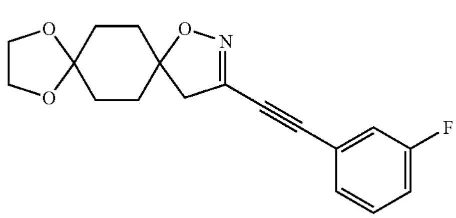 [SMILES: Fc1cccc(C#CC2=NOC3(CCC4(CC3)OCCO4)C2)c1] | 3-fluoroiodo-benzene | 316.19 | 1.63-1.74 (m, 2H), 1.81-1.92 (m, 2H), 1.95-2.11 (m, 4H), 2.93 (s, 2H), 3.93-4.05 (m, 4H), 7.08-7.16 (m, 1H), 7.22 (d, J = 9.54 Hz, 1H), 7.29-7.39 (m, 2H) |

| Example | Structure | Reagent | MS: [M + H]⁺ | 1H-NMR CDCl3(δ). |
|---|---|---|---|---|
| 63 | 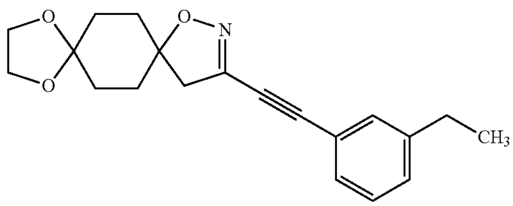 [SMILES: CCc1cccc(C#CC2=NOC3(CCC4(CC3)OCCO4)C2)c1] | 1-bromo-3-ethyl-benzene | 326.26 | 1.26 (t, J = 7.58 Hz, 3H), 1.64-1.74 (m, 2H), 1.81-1.91 (m, 2H), 1.96-2.10 (m, 4H), 2.66 (q, J = 7.58 Hz, 2H), 2.93 (s, 2H), 3.94-4.04 (m, 4H), 7.21-7.31 (m, 2H), 7.35 (d, J = 7.34 Hz, 1H), 7.38 (s, 1H) |
| 64 | 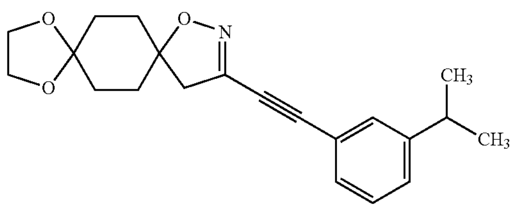 [SMILES: CC(C)c1cccc(C#CC2=NOC3(CCC4(CC3)OCCO4)C2)c1] | 1-bromo-3-isopropyl-benzene | 340.18 | 1.27 (d, J = 6.85 Hz, 6H), 1.64-1.73 (m, 2H), 1.88 (dd, J = 13.94, 2.69 Hz, 2H), 1.96-2.11 (m, 4H), 2.91 (spt, J = 6.80 Hz, 1H), 2.94 (s, 2H), 3.94-4.04 (m, 4H), 7.24-7.29 (m, 1H), 7.29-7.33 (m, 1H), 7.33-7.37 (m, 1H), 7.41 (s, 1H) |
| 65 | 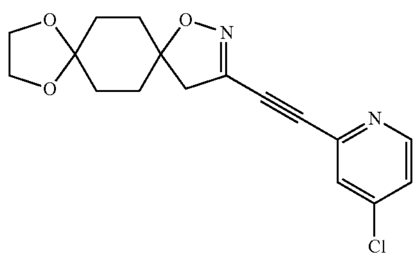 [SMILES: Clc1ccnc(C#CC2=NOC3(CCC4(CC3)OCCO4)C2)c1] | 2-bromo-4-chloro-pyridine | 333.15 | 1.62-1.74 (m, 2H), 1.80-1.93 (m, 2H), 1.94-2.10 (m, 4H), 2.95 (s, 2H), 3.91-4.05 (m, 4H), 7.35 (d, J = 5.13 Hz, 1H), 7.58 (s, 1H), 8.54 (d, J = 5.14 Hz, 1H) |
| 66 | 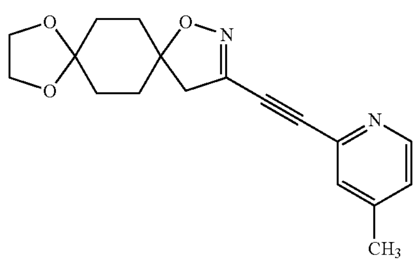 [SMILES: Cc1ccnc(C#CC2=NOC3(CCC4(CC3)OCCO4)C2)c1] | 2-bromo-4-methyl-pyridine | 313.14 | 1.60-1.73 (m, 2H), 1.79-1.92 (m, 2H), 1.95-2.09 (m, 4H), 2.39 (s, 3H), 2.95 (s, 2H), 3.99 (dd, J = 7.70, 4.03 Hz, 4H), 7.10-7.18 (m, 1H), 7.40 (s, 1H), 8.50 (d, J = 4.89 Hz, 1H) |
| 67 | 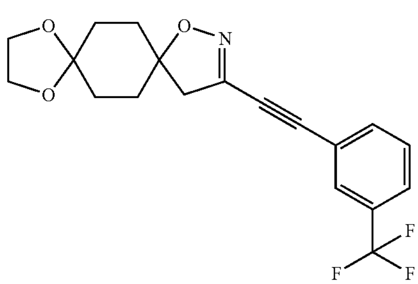 [SMILES: FC(F)(F)c1cccc(C#CC2=NOC3(CCC4(CC3)OCCO4)C2)c1] | 3-trifluoro-methyl-bromo-benzene | 366.13 | 1.64-1.75 (m, 2H), 1.82-1.93 (m, 2H), 1.96-2.11 (m, 4H), 2.94 (s, 2H), 3.94-4.05 (m, 4H), 7.52 (t, J = 7.82 Hz, 1H), 7.66 (d, J = 7.82 Hz, 1H), 7.70 (d, J = 7.58 Hz, 1H), 7.80 (s, 1H) |
| 68 | 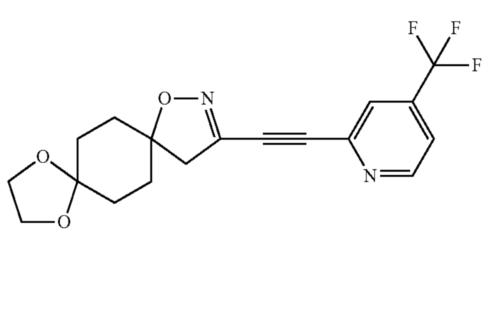 [SMILES: FC(F)(F)c1ccnc(C#CC2=NOC3(CCC4(CC3)OCCO4)C2)c1] | 2-bromo-4-trifluoro-methyl-pyridine | 324.09 | 2.32-2.42 (m, 2H), 2.42-2.56 (m, 2H), 2.93-3.09 (m, 2H), 3.03 (s, 2H), 3.44-3.57 (m, 2H), 7.31-7.36 (m, 1H), 7.42 (dt, J = 6.85, 1.59 Hz, 2H), 7.53 (t, J = 1.59 Hz, 1H) |

| Example | Structure | Reagent | MS: [M + H]⁺ | 1H-NMR CDCl3(δ). |
|---|---|---|---|---|
| 69 | 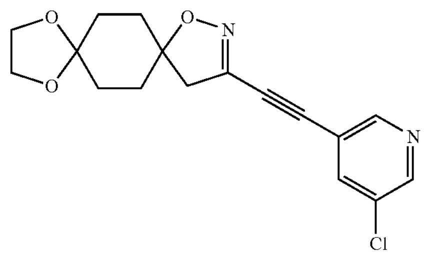 [SMILES: Clc1cncc(C#CC2=NOC3(CCC4(CC3)OCCO4)C2)c1] | 3-iodo-4-chloro-pyridine | 333.15 | 1.63-1.74 (m, 2H), 1.89 (d, J = 12.47 Hz, 2H), 1.96-2.12 (m, 4H), 2.94 (s, 2H), 3.93-4.05 (m, 4H), 7.82 (s, 1H), 8.58 (s, 1H), 8.63 (s, 1H) |

Example 70

1-(2-Furyl)-3-(1,9,12-trioxa-2-azadispiro[4.2.4.2]tetradec-2-en-3-yl)prop-2-yn-1-one 3-Ethynyl-1,9,12-trioxa-2-azadispiro[4.2.4.2]tetradec-2-ene (Compound 70a)

The title product was prepared by the same method illustrated for Compound 11a, but starting from Compound 31b instead of Compound 3c. It was used in the next step without further purification.

MS: [M+H]⁺=222.37

1-(2-Furyl)-3-(1,9,12-trioxa-2-azadispiro[4.2.4.2]tetradec-2-en-3-yl)prop-2-yn-1-one A mixture of Compound 11a (60 mg, 0.27 mmol), 2-furoyl chloride (40.2 μl, 0.41 mmol), triethylamine (75.5 μl, 0.54 mmol), bis(triphenylphosphine)palladium(II)dichloride (11.4 mg, 0.016 mmol), CuI (11.4 mg, 0.16 mmol) in 4 mL of anhydrous THF was stirred under nitrogen for 3 h. Afterwards, the reaction mixture was poured into water, extracted with EtOAc. The organic solvent was washed with brine, dried over sodium sulphate and evaporated to dryness in vacuo. The crude was purified by automated flash chromatography (SP1®TM -Biotage; gradient Petroleum Ether-EtOAc from 7:3 to 5:5) to give 85.5 mg (23.4%) of the title compound.

MS: [M+H]⁺=316.64

$^1$H-NMR: (CDCl$_3$, δ): 1.67-1.75 (m, 2 H), 1.82-1.93 (m, 2 H), 1.93-2.11 (m, 4 H), 2.95 (s, 2 H), 3.92-4.05 (m, 4 H), 6.64 (d, J=2.93 Hz, 1 H), 7.47 (d, J=3.42 Hz, 1 H), 7.73 (s, 1H).

Example 71

4-Hydroxy-2-({[3-(phenylethynyl)-1-oxa-2-azaspiro[4.5]dec-2-en-8-ylidene]amino}oxy)butanoic acid To a solution of the Compound of Example 47 (14 mg, 0.4 mmol) in 1.75 mL of dioxane was added 1M sodium hydroxide (40 μL, 0.4 mmol) and the reaction mixture was stirred at 40° C. for 2 h. After evaporation to dryness, the crude was purified by automated RP flash chromatography (SP1®TM-Biotage; gradient 20 mM aqueous ammonium carbonate-MeCN from 1:0 to 6:4) to give 10 mg of the title compound as a white solid.

MS: [M+H]⁺=371.06

$^1$H-NMR: (DMSO-d$_6$, δ): 1.69-1.97 (m, 6 H), 2.17-2.28 (m, 1 H), 2.28-2.39 (m, 1 H), 2.45-2.58 (m, 1 H), 2.58-2.72 (m, 1 H), 3.11 (d, J=5.14 Hz, 2 H), 3.43-3.57 (m, 2 H) 4.38 (t, J=5.26 Hz, 1 H), 7.41-7.54 (m, 3 H), 7.54-7.61 (m, 2 H)

Example 72

3-[(3-Chlorophenyl)ethynyl]-1,8-dioxa-2-azaspiro[4.5]dec-2-ene

The title compound was prepared following the procedure described for Compound 1b, using Compound 31e instead of Compound 1a and 4-methylenetetrahydropyran (Tetrahedron, 46(7), 2411-2424, 1990) instead of tert-butyl 4-methylenepiperidine-1-carboxylate. After the usual work-up procedure, the residue was purified by means of automated flash chromatography (SP1 ®TM-Biotage; gradient Petroleum Ether-EtOAc from 10:1 to 8:2) to give the title compound as a yellowish solid. Yield: 23.7%.

MS: [M+H]⁺=276.7

$^1$H-NMR: (CDCl$_3$, δ): 1.79-1.89 (m, 2 H), 1.89-1.99 (m, 2 H), 2.95 (s, 2 H), 3.69-3.80 (m, 2 H), 3.92 (ddd, 2 H), 7.29-7.36 (m, 1 H), 7.41 (t, 2H), 7.52 (s, 1 H).

Example 73

3-[(6-Methylpyridin-2-yl)ethynyl]-1,8-dioxa-2-azaspiro[4.5]dec-2-ene 3-(3-Trimethylsylylbut-1-ynyl)-1,8-dioxa-2-azaspiro[4.5]dec-2-ene (Compound 73a)

The title compound was synthesized using the same method described above for Compound 3c, but replacing 4-methylenetetrahydropyran for Compound 3a. The crude was purified by automated flash chromatography (Isolera®TM-Biotage; gradient Petroleum Ether-EtOAc from 95:5 to 75:25) to give the title compound as brownish oil. Yield: 30.2%.

MS: [M+H]⁺=238.21.

$^1$H-NMR: (CDCl$_3$, δ): 0.24-0.27 (m, 9 H), 1.79 (ddd, J=13.45, 9.05, 4.16 Hz, 2 H), 1.90 (dt, J=13.40, 4.40 Hz, 2 H), 2.86 (s, 2 H), 3.71 (dt, J=11.74, 4.65 Hz, 2 H), 3.89 (ddd, J=11.80, 8.86, 3.30 Hz, 2 H).

3-[(6-Methylpyridin-2-yl)ethynyl]-1,8-dioxa-2-azaspiro[4.5]dec-2-ene

The title compound was synthesized using the same method described above for the Compound of Example 3, but replacing Compound 73a for Compound 3c. The crude was purified by automated flash chromatography (Isolera®TM-Biotage; gradient Petroleum ether-EtOAc from 8:2 to 4:6) to give the title compound as yellow solid. Yield: 41.7%.

MS: $[M+H]^+=257.19$.

$^1$H-NMR: (CDCl$_3$, δ): 1.78-1.89 (m, 2 H), 1.89-2.00 (m, 2 H), 2.61 (s, 3 H), 2.97 (s, 2 H), 3.68-3.80 (m, 2 H), 3.85-3.98 (m, 2 H), 7.20 (d, J=7.82 Hz, 1 H), 7.39 (d, J=7.58 Hz, 1 H), 7.62 (t, J=7.70 Hz, 1 H).

Example 74

3-[(4-Chloropyridin-2-yl)ethynyl]-1,8-dioxa-2-azaspiro[4.5]dec-2-ene

The title compound was synthesized using the same method described above for the Compound of Example 3, but replacing Compound 73a for Compound 3c and 2-bromo-4-chloropyridine for 6-bromo-2-methylpyridine. The crude was purified by automated flash chromatography (Isolera®TM-Biotage; gradient Petroleum ether-EtOAc from 8:2 to 35:65) to give the title compound. Yield: 67%.

MS: $[M+H]^+=277.12$.

$^1$H-NMR: (CDCl$_3$, δ): 1.82-1.90 (m, 2 H), 1.90-1.99 (m, 2 H), 2.97 (s, 2 H), 3.75 (dt, J=11.68, 4.68 Hz, 2 H), 3.91 (ddd, J=11.86, 8.93, 118 Hz, 2 H), 7.35 (dd, J=5.38, 1.96 Hz, 1 H), 7.58 (d, J=1.71 Hz, 1 H), 8.55 (d, J=5.38 Hz, 1 H).

Example 75

3-[(3-Chlorophenyl)ethynyl]-1-oxa-8-thia-2-azaspiro[4.5]dec-2-ene 8,8-dioxide

4-Methylenetetrahydro-2H-thiopyran 1,1-dioxide (Compound 75a)

The title product was synthesized following the procedure reported for Compound 2a, but replacing 4-thienopiranone-S,S-dioxide for 1-(3-nitro-2-pyridyl)-4-oxopiperidine. After the usual work-up procedure, the residue was purified by means of automated flash chromatography (Isolera®TM-Biotage; gradient Petroleum Ether-EtOAc from 85:15 to 6:4) to give the title compound. Yield: 79%

MS: $[M+H]^+=147.21$.

$^1$H-NMR: (CDCl$_3$, δ): 2.58 (t, J=6.30 Hz, 4 H), 3.11 (t, J=6.30, 4 H), 4.92 (s, 2 H).

3-Trimethylsilylethynyl-1-oxa-8-thia-2-azaspiro[4.5]dec-2-ene 8,8-dioxide (Compound 75b)

The title compound was synthesized using the same method described above for Compound 3c, but replacing Compound 75a for Compound 3a.
The crude was purified by automated flash chromatography (Isolera®TM-Biotage; gradient Petroleum Ether-EtOAc from 95:5 to 7:3) to give the title compound as a white solid brownish oil. Yield: 40.1%.

MS: $[M+H]^+=286.25$.

$^1$H-NMR: (CDCl$_3$, δ): 0.26 (s, 9 H), 2.25-2.37 (m, 2 H), 2.43 (td, J=14.00, 2.90 Hz, 2 H), 2.93 (s, 2 H), 2.95-3.04 (m, 2 H), 3.47 (td, J=13.57, 3.91 Hz, 2 H).

3-[(3-Chlorophenyl)ethynyl]-1-oxa-8-thia-2-azaspiro[4.5]dec-2-ene 8,8-dioxide The title compound was synthesized using the same method described above for the Compound of Example 3, but replacing Compound 75b for Compound 3c and 1-chloro-3-iodobenzene for 6-bromo-2-methylpyridine. The crude was purified by automated flash chromatography (Isolera®TM-Biotage; gradient Petroleum ether-EtOAc from 85:15 to 65:35) to give the title compound. Yield: 54%.

MS: $[M+H]^+=323.87$.

$^1$H-NMR: (CDCl$_3$, δ): 2.32-2.42 (m, 2 H), 2.42-2.56 (m, 2 H), 2.93-3.09 (m, 2 H), 3.03 (s, 2 H), 3.44-3.57 (m, 2 H), 7.31-7.36 (m, 1 H), 7.42 (dt, J=6.85, 1.59 Hz, 2 H), 7.53 (t, J=1.59 Hz, 1 H).

Example 76

3-[(3-Chlorophenyl)ethynyl]-1,7-dioxa-2-azaspiro[4.5]dec-2-ene

The title compound was prepared following the procedure described for Compound 3c, using Compound 31f instead of Compound 3b and 3-methylenetetrahydropyran (Kirmse, W.; Rode, K. Chemische Berichte, 120, 1987, 847-848) instead of Compound 3a. After the usual work-up procedure, the residue was purified by means of automated flash chromatography (Horizon®TM-Biotage; gradient Petroleum Ether-EtOAc from 1:0 to 8:2) to give the title compound as a grey solid. Yield: 4%

MS: $[M+H]^+=276.25$ $^1$H-NMR: (CDCl$_3$, δ): 1.62-1.74 (m, 1 H), 1.86-2.09 (m, 3 H), 2.90 (d, 1 H), 3.11 (d, 1 H), 3.52-3.67 (m, 3 H), 3.73-3.82 (m, 1 H), 7.29-7.35 (m, 1 H), 7.37-7.44 (m, 2 H), 7.52 (t, 1 H).

Example 77

3-[(3-Chlorophenyl)ethynyl]-1,9-dioxa-2-azadispiro[4.2.4.2]tetradec-2-ene-Isomer A

8-Methylene-1-oxaspiro[4.5]decane (Compound 77a)

The title compound was prepared by following the procedure reported for Compound 2a, but replacing 1-oxaspiro[4.5]decan-8-one for 1-(3-nitro-2-pyridyl)-4-oxopiperidine. After the usual work-up procedure, the residue was purified by means of automated flash chromatography (SP1®TM-Biotage; gradient Petroleum Ether-EtOAc from 100:5 to 75:25) to give the title compound. Yield: 29%.

$^1$H-NMR: (CDCl$_3$, δ): 1.50-1.60 (m, 2 H), 1.67-1.75 (m, 4 H), 1.88-2.00 (m, 2 H), 2.08-2.18 (m, 2 H), 2.31-2.43 (m, 2 H), 3.86 (t, J=6.7 Hz, 2 H), 4.65 (s, 2 H).

3-Trimethysilylethynyl-1,9-dioxa-2-azadispiro[4.2.4.2]tetradec-2-ene (Compound 77b-isomer A and B)

The title compounds were synthesized using the same method described above for Compound 3c, but replacing Compound 77a for Compound 3a.
The crude was purified by automated flash chromatography (Isolera®TM-Biotage; gradient Petroleum Ether-EtOAc from 95:5 to 75:25) to give the title compound as yellowish oils. Yield: 17.6% of the first eluted Isomer A and 11.6% of the Isomer B.

MS: [M+H]$^+$=292.48

$^1$H-NMR: Isomer A, (CDCl$_3$, δ): ppm 0.25 (s, 9 H), 1.58-1.70 (m, 4 H), 1.70-1.77 (m, 2 H), 1.79-1.91 (m, 4 H), 1.90-2.00 (m, 2 H), 2.80 (s, 2 H), 3.78-3.93 (m, 2 H).

$^1$H-NMR: Isomer B, (CDCl$_3$, δ): ppm 0.25 (s, 9 H), 1.46 (ddd, J=13.6, 9.8, 4.0 Hz, 2 H), 1.58-1.67 (m, 2 H), 1.67-1.75 (m, 2 H), 1.82-2.00 (m, 4 H), 2.07 (ddd, J=13.7, 10.0, 4.2 Hz, 2 H), 2.83 (s, 2 H), 3.77-3.93 (m, 2 H).

3-[(3-Chlorophenyl)ethynyl]-1,9-dioxa-2-azadispiro [4.2.4.2]tetradec-2-ene-isomer A The title compound was synthesized using the same method described above for the Compound of Example 3, but replacing Compound 77b-Isomer A for Compound 3c and 1-chloro-3-iodobenzene for 6-bromo-2-methylpyridine. The crude was purified by automated flash chromatography (Isolera®TM-Biotage; gradient Petroleum ether-EtOAc from 95:5 to 8:2) to give the title compound as ivory solid. Yield: 69%.

MS: [M+H]$^+$=330.03

$^1$H-NMR: (CDCl$_3$, δ): 1.49 (ddd, J=13.51, 9.72, 3.91 Hz, 2 H), 1.62-1.70 (m, 2 H), 1.70-1.77 (m, 2 H), 1.87-2.00 (m, 4 H), 2.12 (ddd, J=13.33, 9.66, 4.16 Hz, 2 H), 2.92 (s, 2 H), 3.86 (t, J=6.72 Hz, 2 H), 7.29-7.34 (m, 1 H), 7.36-7.43 (m, 2 H), 7.51 (s, 1 H).

Example 78

3-[(3-Chlorophenyl)ethynyl]-1,9-dioxa-2-azadispiro [4.2.4.2]tetradec-2-ene-isomer B The title compound was synthesized using the same method described above for the Compound of Example 3, but replacing Compound 77b-Isomer B for Compound 3c and 1-chloro-3-iodobenzene for 6-bromo-2-methylpyridine. The crude was purified by automated flash chromatography (Isolera®TM-Biotage; gradient Petroleum ether-EtOAc from 95:5 to 8:2) to give the title compound as pale yellow solid. Yield: 33.5%.

MS: [M+H]$^+$=330.18

$^1$H-NMR: (CDCl$_3$, δ): 1.61-1.68 (m, 2 H), 1.71-1.78 (m, 2 H), 1.80-2.01 (m, 8 H), 2.89 (s, 2 H), 3.85 (t, J=6.75 Hz, 2 H), 7.27-7.33 (m, 1 H), 7.35-7.43 (m, 2 H), 7.52 (t, J=1.66 Hz, 1 H).

Example 79

3-[(3-Methylphenyl)ethynyl]-1,9-dioxa-2-azadispiro [4.2.4.2]tetradec-2-ene

The title compound was synthesized using the same method described above for the Compound of Example 3, but replacing Compound 77b-Isomer B for Compound 3c and 3-iodotoluene for 6-bromo-2-methylpyridine. The crude was purified by automated flash chromatography (Isolera®TM-Biotage; gradient Petroleum ether-EtOAc from 95:5 to 8:2) to give the title compound as ivory solid. Yield: 67.6%.

MS: [M+H]$^+$=310.24

$^1$H-NMR: (CDCl$_3$, δ): 1.49 (ddd, J=13.39, 9.84, 3.91 Hz, 2 H), 1.67 (dd, J=12.47, 4.65 Hz, 2 H), 1.70-1.77 (m, 2 H), 1.85-2.00 (m, 4 H), 2.12 (ddd, J=13.14, 9.60, 3.91 Hz, 2 H), 2.37 (s, 3 H), 2.92 (s, 2 H), 3.86 (t, J=6.72 Hz, 2 H), 7.17-7.30 (m, 2 H), 7.34 (d, J=11.98 Hz, 2 H).

Example 80

3-{[2-(6-Methyl-3-nitropyridin-2-yl)-5-oxa-2,6-diazaspiro[3.4]oct-6-en-7-yl]ethynyl}phenol Tert-butyl 7-ethynyl-5-oxa-2,6-diazaspiro[3.4]oct-6-ene-2-carboxylate (Compound 80a)

A solution of Compound 28b (557 mg, 1.81 mmol) and tetrabutylammonium fluoride hydrate (759 mg, 2.72 mmol) in 10 mL of THF was stirred at r.t. for 4 h. After the usual work-up with EtOAc-water the crude residue was used in the next step without further purification.

MS: [M+H]$^+$=238.4

Tert-butyl 7-[(3-hydroxyphenyl)ethynyl]-5-oxa-2,6-diazaspiro[3,4]oct-6-ene-2-carboxylate (Compound 80b)

The title compound was synthesized using the same method described above for the Compound of Example 3, but replacing Compound 80a for Compound 3c and 3-iodophenol for 6-bromo-2-methylpyridine. The crude was purified by automated flash chromatography (SP1®TM-Biotage; gradient Petroleum ether-EtOAc from 8:2 to 65:35) to give the title compound as yellowish glassy solid. Yield: 28.8%.

MS: [M+H]$^+$=329.4

$^1$H-NMR: (CDCl$_3$, δ): 1.48 (s, 9 H), 3.40 (s, 2 H), 4.07 (d, J=10.3 Hz, 2 H), 4.31 (d, J=10.0 Hz, 2 H), 4.99 (s, 1 H), 6.91 (ddd, 1 H), 6.98-7.02 (m, 1 H), 7.12 (d, J=7.8 Hz, 1 H), 7.28 (t, J=8.1 Hz, 1 H).

3-(5-Oxa-2,6-diazaspiro[3.4]oct-6-en-7-ylethynyl) phenol (Compound 80c)

The title compound was synthesized following the method reported for the Compound 1c, substituting Compound 1b with Compound 80b. The crude residue was used without further purification in the next reaction. Yield: 90.4%.

MS: [M+H]$^+$=229.3

3-{[2-(6-Methyl-3-nitropyridin-2-yl)-5-oxa-2,6-diazaspiro[3.4]oct-6-en-7-yl]ethynyl}phenol The title compound was prepared following the method described for the compound of Example 1, replacing Compound 1c with Compound 80c. After the usual work-up procedure, the title product was purified by automated RP chromatography (SP1®TM-Biotage; gradient buffer NH$_4$HCO$_3$-MeCN from 20-80 a 40-60. Yield: 26%.

MS: [M+H]$^+$=365.05

$^1$H-NMR: (CDCl$_3$, δ): 2.51 (s, 3 H), 3.49 (s, 2 H), 4.38 (d, 2 H), 4.49 (d, 2 H), 4.83 (br. s., 1 H), 6.65 (d, 1 H), 6.92 (d, 1 H), 7.01 (s, 1 H), 7.14 (d, 1 H), 7.23-7.32 (m, 5 H), 8.18 (d, 1H).

Example 81

3-{[2-(6-Methyl-3-nitropyridin-2-yl)-5-oxa-2,6-diazaspiro[3.4]oct-6-en-7-yl]ethynyl}benzonitrile tert-Butyl 7-[(3-cyanophenyl)ethynyl]-5-oxa-2,6-diazaspiro[3.4]oct-6-ene-2-carboxylate (Compound 81a)

The title compound was synthesized using the same method described above for the Compound of Example 3, but replacing Compound 80a for Compound 3c and 3-iodobenzonitrile for 6-bromo-2-methylpyridine. The crude was purified by automated flash chromatography (SP1®TM-Biotage; gradient Petroleum ether-EtOAc from 9:1 to 6:4) to give the title compound as yellowish glassy solid. Yield: 84.5%.

MS: [M+H]$^+$=338.4

$^1$H-NMR: (CDCl$_3$, δ): 1.47 (s, 9 H), 3.39 (s, 2 H), 4.06 (dd, J=9.8, 1.2 Hz, 2 H), 4.32 (dd, J=9.8, 1.2 Hz, 2 H), 7.48-7.55 (m, 1 H), 7.69 (ddd, J=7.9, 1.4 Hz, 1 H), 7.74 (ddd, J=7.9, 1.4 Hz, 1 H), 7.78-7.83 (m, 1 H).

3-(5-Oxa-2,6-diazaspiro[3.4]oct-6-en-7-ylethynyl)benzonitrile (Compound 81b)

The title compound was synthesized following the method reported for the Compound 1c, substituting Compound 1b with Compound 81a. The crude residue was used without further purification in the next reaction. Yield: 90.4%.

MS: [M+H]$^+$=238.3

3-{[2-(6-Methyl-3-nitropyridin-2-yl)-5-oxa-2,6-diazaspiro[3.4]oct-6-en-7-yl]ethynyl}benzonitrile The title compound was prepared following the method described for the compound of Example 1, replacing Compound 1c with Compound 81b. After the usual work-up procedure, the title product was purified by automated RP chromatography (SP1®TM-Biotage; gradient buffer NH$_4$HCO$_3$— MeCN from 20-80 a 40-60. Yield: 72.5%. Yellowish solid.

MS: [M+H]$^+$=374.11

$^1$H-NMR: (CDCl$_3$, δ): 2.52 (s, 3 H), 3.50 (s, 2 H), 4.38-4.44 (m, 1 H), 4.49-4.54 (m, 1 H), 6.66 (d, J=8.31 Hz, 1 H), 7.53 (dd, J=7.90 Hz, 1 H), 7.71 (ddd, J=7.80, 1.50 Hz, 1 H), 7.76 (ddd, J=7.80, 1.30 Hz, 1 H), 7.83 (dd, J=1.30 Hz, 1 H), 8.18 (d, J=8.31 Hz, 1 H).

Example 82

3'-[(3-Chlorophenyl)ethynyl]-2,3-dihydro-4'H-spiro[indene-1,5'-isoxazol]-3-ol The title compound was prepared following the procedure described for Compound 3c, using Compound 31f instead of Compound 3b and 3-methyleneindan-1-ol (Angew Chem, Int Ed, 48(33), 2009, 6148-6151) instead of Compound 3a. After the usual work-up procedure, the residue was purified by means of automated flash chromatography (Horizon®TM-Biotage; gradient Petroleum Ether-EtOAc from 9:1 to 1:1) to give the title compound as a brownish oil. Yield: 74%
The title compound was characterized as a 83:17 diastereoisomeric mixture by $^1$H-NMR spectrum.

MS: [M+H]$^+$=324.01

$^1$H-NMR: (CDCl$_3$, δ): 2.25 (dd, J=13.94, 4.89 Hz, 1 H), 2.57 (dd, J=14.30, 3.79 Hz, 0.21 H), 2.74 (dd, J=14.31, 6.48 Hz, 0.21 H), 3.02 (dd, J=13.94, 6.60 Hz, 1 H), 3.39 (dd, 0.42) 3.50 (dd, 2 H) 5.12-5.25 (m, 0.21 H), 5.50 (t, J=5.62 Hz, 1 H), 7.30-7.38 (m, 1 H), 7.38-7.52 (m, 6 H), 7.56 (s, 1 H).

Example 83

3'-[(3-Chlorophenyl)ethynyl]-4'H-spiro[indene-1,5'-isoxazol]-3(2H)-one

A solution of oxalyl chloride (64.6 µL, 0.74 mmol) in 5 mL of anhydrous CH$_2$Cl$_2$ was cooled to −60° C.; DMSO (105 µL, 1.48 mmol) was added dropwise so as to keep the reaction at the same temperature. After 15 min. the compound of Example 82 (174 mg, 0.49 mmol) dissolved in 1 mL of anhydrous CH$_2$Cl$_2$ was added and after 30 minutes TEA (0.413 mL, 2.96 mL) was added dropwise. Turning off the cooling and heating up to r.t., the reaction mixture was stirred for 3 hours, then it was quenched with H$_2$O, extracted with CH$_2$Cl$_2$ and dried on Na$_2$SO$_4$. The residue from evaporation was purified by means of automated flash chromatography (SP01®TM-Biotage; gradient Petroleum Ether-EtOAc from 95:5 to 1:1) to give the title compound as a brownish oil. Yield: 50%

MS: [M+H]$^+$=322.2

$^1$H-NMR: (CDCl$_3$, δ): 3.01 (d, J=18.83 Hz, 1 H), 3.30 (d, J=18.83 Hz, 1 H), 3.48 (d, J=17.36 Hz, 1 H), 3.63 (d, J=17.36 Hz, 1 H), 7.31-7.38 (m, 1 H), 7.40-7.49 (m, 2 H), 7.55-7.57 (m, 1H), 7.60 (td, J=7.40, 1.10 Hz, 1 H), 7.69-7.73 (m, 1 H), 7.75-7.83 (m, 2 H).

Example 84

3'-[(3-Chlorophenyl)ethynyl]-N-methoxy-4'H-spiro[indene-1,5'-[1,2]oxazol]-3(2H)-imine To a solution of the Compound of Example 83 (0.14 g, 0.44 mmol) in 1.5 mL of pyridine was added O-methylhydroxylamine (0.04 g, 0.48 mmol). After 4 hours stirring at r.t., the reaction was checked by TLC and considered to completion. It was diluted with water, acidified by 1N HCl and extracted with EtOAc. After drying on Na$_2$SO$_4$ and evaporation to dryness, the residue from evaporation was purified by means of automated flash chromatography (SP01®TM-Biotage; gradient Petroleum Ether-EtOAc from 95:5 to 1:1) to give the title compound as a colorless oil. Yield: 75.4%

MS: [M+H]$^+$=351.44

$^1$H-NMR: (CDCl$_3$, δ): 3.19 (d, 1 H), 3.34-3.41 (m, 1 H), 3.43 (d, 1 H), 3.51-3.57 (m, 1 H), 4.02 (s, 3 H), 7.30-7.37 (m, 1 H), 7.39-7.51 (m, 5 H), 7.56 (t, 1H), 7.71-7.77 (m, 1 H)

Example 85-86

10-[(3-Chlorophenyl)ethynyl]-1,8-dioxa-9-azadispiro[3.2.4.2]tridec-9-ene (isomer 1) and 10-[(3-Chlorophenyl)ethynyl]-1,8-dioxa-9-azadispiro[3.2.4.2]tridec-9-ene (isomer 2)

7-Methylidene-1-oxaspiro[3.5]nonane (Compound 85a)

N-(para-Toluenesulfonyl)dimethylsulfoximine (1.49 g, 6.01 mmol) and anhydrous DMSO (5 mL) were added to NaH 60% oil dispersion (0.22 g, 5.46 mmol) kept under stirring under anhydrous inert gas atmosphere in a flamed 3 necks flask. The mixture became greenish, and then changed to yellow. After stirring at 35° C. for 10 h, a solution of 4-methylidenecylohexanone (0.2 g, 1.82 mmol) in 5 mL of DMSO was added and the reaction mixture was stirred at 50° C. for 20 h. Afterwards, the reaction mixture was diluted with a saturated solution of NaCl and extracted with Et$_2$O (3 times). After drying on Na$_2$SO$_4$ and evaporation to dryness, the residue from evaporation was purified by means of automated flash chromatography (Isolera®TM-Biotage; isocratic Petroleum Ether-EtOAc 9:1) to give 0.252 g of the title compound as a colorless oil. Yield: 27.8%.

MS: [M+H]$^+$=138.21

$^1$H-NMR: (CDCl$_3$, δ): 1.80-1.99 (m, 4 H), 2.05-2.15 (m, 2 H), 2.27-2.37 (m, 2 H), 2.41 (t, J=7.7 Hz, 2 H), 4.55 (t, J=7.8 Hz, 2 H), 4.66 (s, 2 H).

10-[(3-Chlorophenyl)ethynyl]-1,8-dioxa-9-aza-dispiro[3.2.4.2]tridec-9-ene (isomer 1) and 10-[(3-Chlorophenyl)ethynyl ]-1,8-dioxa-9-azadispiro [3.2.4.2]tridec-9-ene (isomer 2)

The title compounds were prepared following the procedure described for Compound 3c, using Compound 31f instead of Compound 3b and Compound 85a instead of Compound 3a. After the usual work-up procedure, the residue was purified by means of automated flash chromatography (SP01®TM-Biotage; gradient Petroleum Ether-EtOAc from 1:0 to 6:4) to give a first group of fractions affording the less polar diastereoisomer (Example 86; 43.9%) followed by a third group of fractions containing the more polar diastereoisomer (Example 85; 25.4%).

Example 85

MS: [M+H]$^+$=315.80
$^1$H-NMR: (CDCl$_3$, δ): 1.63 (ddd, J=13.4, 9.4, 4.2 Hz, 2 H), 1.78-1.90 (m, 2 H), 2.00-2.10 (m, 2 H), 2.16 (ddd, J=13.2, 9.3, 4.2 Hz, 2 H), 2.42 (t, J=7.8 Hz, 2 H), 2.89 (s, 2 H), 4.55 (t, J=7.8 Hz, 2 H), 7.31 (dd, J=7.9 Hz, 1 H), 7.36-7.43 (m, 2 H), 7.51 (t, J=1.8 Hz, 1 H).

Example 86

MS: [M+H]$^+$=315.80
$^1$H-NMR: (CDCl$_3$, δ): 1.79-1.88 (m, 4 H), 1.97-2.06 (m, 4 H), 2.43 (t, J=7.8 Hz, 2 H), 2.89 (s, 2 H), 4.54 (t, J=7.8 Hz, 2 H), 7.27-0.34 (m, 1 H), 7.36-7.43 (m, 2 H), 7.49-7.53 (m, 1 H).

Example 87

3-[(3-Chlorophenyl)ethynyl]-1,9,13-trioxa-2-aza-dispiro[4.2.5.2]pentadec-2-ene

A solution of the compound of Example 32 (0.41 g, 1.42 mmol), 1,3-propandiol (0.15 g, 1.95 mmol) and p-toluensulfonic acid. H$_2$O (7.5 mg, 0.04 mmol) in 30 mL of benzene was stirred at reflux for 10.5 h, removing water with a Dean-Stark Apparatus. Dilution with water, washing with aq. 5% NaHCO$_3$, drying the organic layer over Na$_2$SO$_4$ afforded the title compound as dense yellow oil. This was further purified by means of automated flash chromatography (SP01®TM-Biotage; gradient Petroleum Ether-EtOAc from 9:1 to 7:3) giving a white solid. Yield: 75.3%.
MS: [M+H]$^+$=346.27
$^1$H-NMR: (CDCl$_3$, δ): 1.77 (d, J=5.4 Hz, 4 H), 2.00 (d, J=7.6 Hz, 6 H), 2.91 (s, 2 H), 3.92 (s, 2 H), 3.96 (s, 2 H), 7.31 (s, 1 H), 7.36-7.44 (m, 2 H), 7.52 (s, 1 H).

Example 88

3'-[(6-Methylpyridin-2-yl)ethynyl]-2,3-dihydro-4'H-spiro[indene-1,5'-[1,2]oxazol]-3-ol 3'-[(Trimethylsilyl)ethynyl]-2,3-dihydro-4'H-spiro [indene-1,5'-[1,2]oxazol]-3-ol (Compound 88a)

The title compound was prepared following the procedure described for Compound 3c, using 3-methyleneindan-1-ol (Angew. Chem., Int. Ed., 48(33), 2009, 6148-6151) instead of Compound 3a. After the usual work-up procedure, the residue was purified by means of automated flash chromatography (SP01®TM-Biotage; gradient Petroleum Ether-EtOAc from 9:1 to 1:1) to give the title compound as a brownish oil. Yield: 79.9%
MS: [M+H]$^+$=286.38

3-[2-(6-Methyl-2-pyridyl)ethynyl]spiro[4H-isoxazole-5,3'-indane]-1'-ol

The title compound was synthesized using the same method described above for the compound of Example 3, but replacing Compound 88a for Compound 3c and 6-bromo-2-methylpyridine for 3-iodophenol. The crude was purified by automated flash chromatography (SP1®TM-Biotage; gradient Petroleum Ether-EtOAc from 9:1 to 4:6) to give the title compound as a brownish oil. Yield: 67.6%.
MS: [M+H]$^+$=305.31
$^1$H-NMR: (CDCl$_3$, δ): 2.64 (s, 3H), 3.02 (d, 1H) 3.35 (d, 1H), 3.55 (d, 1H), 3.65 (d, 1H), 5.41-5.45 (m, 1H), 7.23 (d, 1H), 7.44 (d, 1H), 7.55-7.62 (m, 1H), 7.63-7.72 (m, 2H), 7.76 (d, 1H), 7.80 (d, 1H).

Example 89

3-[(3-Chlorophenyl)ethynyl]-1-oxa-2-azadispiro [4.2.4.2]tetradec-2-ene

8-Methylenespiro[4.5]decane (Compound 89a)

The title compound was prepared following the method reported here for Compound 31a. As starting material spiro [4.5]decan-8-one replaced 1,4-dioxaspiro[4.5]decan-8-one. After the usual work-up procedure, the residue was purified by means of automated flash chromatography (SP01®M-Biotage; CH$_2$Cl$_2$) to give the title compound as a colorless oil. Yield: 98.5%.
$^1$H-NMR: (CDCl$_3$, δ): 1.37-1.49 (m, 8 H), 1.63 (dt, J=7.2, 3.6 Hz, 4 H), 2.16 (t, J=6.4 Hz, 4 H), 4.61 (s, 2 H).

3-[(3-Chlorophenyl)ethynyl]-8,8-difluoro-1-oxa-2-azaspiro[4.5]dec-2-ene

The title compound was prepared following the procedure described for Compound 3c, using Compound 31f instead of Compound 3b and Compound 89a instead of Compound 3a. After the usual work-up procedure, the residue was purified by means of automated flash chromatography (ISOLERA®TM-Biotage; gradient Petroleum Ether-EtOAc from 97:3 to 9:1) to give the title compound as a white-yellowish solid. Yield: 58.5%.
MS: [M+H]$^+$=328.29
$^1$H-NMR: (CDCl$_3$, δ): 1.31-1.41 (m, 2 H), 1.46 (dt, J=19.7, 6.9 Hz, 4 H), 1.59-1.76 (m, 8 H), 1.84-1.94 (m, 2 H), 2.89 (s, 2 H), 7.26-7.34 (m, 1 H), 7.35-7.45 (m, 2 H), 7.51 (s, 1 H).

Example 90

3-[(3-Chlorophenyl)ethynyl]-8,8-difluoro-1-oxa-2-azaspiro[4.5]dec-2-ene 1,1-Difluoro-4-methylenecyclohexane (Compound 90a)

A methyl triphenyl phosphonium bromide/sodium amide mixture (MTP instant ylide, 0.49 g, 1.24 mmol) was suspended in anhydrous Et$_2$O (3 mL) stirring for 1 h at r.t. Afterwards, the reaction mixture was cooled at 0° C. and a solution of 4,4-difluorocyclohexanone (0.145 g, 1.08 mmol)

in 3 mL of Et$_2$O was added dropwise into. Stirring at r.t. was maintained for 16 h, then the reaction mixture was filtered and the filtrate was used in the next step without further purification.

3-[(3-Chlorophenyl)ethynyl]-8,8-difluoro-1-oxa-2-azaspiro[4.5]dec-2-ene

The title compound was prepared following the procedure described for Compound 3c, using Compound 31f instead of Compound 3a and Compound 90a instead of Compound 3b. After the usual work-up procedure, the residue was purified by means of automated flash chromatography (ISOLERA®TM-Biotage; gradient Petroleum Ether-EtOAc from 99:1 to 95:5) to give the title compound as a yellowish solid. Yield: 41.9%.
MS: [M+H]$^+$=310.35
$^1$H-NMR: (CDCl$_3$, δ): 1.82-1.92 (m, 2 H), 1.97-2.14 (m, 4 H), 2.14-2.34 (m, 2 H), 2.95 (s, 2 H), 7.33 (d, J=7.6 Hz, 1 H), 7.41 (t, J=7.1 Hz, 2H), 7.52 (s, 1 H).

Example 91

3-[(3-Methylphenyl)ethynyl]-1-oxa-2-azadispiro[4.2.4.2]tetradec-2-ene 1-(3,3-Diethoxyprop-1-yn-1-yl)-3-methylbenzene (Compound 91a)

The title compound was synthesized following the procedure reported for Compound 31c, but using 3-iodotoluene instead of 3-chloroiodobenzene. After the usual work-up procedure, the residue was purified by means of automated flash chromatography (ISOLERA®TM-Biotage; gradient Petroleum Ether-EtOAc from 100:3 to 100:7) to give the tile compound as a yellowish oil. Yield: 94%.
$^1$H-NMR: (CDCl$_3$, δ): 1.30 (t, J=6.8 Hz, 6 H), 2.34 (s, 3 H), 3.69 (quin, J=7.8 Hz, 2 H), 3.85 (quin, J=7.7 Hz, 2 H), 5.51 (s, 1 H), 7.16 (d, J=7.6 Hz, 1 H), 7.22 (t, J=7.6 Hz, 1 H), 7.27-7.36 (m, 2 H).

3-(3-methylphenyl)prop-2-ynal (Compound 91b)

The title compound was synthesized following the procedure reported for Compound 31d, but starting from Compound 91a instead of Compound 31c. The crude title compound was used in the next step without further purification.
MS: [M+H]$^+$=145.12
$^1$H-NMR: (CDCl$_3$, δ): 2.39 (s, 3 H), 7.30-7.35 (m, 2 H), 7.40-7.49 (m, 2 H), 9.44 (s, 1 H).

N-hydroxy-3-(3-methylphenyl)prop-2-yn-1-imine (Compound 91c)

The title compound was synthesized following the procedure reported for Compound 31e but starting from Compound 91b instead of Compound 31d. The crude title compound (brownish oil) was used in the next step without further purification.
MS: [M+H]$^+$=160.19
$^1$H-NMR: (CDCl$_3$, δ): mix E/Z 1/2: 2.37 (s, 1.5 H), 2.37 (s, 3 H), 7.04 (s, 1 H), 7.18-7.31 (m, 3 H), 7.31-7.42 (m, 3 H), 7.62 (s, 0.5 H).

N-hydroxy-3-(m-tolyl)prop-2-ynimidoyl chloride (Compound 91d)

The title compound was prepared following the method herein described for Compound 3b, using Compound 91c instead of 3-trimethylsilylprop-2-ynal oxime. The residue was used in the next step without further purification. Yield: 96.4%.

3-[(3-Methylphenyl)ethynyl]-1-oxa-2-azadispiro[4.2.4.2]tetradec-2-ene

The title compound was prepared following the procedure described for Compound 3c, using Compound 91d instead of Compound 3b and Compound 89a instead of Compound 3a. After the usual work-up procedure, the residue was purified by means of automated flash chromatography (ISOLERA®TM-Biotage; gradient Petroleum Ether-EtOAc from 97:3 to 9:1) to give the title compound as a white-yellowish solid. Yield: 55.8%.
MS: [M+H]$^+$=308.28
$^1$H-NMR: (CDCl$_3$, δ): 1.31-1.52 (m, 6 H), 1.53-1.76 (m, 9 H), 1.87 (dd, J=12.0, 3.2 Hz, 2 H), 2.37 (s, 3 H), 2.90 (s, 2 H), 7.17-7.23 (m, 1 H), 7.26 (dd, J=7.6 Hz, 1 H), 7.31-7.38 (m, 2 H).

Example 92

3-[(6-Methoxypyridin-3-yl)ethynyl]-1,9,12-trioxa-2-azadispiro[4.2.4.2]tetradec-2-ene The title product was obtained starting from Compound 70a instead of Compound 3c, following the procedure described for the compound of Example 3, substituting 5-iodo-2-methoxypyridine for 2-bromo-6-methylpyridine. After the usual work-up procedure, the residue was purified by means of automated flash chromatography (SP01®TM-Biotage; gradient Petroleum Ether-EtOAc from 9:1 to 4:6) to give the title compound as a brownish oil solid. Yield: 45%.
MS: [M+H]$^+$=329.23
$^1$H-NMR: (CDCl$_3$, δ): 1.63-1.74 (m, 2 H), 1.77-1.92 (m, 2 H), 1.98-2.11 (m, 4 H), 2.93 (s, 2H), 3.92-4.05 (m, 4 H), 4.00 (s, 3H), 6.77 (d, 1 H), 7.70 (d, 1 H), 8.36 (s, 1 H).

Example 93

3'-[(6-Methylpyridin-2-yl)ethynyl]-4'H-spiro[indene-1,5'-[1,2]oxazol]-3(2H)-one

The title product was obtained by Swern's oxidation as described in Example 83, starting from the compound of Example 88 instead of the compound of Example 82. After the usual work-up procedure, the residue was purified by means of automated flash chromatography (SP01®TM-Biotage; gradient Petroleum Ether-EtOAc from 95:5 to 1:1) to give the title compound as a brownish oil solid. Yield: 50.3%.
MS: [M+H]$^+$=303.21
$^1$H-NMR: (CDCl$_3$, δ): 2.63 (s, 3H), 2.99 (d, 1H) 3.29 (d, 1H), 3.51 (d, 1H), 3.65 (d, 1H), 7.23 (d, 1H), 7.44 (d, 1H), 7.55-7.62 (m, 1H), 7.63-7.72 (m, 2H), 7.76 (d, 1H), 7.80 (d, 1H).

Example 94

N-Methoxy-3-[2-(6-methyl-2-pyridyl)ethynyl]spiro[4H-isoxazole-5,3'-indane]-1'-imine The title product was obtained the method described for the compound of Example 84 starting from the Compound of example 93 instead of the compound of Example 83. After the usual work-up procedure, the residue was purified by means of automated flash chromatography (SP01®TM-Biotage; gradient Petroleum Ether-EtOAc from 95:5 to 1:1) to give the title compound as a yellowish oil. Yield: 82%.

MS: [M+H]$^+$=332.15

$^1$H-NMR: (CDCl$_3$, δ): 2.59 (s, 3H), 3.15 (d, 1H), 3.34-3.45 (m, 2H), 3.49-3.58 (m, 1H), 4.00 (s, 3H), 7.19 (d, 1H), 7.37-7.49 (m, 4H), 7.61 (t, 1H), 7.69-7.74 (m, 1 H).

Example 95

3-[(3-Chlorophenyl)ethynyl]-N,N-dimethyl-1-oxa-2, 7-diazaspiro[4.4]non-2-ene-7-carboxamide To a solution of Compound 27d (0.12 g, 0.46 mmol) in 10 mL of dichloromethane was added TEA (0.02 mL, 1.38 mmol) followed by N,N-dimethylchloroformamide (0.051 mL, 0.59 mmol). The reaction mixture was stirred at r.t. for 4 h. Afterwards, it was evaporated to dryness and purified by means of automated flash chromatography (SP01®TM-Biotage; gradient Petroleum Ether-EtOAc from 3:7 to 0:1) to give the title compound as a pale yellow solid. Yield: 68.8%.

MS: [M+H]$^+$=332.3

$^1$H-NMR: (DMSO-d$_6$, δ): ppm 1.95-2.18 (m, 2 H), 2.75 (s, 6 H), 3.22-3.41 (m, 3 H), 3.41-3.46 (m, 1 H), 3.51 (td, J=10.2, 7.0 Hz, 1 H), 3.58 (d, J=11.7 Hz, 1 H), 7.46-7.53 (m, 1 H), 7.54-7.61 (m, 2 H), 7.68 (t, J=1.7 Hz, 1 H).

Example 96

3-[(3-Chlorophenyl)ethynyl]-1-oxa-2,7-diazaspiro [4.4]non-2-ene-7-carboxamide

To a solution of Compound 27d (0.125 g, 0.48 mmol) in 10 mL of methanol was added trimethylsylylisocyanate (0.097 mL, 0.72 mmol). The reaction mixture was stirred at r.t. for 20 h. Afterwards, it was evaporated to dryness and purified by means of automated RP chromatography (SP01®TM-Biotage; MeCN-ammonium carbonate buffer 38:62) to give the title compound as white solid. Yield: 55%.

MS: [M+H]$^+$=304.3

$^1$H-NMR: (CDCl$_3$, δ): ppm 2.13 (dt, J=13.1, 9.2 Hz, 1 H), 2.33-2.45 (m, 1 H), 3.12-3.20 (m, 1 H), 3.20-3.28 (m, 1 H), 3.55 (d, J=11.5 Hz, 1 H), 3.58-3.68 (m, 2 H), 3.84 (d, J=11.5 Hz, 1 H), 4.44 (br. s., 2 H), 7.32 (t, J=7.8 Hz, 1 H), 7.38-7.45 (m, 2 H), 7.53 (t, J=1.6 Hz, 1 H).

Example 97

9-[(3-Chlorophenyl)ethynyl]-7-oxa-8-azadispiro [3.1.4.1]undec-8-ene

2-Methylidenespiro[3.3]heptane (Compound 97a)

The title compound was prepared following the methodology described for Compound 28a replacing 1-Boc-3-azetidinone with spiro[3.3]heptan-6-one. The reaction crude was used immediately in the next step without further purification.

MS: [M+H]$^+$=108.18

9-[(3-Chlorophenyl)ethynyl]-7-oxa-8-azadispiro [3.1.4.1]undec-8-ene

The title compound was prepared following the procedure described for Compound 3c, using Compound 31e instead of Compound 3b and Compound 97a instead of Compound 3a. After the usual work-up procedure, the residue was purified by means of automated flash chromatography (SP01®TM-Biotage; Petroleum Ether-EtOAc 97:3; then DCM 100%) to give the title compound as a white-yellowish solid. Yield: 20.7%.

MS: [M+H]$^+$=285.77

$^1$H-NMR: (CDCl$_3$, δ): 1.82-1.94 (m, 2 H), 2.02-2.11 (m, 4 H), 2.23-2.32 (m, 2 H), 2.49-2.57 (m, 2 H), 3.15 (s, 2 H), 7.31 (t, J=7.8 Hz, 1 H), 7.34-7.43 (m, 2 H), 7.50-7.54 (m, 1 H).

Example 98

3-[(3-Methylphenyl)ethynyl]-1,9,13-trioxa-2-azadispiro[4.2.5.2]pentadec-2-ene

9-Methylidene-1,5-dioxaspiro[5.5]undecane (Compound 98a)

The title compound was prepared following the methodology described for Compound 28a replacing 1-Boc-3-azetidinone with 7,11-dioxaspiro[5.5]undecan-3-one. After the usual work-up procedure, the residue was purified by means of automated flash chromatography (SP01®TM-Biotage; Et$_2$O) to give the title compound as a pale-yellow oil. Yield: 96.3%.

$^1$H-NMR: (CDCl$_3$, δ): 1.76 (quin, J=5.4 Hz, 2 H), 1.89 (t, J=6.4 Hz, 4 H), 2.23 (t, J=6.2 Hz, 4 H), 3.95 (t, J=5.5 Hz, 4 H), 4.67 (s, 2 H).

3-[(3-Methylphenyl)ethynyl]-1,9,13-trioxa-2-azadispiro[4.2.5.2]pentadec-2-ene

The title compound was prepared following the procedure described for Compound 3c, using Compound 91d instead of Compound 3b and Compound 97a instead of Compound 3a. After the usual work-up procedure, the residue was purified by means of automated flash chromatography (SP01®TM-Biotage; gradient Petroleum Ether-EtOAc from 9:1 to 7:3) to give the title compound as a pasty solid. Yield: 68%.

MS: [M+H]$^+$=325.97

(CDCl$_3$, δ): 1.71-1.82 (m, 4 H), 1.89-2.08 (m, 6 H), 2.37 (s, 3 H), 2.91 (s, 2 H), 3.94 (dt, J=18.5, 5.5 Hz, 4 H), 7.17-7.30 (m, 2 H), 7.30-7.39 (m, 2 H).

Example 99

7-[(3-Chlorophenyl)ethynyl]-5-oxa-6-azaspiro[3.4] oct-6-ene

The title compound was prepared following the procedure described for Compound 3c, using Compound 31f instead of Compound 3b and methylenecyclobutane instead of Compound 3a. After the usual work-up procedure, the residue was purified by means of automated flash chromatography (SP01®TM-Biotage; gradient Petroleum Ether-EtOAc from 1:0 to 9:1) to give the title compound as a pale-yellow solid. Yield: 80.4%.

MS: [M+H]$^+$=245.71

$^1$H-NMR: (CDCl$_3$, δ): 1.58-1.71 (m, 1 H), 1.89 (dtt, J=11.3, 9.9, 9.9, 3.5, 3.5 Hz, 1 H), 2.18-2.28 (m, 2 H), 2.52-

2.64 (m, 2 H), 3.22 (s, 2 H), 7.32 (t, J=7.6 Hz, 1 H), 7.36-7.44 (m, 2 H), 7.52 (t, J=1.6 Hz, 1 H).

Example 100

10-[(3-Chlorophenyl)ethynyl]-2,8-dioxa-9-aza-dispiro[3.2.4.2]tridec-9-ene

Diethyl 4-methylenecyclohexane-1,1-dicarboxylate (Compound 100a)

The title compound was prepared following the method reported herein for Compound 31a. As starting material diethyl 4-oxocyclohexane-1,1-dicarboxylate replaced 1,4-dioxaspiro[4.5]decan-8-one. After the usual work-up procedure the residue was purified by means of automated flash chromatography (SP01®TM-Biotage; gradient Petroleum Ether-EtOAc from 1:0 to 8:2) to give the title compound as a colorless oil. Yield: 88.1%.
MS: $[M+H]^+$=240.30
$^1$H-NMR: (CDCl$_3$, δ): 1.28 (t, J=7.2 Hz, 6 H), 2.05-2.15 (m, 4 H), 2.19-2.27 (m, 4 H), 4.22 (q, J=7.1 Hz, 4 H), 4.68 (s, 2 H).

[1-(Hydroxymethyl)-4-methylene-cyclohexyl]methanol (Compound 100b)

To a suspension of LiAlH$_4$ (0.166 g, 4.4 mmol) in anhydrous Et$_2$O (10 mL) stirred a 0° C. was added a solution of Compound 100a (100 mg, 2.08 mmol) in Et$_2$O (10 mL). The reaction mixture was stirred at r.t. for 2 h. Additional 0.5 equivalents of LiAlH$_4$ were added and the reaction was stirred at r.t. for 1 h. Afterwards, it was quenched, by adding THF/H$_2$O (2 mL:1.3 mL), then 2N HCl (30 mL). Extraction with EtOAc, drying over Na$_2$SO$_4$ and evaporation to dryness afforded a crude, that was purified by means of automated flash chromatography (SP01®TM-Biotage; gradient Dichloromethane-Methanol gradient from 1:0 to 95:5) to give the title compound as a white solid. Yield: 92.1%.
MS: $[M+H]^+$=156.22
$^1$H-NMR: (CDCl$_3$, δ): 1.51 (t, J=6.6 Hz, 4 H), 2.02 (br. s, 2 H), 2.19 (t, J=6.1 Hz, 4 H), 3.70 (s, 4 H), 4.67 (s, 2 H).

[1-(Hydroxymethyl)-4-methylidenecyclohexyl]methyl 4-methylbenzenesulfonate (Compound 100c)

To a suspension of Compound 100b (0.25 g, 1.6 mmol) and pyridine (0.40 mL) in dichloromethane was added at 0° C. a solution of para-toluenesulphonyl chloride (0.336 g, 1.76 mmol) in 1 mL of dichloromethane. The reaction mixture was stirred at 0° C. for 30 min., then at r.t. for 3.5 h. Dilution with dichloromethane, washing with 1M aqueous NaHSO$_4$ and brine, drying with Na$_2$SO$_4$, afforded, after evaporation, a crude which was purified by means of automated flash chromatography (SP01®TM-Biotage; gradient Dichloromethane-Methanol from 1:0 to 95:5) to give the title
MS: $[M+H]^+$=310.41
$^1$H-NMR: (CDCl$_3$, δ): 1.39-1.53 (m, 4 H), 1.98-2.24 (m, 4 H), 2.48 (s, 3 H), 3.57 (s, 2 H), 4.01 (s, 2 H), 4.65 (s, 2 H), 7.38 (m, J=8.1 Hz, 2 H), 7.83 (d, J=8.3 Hz, 2 H).

7-Methylidene-2-oxaspiro[3.5]nonane (Compound 100d)

To a solution of compound 100c (0.320 g, 1.03 mmol) in THF (2 mL) stirred at 0° C. was added sodium hydride (0.082 g, 2.06 mmol). After 30 min. stirring, the mixture was heated at 60° C. for 5 h. After dilution with water, extraction with Et$_2$O and evaporation to dryness, the crude was used in the next step without further purification. Yield: 77.3%.

10-[(3-Chlorophenyl)ethynyl]-2,8-dioxa-9-aza-dispiro[3.2.4.2]tridec-9-ene

The title compound was prepared following the procedure described for Compound 3c, using Compound 31f instead of Compound 3b and Compound 100d instead of Compound 3a. After the usual work-up procedure, the residue was purified by means of automated flash chromatography (Isolera®TM-Biotage; gradient Petroleum Ether-EtOAc from 8:2 to 1:1) to give the title compound as a pale-yellow solid. Yield: 67.6%.
MS: $[M+H]^+$=315.80
$^1$H-NMR: (CDCl$_3$, δ): 1.52-1.69 (m, 2 H), 1.82-1.95 (m, 4 H), 2.01-2.14 (m, 2 H), 2.87 (s, 2 H), 4.45 (d, J=3.4 Hz, 4 H), 7.29-7.35 (m, 1 H), 7.36-7.44 (m, 2 H), 7.51 (t, J=1.6 Hz, 1 H).

Example 101

3-[(4-Chloropyridin-2-yl)ethynyl]-8,8-difluoro-1-oxa-2-azaspiro[4.5]dec-2-ene

3-[(4-Chloropyridin-2-yl)ethynyl]-1-oxa-2-azaspiro[4.5]dec-2-en-8-one (Compound 101a)
The title compound was synthesized starting from the compound of Example 65 (instead of the compound of Example 31) using the method described for the compound of Example 32. The crude was used in the next step without further purification.
MS: $[M+H]^+$=289.7
$^1$H-NMR: (CDCl$_3$, δ): ppm 1.97-2.10 (m, 2 H), 2.24-2.45 (m, 4 H), 2.74-2.90 (m, 2 H), 3.05 (s, 2 H), 7.36 (dd, J=5.4, 2.0 Hz, 1 H), 7.59 (d, J=1.5 Hz, 1 H), 8.55 (d, J=5.4 Hz, 1 H).

3-[(4-Chloropyridin-2-yl)ethynyl]-8,8-difluoro-1-oxa-2-azaspiro[4.5]dec-2-ene

Into a solution of Compound 101a (0.085 g, 0.29 mmol), 5 mL of dichloromethane stirred at r.t. under a nitrogen stream was added dropwise diethylaminosulphurtrifluoride (0.163 mL, 1.23 mmol). Stirring was continued overnight, afterwards a saturated aqueous solution of NaHCO$_3$ (5 ml) was added, extracting with DCM (3×5 mL), drying the organic layer with Na$_2$SO$_4$ and evaporating to dryness. The residue was purified by means of automated flash chromatography (Isolera®TM-Biotage; gradient Petroleum Ether-EtOAc from 95:5 to 6:4) to give the title compound as a yellow oil containing a main impurity. This oil was purified again using RP chromatography (Isolera®TM-Biotage; aq. NH$_4$HCO$_3$/AcCN 55:45) affording the title compound a yellowish-white solid. Yield: 14.2%.
MS: $[M+H]^+$=311.4
$^1$H-NMR: (CDCl$_3$, δ): ppm 1.82-1.96 (m, 2 H), 2.02-2.14 (m, 4 H), 2.14-2.35 (m, 2 H), 2.98 (s, 2 H), 7.37 (dd, J=5.4, 2.0 Hz, 1 H), 7.59 (d, J=1.5 Hz, 1 H), 8.55 (d, J=5.4 Hz, 1 H).

Example 102

Ethyl 3-[(6-methylpyridin-2-yl)ethynyl]-1-oxa-2-azaspiro[4.5]dec-2-ene-8-carboxylate Ethyl 4-methylidenecyclohexanecarboxylate (Compound 102a)

This intermediate was prepared following the procedure described Compound 31a. As starting material ethyl 4-oxocyclohexane-1-carboxylate replaced 1,4-dioxaspiro[4.5]decan-8-one. After the usual work-up procedure, the residue was purified by means of automated flash chromatography (SP01®TM-Biotage; gradient Petroleum Ether-EtOAc from 95:5 to 4:6) to give the title compound as a colorless oil. Yield: 68.7%.

MS: $[M+H]^+=169.50$

Ethyl 3-[(trimethylslyl)ethynyl]-1-oxa-2-azaspiro [4.5]dec-2-ene-8-carboxylate (Compound 102b)

The title compounds were synthesized using the same method described above for Compound 3c, but replacing Compound 102a for Compound 3a. The crude was purified by automated flash chromatography (Isolera®TM-Biotage; gradient Petroleum Ether-EtOAc from 98:2 to 40:60) to give the title compound as colorless oil. Yield: 49.3%.

MS: $[M+H]^+=308.55$

Ethyl 3-[(6-Methylpyridin-2-yl)ethynyl]-1-oxa-2-azaspiro[4.5]dec-2-ene-8-carboxylate The title compound was synthesized following the procedure described for the compound of Example 3, replacing Compound 102b for Compound 3c. The residue was purified by means of automated RP chromatography (Isolera®TM-Biotage; aq. $NH_4HCO_3$/AcCN 55:45) affording the title compound. Yield: 29%.

MS: $[M+H]^+=327.16$ $^1$H-NMR: (CDCl$_3$, δ): 1.29 (t, 3H), 1.60-1.72 (m, 2H) 1.74-1.84 (m, 2H), 1.84-1.92 (m, 2H), 2.09 (dt, 2H), 2.42-2.51 (m, 1H), 2.62 (s, 3H), 2.96 (s, 2H), 4.17 (q, 2H), 7.20 (d, 1H), 7.39 (d, 1H), 7.63 (t, 1H).

Example 103

3'-[(3-Chlorophenyl)ethynyl]-1H,4'H-1-spiro[isochromene-4,5'-[1,2]oxazole]

4-methyleneisochromane (Compound 103a)

This intermediate was prepared following the procedure described Compound 31a. As starting material isochroman-4-one replaced 1,4-dioxaspiro[4.5]decan-8-one. After the usual work-up procedure the residue was purified by means of automated flash chromatography (SP01®TM-Biotage; gradient Petroleum Ether-EtOAc from 1:0 to 0:1) to give the title compound as a colorless oil. Yield: 69.8%.

MS: $[M+H]^+=146.19$ $^1$H-NMR: (CDCl$_3$, δ): 4.48 (s, 2 H), 4.84 (s, 2 H), 5.04 (s, 1 H), 5.63 (s, 1 H), 7.02-7.09 (m, 1 H), 7.22-7.28 (m, 2 H), 7.67-7.75 (m, 1 H).

3'-[(3-Chlorophenyl)ethynyl]-1H,4'H-spiro[isochromene-4,5'-[1.2]oxazole]

The title compound was prepared following the procedure described for Compound 3c, using Compound 31f instead of Compound 3b and Compound 103a instead of Compound 3a. After the usual work-up procedure, the residue was purified by means of automated flash chromatography (SP01®TM-Biotage; Petroleum Ether-EtOAc from 97:3) followed by automated RP chromatography (SP01®TM-Biotage; gradient aq. $NH_4HCO_3$/AcCN from 40:60 to 20:80) affording the title compound. Yield: 15.8%.

MS: $[M+H]^+=323.78$ $^1$H-NMR: (DMSO-d$_6$, δ): 3.36-3.43 (m, 1 H), 3.46-3.54 (m, 1 H), 3.86 (d, J=12.0 Hz, 1 H), 3.96 (d, J=12.0 Hz, 1 H), 4.69-4.77 (m, 1 H), 4.77-4.85 (m, 1 H), 7.11-7.18 (m, 1 H), 7.31-7.38 (m, 2 H), 7.43-7.54 (m, 2 H), 7.56-7.62 (m, 2 H), 7.71 (t, J=1.7 Hz, 1 H).

Example 104

{3-[(3-Chlorophenyl)ethynyl]-1-oxa-2,7-diazaspiro [4.4]non-2-en-7-yl}(4-methyl piperazin-1-yl)methanone To a solution of Compound 27d (150 mg, 0.58 mmol) in dichloromethane (10 mL) was added TEA (0.248 mL, 1.73 mmol) followed by 4-methyl-1-piperazinecarbonyl chloride (122 mg, 0.748 mmol). The reaction mixture was kept under stirring for 20 h. After evaporation the residue was purified by means of automated isocratic RP chromatography (SP01®TM-Biotage; $NH_4HCO_3$/AcCN 55:45) affording 91 mg of the title compound as a gummy oil. Yield: 49%.

MS: $[M+H]^+=357.44$ $^1$H-NMR: (DMSO-d$_6$, δ): ppm 1.98-2.15 (m, 2 H), 2.18 (s, 3 H), 2.22-2.37 (m, 4 H), 3.08-3.17 (m, 2 H), 3.17-3.23 (m, 2 H), 3.23-3.41 (m, 3 H), 3.45 (d, J=11.7 Hz, 1 H), 3.53 (td, J=10.2, 7.0 Hz, 1 H), 3.60 (d, J=12.0 Hz, 1 H), 7.46-7.53 (m, 1 H), 7.54-7.61 (m, 2 H), 7.66-7.71 (m, 1 H).

Example 105

1-({3-[(3-Chlorophenyl)ethynyl]-1-oxa-2,7-diazaspiro[4.4]non-2-en-7-yl}carbonyl)imidazolidin-2-one The title compound was synthesized using the method described for the compound of Example 104, replacing 1-chlorocarbonyl-2-imidazolidinone for by 4-methyl-1-piperazinecarbonyl chloride. After evaporation, the crude was purified by means of automated flash chromatography (SP01®TM-Biotage; gradient EtOAc-MeOH from 95:5 to 8:2) to afford a yellowish solid. Yield: 51.3%.

MS: $[M+H]^+=373.3$ $^1$H-NMR: (DMSO-d$_6$, δ): ppm 2.04-2.23 (m, 2 H), 3.21-3.42 (m, 4 H), 3.49-3.79 (m, 6 H), 7.22 (s, 1 H), 7.46-7.53 (m, 1 H), 7.54-7.61 (m, 2 H), 7.66-7.71 (m, 1 H).

Example 106

[7-[2-(3-Chlorophenyl)ethynyl]-9-oxa-3,8-diazaspiro [4.4]non-7-en-3-yl]-pyrrolidin-1-yl-methanone The title compound was synthesized using the method described for the compound of Example 104, replacing 1-pyrrolidincarbonyl chloride for 4-methyl-1-piperazinecarbonyl chloride. After the usual work-up procedure, the crude was purified by means of automated flash chromatography (SP01®TM-Biotage; CHCl$_3$-1.4N methanolic ammonia 100: 0.5) to afford an ivory solid. Yield: 72.8%.

MS: $[M+H]^+=358.35$ $^1$H-NMR: (CDCl$_3$, δ): 1.77-1.96 (m, 4 H), 2.01 (dt, J=13.0, 9.2 Hz, 1 H), 2.32 (ddd, J=12.9, 6.7, 3.2 Hz, 1 H), 3.13 (d, J=17.1 Hz, 1 H), 3.23 (d, J=17.4 Hz, 1 H), 3.34-3.49 (m, 4 H), 3.58-3.65 (m, 1 H), 3.71 (s, 2 H), 3.66-3.76 (m, 1 H), 7.32 (t, J=8.1 Hz, 1 H), 7.37-7.45 (m, 2 H), 7.53 (t, J=1.7 Hz, 1 H).

Example 107

[7-[2-(3-Chlorophenyl)ethynyl]-9-oxa-3,8-diazaspiro[4.4]non-7-en-3-yl]-(1-piperidyl)methanone The title compound was synthesized using the method described for the compound of Example 104, replacing 1-piperidinecarbonyl chloride for 4-methyl-1'-piperazinecarbonyl chloride. After the usual work-up procedure, the crude was purified by means of automated flash chromatography (SP01®TM-Biotage; gradient petroleum ether-EtOAc 7:3 to 3:7) to afford a yellowish oil. Yield: 37.4%.

MS: [M+H]$^+$=372.3

$^1$H-NMR: (CDCl$_3$, δ): ppm 1.50-1.69 (m, 6 H), 1.99 (dt, J=13.0, 9.0 Hz, 1 H), 2.24-2.34 (m, 1 H), 3.07-3.17 (m, 1 H), 3.17-3.33 (m, 5 H), 3.56 (ddd, J=10.6, 8.2, 2.9 Hz, 1 H), 3.60-3.65 (m, 1 H), 3.65-3.72 (m, 1 H), 3.72-3.77 (m, 1 H), 7.32 (t, J=7.8 Hz, 1 H), 7.38-7.44 (m, 2 H), 7.53 (t, J=1.7 Hz, 1 H).

Example 108

1-[7-[2-(3-Chlorophenyl)ethynyl]-9-oxa-3,8-diazaspiro[4.4]non-7-ene-3-carbonyl]-3-methylsulfonylimidazolidin-2-one The title compound was synthesized using the method described for the compound of Example 104, replacing 1-chlorocarbonyl-3-methanesulfonyl-2-imidazolidinone for 4-methyl-1-piperazinecarbonyl chloride. After evaporation, the crude was purified by means of automated flash chromatography (SP01®TM-Biotage; gradient petroleum ether-EtOAc 1:1 to 1:9) to afford a grey solid. Yield: 67.3%.

MS: [M+H]$^+$=451.3

$^1$H-NMR: (CDCl$_3$, δ): ppm 2.08-2.23 (m, 1 H), 2.40 (dd, J=13.0, 6.8 Hz, 1 H), 3.12-3.27 (m, 2 H), 3.34 (s, 3 H), 3.62-4.10 (m, 8 H), 7.33 (t, J=8.3 Hz, 1 H), 7.42 (t, J=6.6 Hz, 2 H), 7.53 (s, 1 H).

Example 109

3-[(3-Chlorophenyl)ethynyl]-N-ethyl-N-(propan-2-yl)-1-oxa-2,7-diazaspiro[4.4]non-2-ene-7-carboxamide A solution of Compound 27d (100 mg, 0.38 mmol) and DIPEA (0.074 mL, 0.07 mmol) in 4 ml of CH$_2$Cl$_2$ is dripped over a period of 45 min r.t. in a trifosgene (39.9 mg, 0.13 mmol) solution in CH$_2$Cl$_2$ (1 mL). The reaction was stirred for 10 min. Then it was added dropwise into a solution of ethylisoprylamine (0.070 mL, 0.576 mmol) and DIPEA (0.074 mL, 0.07 mmol) in CH$_2$Cl$_2$ (1 mL). After overnight resting, the reaction was concentrated under reduced pressure and the crude was purified by by means of automated flash chromatography (SP01®TM-Biotage; gradient petroleum ether-EtOAc 8:21 to 4:6) obtaining 25 mg as a yellow thick oil. Yield: 17.4%

MS: [M+H]$^+$=373.88

$^1$H-NMR: (CDCl$_3$, δ): 1.15 (t, J=7.1 Hz, 3 H), 1.19 (d, J=6.6 Hz, 3 H), 1.24 (d, J=6.6 Hz, 3 H), 2.02 (dt, J=13.1, 9.1 Hz, 1 H), 2.26-2.36 (m, 1 H), 3.06 (dq, J=14.2, 7.1 Hz, 1 H), 3.11-3.34 (m, 3 H), 3.54-3.62 (m, 1 H), 3.62-3.78 (m, 3 H), 3.96 (quin, J=6.7 Hz, 1 H), 7.29-7.36 (m, 1 H), 7.41 (t, J=7.6 Hz, 2 H), 7.50-7.55 (m, 1 H).

Example 110

7-[2-(3-Chlorophenyl)ethynyl]-N-methoxy-N-methyl-9-oxa-3,8-diazaspiro[4.4]non-7-ene-3-carboxamide The title compound was synthesized using the method described for the compound of Example 104, replacing N-methoxy-N-methylcarbamoyl chloride for 4-methyl-1-piperazinecarbonyl chloride. After evaporation, the crude was purified by means of automated flash chromatography (SP01®TM-Biotage; gradient petroleum ether-EtOAc 8:2 to 4:6) to afford a pale yellow solid. Yield: 54.1%.

MS: [M+H]$^+$=348.3

$^1$H-NMR: (CDCl$_3$, δ): ppm 1.98-2.09 (m, 1 H), 2.34 (dddd, J=12.9, 6.6, 3.2, 1.5 Hz, 1 H), 3.06 (s, 3 H), 3.15 (d, J=17.4 Hz, 1 H), 3.23 (d, J=16.9 Hz, 1 H), 3.63 (s, 3 H), 3.67 (d, J=12.2 Hz, 1 H), 3.69-3.82 (m, 2 H), 3.85 (dd, d=12.2, 1.5 Hz, 1 H), 7.30-7.35 (m, 1 H), 7.38-7.45 (m, 2 H), 7.53 (t, J=1.7 Hz, 1 H).

Example 111

7-[2-(3-Chlorophenyl)ethynyl]-N-(4-pyridyl)-9-oxa-3,8-diazaspiro[4.4]non-7-ene-3-carboxamide The title compound was synthesized using the method described for the compound of Example 109, replacing 4-aminopyridine for ethylisopropylamine. After the usual work-up procedure evaporation, the crude was purified by means of automated flash chromatography (SP01®TM-Biotage; gradient EtOAc-MeOH/NH$_3$ from 98:2 to 85:15) to afford a pale yellow solid. Yield: 16.4%.

MS: [M+H]$^+$=381.3

$^1$H-NMR: (CDCl$_3$, δ): ppm 2.20 (dt, J=13.1, 9.4 Hz, 1 H), 2.43-2.54 (m, 1 H), 3.16-3.25 (m, 1 H), 3.25-3.34 (m, 1 H), 3.70 (d, J=11.7 Hz, 1 H), 3.77-3.86 (m, 2 H), 4.02 (d, J=10.5 Hz, 1 H), 7.30-7.37 (m, 1 H), 7.39-7.46 (m, 2 H), 7.50-7.57 (m, 1 H), 7.66 (d, J=5.6 Hz, 2 H), 8.40 (d, J=5.9 Hz, 2 H).

Example 112

Ethyl 3-[(3-chlorophenyl)ethynyl]-1-oxa-2,7-diazaspiro[4.4]non-2-ene-7-carboxylate The title compound was synthesized using the method described for the compound of Example 104, replacing ethyl chloroformate for 4-methyl-1-piperazinecarbonyl chloride. After evaporation, the crude was purified by means of automated flash chromatography (SP01®TM-Biotage; gradient petroleum ether-EtOAc 9:1 to 1:1) to afford a pale yellow oil. Yield: 67.3%.

MS: [M+H]$^+$=332.79

$^1$H-NMR: (DMSO-d$_6$, δ): 1.19 (t, J=6.7 Hz, 3 H), 2.15 (br. s., 2 H), 3.17-3.28 (m, 1 H), 3.32-3.44 (m, 2 H), 3.44-3.63 (m, 3 H), 4.05 (q, J=6.6 Hz, 2 H), 7.46-7.53 (m, 1 H), 7.54-7.60 (m, 2 H), 7.68 (s, 1 H).

Example 113

8,8-Difluoro-2-[2-(6-methyl-2-pyridyl) ethynyl]-4-oxa-3-azaspiro[4.5]dec-2-ene 2-(8,8-difluoro-4-oxa-3-azaspiro[4.5]dec-2-en-2-yl) ethynyl-trimethylsilane (Compound 113a)

The title compound was synthesised following the method described here for Compound 3c, using Compound 90a instead of Compound 3a. After the usual work-up procedure, the crude product was purified by automated flash chromatography (Horizon®TM-Biotage) eluting with a Petroleum Ether-EtOAc gradient from 99:1 to 95:5, yielding the title compound. Yield: 34.1%.

8,8-Difluoro-2-[2-(6-methyl-2-pyridyl)ethynyl]-4-oxa-3-azaspiro[4.5]dec-2-ene The title compound was prepared following the procedure reported for the compound of Example 3, but replacing Compound 113a for Compound 3c. After the usual work-up, the crude was purified by automated flash chromatography (SP01®TM-Biotage; gradient Petroleum Ether-EtOAc from 9:1 to 7:3) affording the title product as yellow solid. Yield: 36.5%.

MS: $[M+H]^+=291.39$ $^1$H-NMR: (CDCl$_3$, δ): 1.78-1.94 (m, 2 H), 2.01-2.12 (m, 4 H), 2.12-2.35 (m, 2 H), 2.62 (s, 3 H), 2.98 (s, 2 H), 7.21 (d, J=7.8 Hz, 1 H), 7.40 (d, J=7.6 Hz, 1 H), 7.64 (t, J=7.8 Hz, 1 H).

Example 114

6-[2-(3-Chlorophenyl)ethynyl]-2,8-dioxa-7-azaspiro[3.4]oct-6-ene

3-Methyleneoxetane (Compound 114a)

The title compound was prepared following the methodology described for Compound 28a, replacing 1-Boc-3-azetidinone with 3-oxetanone. The reaction crude was used in the next step without further purification.

6-[2-(3-Chlorophenyl)ethynyl]-2,8-dioxa-7-azaspiro[3.4]oct-6-ene

The title compound was prepared following the procedure described for Compound 3c, using Compound 31f instead of Compound 3b and Compound 114a instead of Compound 3a. After the usual work-up procedure, the residue was purified by means of automated flash chromatography (SP01®TM-Biotage; gradient Petroleum Ether-EtOAc from 90:10 to 75:25), followed by automated RP chromatography (SP01®TM-Biotage; eluent aq. (NH$_4$)$_2$CO$_3$ 1.6 g/l-AcCN 1:1, affording the title compound as a yellow solid. Yield: 3.7% from 3-oxetanone.

MS: $[M+H]^+=248.38$ $^1$H-NMR: (CDCl$_3$, δ): 3.49 (s, 2 H), 4.73 (d, J=7.8 Hz, 2 H), 5.05 (d, J=8.1 Hz, 2 H), 7.32 (t, J=7.8 Hz, 1 H), 7.38-7.44 (m, 2 H), 7.50-7.55 (m, 1 H).

Example 115

2-[2-(3-Chlorophenyl)ethynyl]-4-oxa-3-azaspiro[4.5]dec-2-ene

The title compound was prepared following the procedure described for Compound 3c, using Compound 31f instead of Compound 3b and 1-methylenecyclohexane instead of Compound 3a. After the usual work-up procedure, the residue was purified by means of automated flash chromatography (SP01®TM-Biotage; gradient Petroleum Ether-EtOAc from 1:0 to 9:1). Another purification was required to obtain pure title compound, carried with a gradient Petroleum Ether-Et2O from 1:0 to 9:1. Yield: 90.5%.

MS: $[M+H]^+=273.76$ $^1$H-NMR: (DMSO-d$_6$, δ): 1.33-1.54 (m, 4 H), 1.54-1.73 (m, 6 H), 2.98 (s, 2 H), 7.48 (t, J=7.8 Hz, 1 H), 7.51-7.59 (m, 2 H), 7.66 (t, J=1.6 Hz, 1 H).

Example 116

2-[2-(3-Chlorophenyl)ethynyl]-8-(difluoromethylene)-4-oxa-3-azaspiro[4.5]dec-2-ene A solution of tris-dimethylaminophosphine in 2.6 mL of anhydrous THF was added under a nitrogen atmosphere to a solution of dibromodifluoromethane in 3.9 mL of anhydrous THF at 0° C. over 15 min. The reaction mixture was stirred at r.t. for 30 min. Afterwards, a solution of the Compound of Example 32 (0.275 g, 0.956 mmol) was added dropwise. After overnight resting, the solution was evaporated and taken up with EtOAc. Washing with water, drying the organic layer with Na$_2$SO$_4$ and evaporating to dryness in vacuo afforded a crude which was purified by means of automated flash chromatography (Isolera®TM-Biotage; gradient Petroleum Ether-EtOAc from 95:5 to 8:2) giving 42 mg of the title compound. Yield: 13.7%.

MS: $[M+H]^+=322.20$ $^1$H-NMR: (DMSO-d$_6$, δ): 1.65-1.86 (m, 4 H), 2.11-2.30 (m, 4 H), 3.05 (s, 2 H), 7.49 (t, J=7.8 Hz, 1 H), 7.52-7.60 (m, 2 H), 7.65-7.69 (m, 1H).

Example 117

2-[2-(3-Chlorophenyl)ethynyl]-4-oxa-3,8-diazaspiro[4.5]dec-2-ene-8-carboxamide The title compound was synthesized following the method herein described for the compound of Example 96 but replacing Compound 22c for Compound 27d. After the usual work-up procedure the crude was purified by means of automated flash chromatography (Isolera®TM-Biotage; gradient Petroleum Ether-EtOAc from 1:0 to 93:7) giving the title compound as a white solid. Yield: 76.9%.

MS: $[M+H]^+=318.25$ $^1$H-NMR: (DMSO-d$_6$, δ): 1.64-1.72 (m, 4 H) 3.06 (s, 2 H) 3.31-3.46 (m, 4 H) 5.98 (s, 2 H) 7.49 (t, J=8.1 Hz, 1 H) 7.53-7.59 (m, 2 H) 7.65-7.74 (m, 1 H).

Example 118

[2-[2-(3-Chlorophenyl)ethynyl]-4-oxa-3,8-diazaspiro[4.5]dec-2-en-8-yl]-(2-furyl)methanone The title compound was synthesized following the method herein described for the compound of Example 96, but replacing Compound 22c for Compound 27d and 2-furoyl chloride for methylisocyanate. After the usual work-up procedure the crude was purified by means of automated flash chromatography (Isolera®TM-Biotage; gradient Petroleum Ether-EtOAc from 95:5 to 8:2) giving 105 mg of the title compound. Yield: 60.2%.

MS: $[M+H]^+=369.30$ $^1$H-NMR: (DMSO-d$_6$, δ): 1.84 (t, J=5.6 Hz, 4 H), 3.12 (s, 2 H), 3.66 (br. s., 2 H), 3.75-3.90 (m, 2 H), 6.63 (dd, J=3.4, 1.7 Hz, 1 H), 7.00 (d, J=3.4 Hz, 1 H), 7.49 (t, J=8.3 Hz, 1 H), 7.53-7.62 (m, 2 H), 7.68 (t, J=1.6 Hz, 1 H), 7.84 (d, J=1.0 Hz, 1 H).

Example 119

2-[2-(3-Chlorophenyl)ethynyl]-N-methoxy-N-methyl-4-oxa-3,8-diazaspiro[4.5]dec-2-ene-8-carboxamide The title compound was synthesized using the method described for the compound of Example 110, replacing Compound 22c for Compound 27d. After evaporation, the crude was purified by means of automated flash chromatography (Isolera®TM-Biotage; gradient petroleum ether-EtOAc 8:2 to 6:4) to afford a pale yellow oil. Yield: 74%.

MS: [M+H]$^+$=362.30

$^1$H-NMR: (DMSO-d$_6$, δ): 1.76 (t, J=5.6 Hz, 4 H), 2.84 (s, 3 H), 3.08 (s, 2 H), 3.36-3.49 (m, 4 H), 3.54 (s, 3 H), 7.49 (t, J=7.8 Hz, 1 H), 7.53-7.59 (m, 2 H), 7.67 (t, J=1.7 Hz, 1 H).

Example 120

2-[2-(3-Chlorophenyl)ethynyl]-N,N-diethyl-4-oxa-3,8-diazaspiro[4.5]dec-2-ene-8-carboxamide The title compound was synthesized following the method herein described for the compound of Example 96 but replacing Compound 22c for Compound 27d and N,N-diethyl chloroformamide for methylisocyanate. After the usual work-up procedure the crude was purified by means of automated flash chromatography (Isolera®TM-Biotage; gradient Petroleum Ether-EtOAc from 8:2 to 6:4) giving the title compound. Yield: 47.1%.

MS: [M+H]$^+$=374.34

$^1$H-NMR: (DMSO-d$_6$, δ): 1.05 (t, J=7.0 Hz, 6 H), 1.75 (t, J=5.6 Hz, 4 H), 3.06 (s, 2 H), 3.08-3.17 (m, 6 H), 3.17-3.25 (m, 2 H), 7.49 (t, J=7.8 Hz, 1 H), 7.52-7.60 (m, 2 H), 7.65-7.69 (m, 1 H).

Example 121

(3-Chlorophenyl)-[2-[2-(3-chlorophenyl)ethynyl]-4-oxa-3,8-diazaspiro[4.5]dec-2-en-8-yl]methanone The title compound was synthesized following the method herein described for the compound of Example 96 but replacing Compound 22c for Compound 27d and 3-chlorobenzoyl chloride for methyl isocyanate. After the usual work-up procedure the crude was purified by means of automated flash chromatography (Isolera®TM-Biotage; gradient Petroleum Ether-EtOAc from 8:2 to 6:4) giving 122 mg of the title compound a s a pale yellow oil. Yield: 67.5%.

MS: [M+H]$^+$=413.25

$^1$H-NMR: (DMSO-d$_6$, δ): 1.82 (br. s., 4 H), 3.10 (br. s., 2 H), 3.33-3.66 (m, 3 H), 3.83 (br. s., 1 H), 7.36-7.41 (m, 1 H), 7.45-7.61 (m, 6 H), 7.67 (t, J=1.6 Hz, 1 H).

Example 122

Ethyl 2-[2-(3-chlorophenyl)ethynyl]-4-oxa-3,8-diazaspiro[4.5]dec-2-ene-8-carboxylate The title compound was synthesized following the method herein described for the compound of Example 112 but replacing Compound 22c for Compound 27d. After the usual work-up procedure the crude was purified by means of automated flash chromatography (Isolera®TM-Biotage; gradient Petroleum Ether-EtOAc from 9:1 to 8:2) giving the title compound as a white solid. Yield: 55.4%.

MS: [M+H]$^+$=347.27

$^1$H-NMR: (DMSO-d$_6$, δ): 1.19 (t, J=7.1 Hz, 3 H), 1.73 (t, J=5.7 Hz, 4 H), 3.07 (s, 2 H), 3.37-3.55 (m, 4 H), 4.05 (q, J=7.1 Hz, 2 H), 7.49 (t, J=8.6 Hz, 1 H), 7.53-7.61 (m, 2 H), 7.67 (t, J=1.7 Hz, 1 H).

Example 123

[2-[2-(3-Chlorophenyl)ethynyl]-4-oxa-3,8-diazaspiro[4.5]dec-2-en-8-yl]-pyrrolidin-1-yl-methanone The title compound was synthesized following the method herein described for the compound of Example 106 but replacing Compound 22d for Compound 27c. After the usual work-up procedure the crude was purified by means of automated flash chromatography (Isolera®TM-Biotage; gradient Petroleum Ether-EtOAc from 7:3 to 3:7) giving 52 mg of the title compound giving pale yellow solid. Yield: 72.6%.

MS: [M+H]$^+$=372.42

$^1$H-NMR: (DMSO-d$_6$, δ): 1.67-1.83 (m, 8 H), 3.07 (s, 2 H), 3.15-3.29 (m, 8 H), 7.49 (t, J=7.8 Hz, 1 H), 7.52-7.61 (m, 2 H), 7.67 (t, J=1.7 Hz, 1 H).

Example 124

2-[2-(3-Chlorophenyl)ethynyl]-N,N-dimethyl-4-oxa-3,8-diazaspiro[4.5]dec-2-ene-8-carboxamide The title compound was synthesized following the method herein described for the compound of Example 95 but replacing Compound 22d for Compound 27c. After the usual work-up procedure the crude was purified by means of automated flash chromatography (Isolera®TM-Biotage; gradient Petroleum Ether-EtOAc from 3:7 to 0:1) giving pale yellow solid of the title compound. Yield: 66.2%.

MS: [M+H]$^+$=346.29

$^1$H-NMR: (DMSO-d$_6$, δ): 1.75 (t, J=5.5 Hz, 4 H), 2.75 (s, 6 H), 3.07 (s, 2 H), 3.10-3.27 (m, 4 H), 7.49 (t, J=7.6 Hz, 1 H), 7.53-7.60 (m, 2 H), 7.67 (t, J=1.6 Hz, 1 H).

Example 125

Tert-butyl 2-[2-(3-chlorophenyl)ethynyl]-9-methoxy-4-oxa-3,7-diazaspiro[4.4]non-2-ene-7-carboxylate

Tert-butyl 3-methoxy-4-methylenepyrrolidine-1-carboxylate (Compound 125a)

A solution of tert-butyl 3-hydroxy-4-methylenepyrrolidine-1-carboxylate (0.257 g, 1.29 mmol; prepared as described by Alcaraz, Lilian; Cridland, Andrew; Kinchin, Elizabeth Organic Letters, 2001, vol. 3, #25 p. 4051-4054) in 8 mL of THF, stirred at r.t. under a nitrogen atmosphere was added NaH. After 0.5 h stirring at r.t., methyl iodide (0.057 g, 1.42 mmol) was added and the resulting mixture stirred at r.t. for 2 h. After overnight resting, the reaction was quenched with water, extracted with EtOAc which was washed with brine, dried over Na$_2$SO4 and evaporated to dryness affording a crude, purified by means of automated flash chromatography (SP01®TM-Biotage; gradient Petroleum Ether-EtOAc from 9:1 to 7:3) giving 165 mg of the title compound. Yield: 60%.

MS: [M+H]$^+$=391.42

Tert-butyl 2-[2-(3-chlorophenyl)ethynyl]-9-methoxy-4-oxa-3,7-diazaspiro[4.4]non-2-ene-7-carboxylate The title compound was prepared following the procedure described for Compound 3c, using Compound 31f instead of Compound 3b and Compound 125a instead of Compound 3a. After the usual work-up procedure, the residue was purified by means of automated flash chromatography (Isolera®TM-Biotage; gradient Petroleum Ether-EtOAc from 8:2 to 1:1) to give the title compound as a pale-yellow solid. Yield: 67.6%.

MS: [M+H]$^+$=391.42

$^1$H-NMR: (DMSO-d$_6$, δ): 1.42 (s, 9 H), 3.22-3.28 (m, 1 H), 3.33 (s, 3 H), 3.35-3.57 (m, 5 H), 3.75 (br. s., 1 H), 7.50 (t, J=7.6 Hz, 1 H), 7.54-7.61 (m, 2 H), 7.70 (t, J=1.6 Hz, 1 H).

Example 126

Ethyl 2-[2-(3-chlorophenyl)ethynyl]-9-methoxy-4-oxa-3,7-diazaspiro[4.4]non-2-ene-7-carboxylate 2-[2-(3-Chlorophenyl)ethynyl]-9-methoxy-4-oxa-3,7-diazaspiro[4.4]non-2-ene (Compound 126a)

The title compound was synthesized following the method reported for the Compound 1c, substituting Compound 1b with the compound of Example 125 and using chloroform as the solvent. The crude residue was used without further purification in the next reaction.

MS: [M+H]$^+$=291.24

Ethyl 2-[2-(3-chlorophenyl)ethynyl]-9-methoxy-4-oxa-3,7-diazaspiro[4.4]non-2-ene-7-carboxylate The title compound was synthesized following the method herein described for the compound of Example 112 but replacing Compound 126a for Compound 27d. After the usual work-up procedure the crude was purified by means of automated flash chromatography (SP01®TM-Biotage; gradient Petroleum Ether-EtOAc from 8:2 to 1:1) giving the title compound. Yield: 52.6%.

MS: [M+H]$^+$=363.43

$^1$H-NMR: (CDCl$_3$, δ): 1.29 (q, J=6.6 Hz, 3 H), 3.00 (dd, J=17.9, 12.5 Hz, 1 H), 3.42 (s, 3 H), 3.50-3.84 (m, 6 H), 4.12-4.23 (m, 2 H), 7.33 (t, J=7.6 Hz, 1 H), 7.38-7.45 (m, 2 H), 7.54 (t, J=1.5 Hz, 1 H).

Example 127

Affinity of Selected Antagonists for mGlu5 Receptor Subtype

Radioligand Binding Assay at Metabotropic Glutamate Receptor 5 in Rat Brain.

Methods a) Membrane preparation: male Sprague Dawley rats (200-300 g, Charles River, Italy) were killed by cervical dislocation and the forebrain (cortex, striatum and hippocampus) was homogenized (2×20 sec) in 50 vols of cold 50 mM Tris buffer pH 7.4, using a Politron homogenizer (Kinematica). Homogenates were centrifuged at 48000×g for 15 min, resuspended in 50 vols of the same buffer, incubated at 37° C. for 15 min and centrifuged and resuspended two more times. The final pellets were frozen and stored at −80° C. until use.

b) Binding assay: pellets from rat forebrain were resuspended in 100 vols of 20 mM HEPES, 2 mM MgCl$_2$, 2 mM CaCl$_2$, pH 7.4. The membranes were incubated in a final volume of 1 ml for 60 min at 25° C. with 4 nM [$^3$H]MPEP in the absence or presence of competing drugs. Non-specific binding was determined in the presence of 10 μM MPEP (Spooren W. et al., Trends Pharmacol Sci. 22, 331-337, 2001). The incubation was stopped by the addition of cold Tris buffer pH 7.4 and rapid filtration through 0.5% polyethyleneimine pretreated Filtermat 1204-401 (Wallac) filters. The filters were then washed with cold buffer and the radioactivity retained on the filters was counted by liquid scintillation spectrometry.

c) Data Analysis: the inhibition of specific binding of the radioligands by the tested compounds was analyzed to estimate the inhibitory concentration 50% (IC$_{50}$) value by using the non-linear curve-fitting software Prism 4.0 (Graphpad, San Diego, Calif.). The IC$_{50}$ value was converted to an affinity constant (Ki) by the equation of Cheng & Prusoff (Cheng, Y. C. & Prusoff, W. H. Biochem. Pharmacol. 22, 3099-3108, 1973).

Results

The affinity (Ki) of the compounds of the instant invention for mGlu5 receptor is between 0.1 and 1000 nM. For instance, Compound of Example 12 has a Ki of 3.88 nM and Compound of Example 110 has a Ki of 1.49 nM.

Example 128

Affinity of Selected Antagonists for mGlu1 Receptor Subtype

Radioligand Binding Assay at Metabotropic Glutamate Receptor 1 in Rat Brain.

Methods a) Membrane preparation: male Sprague Dawley rats (200-300 g, Charles River, Italy) were killed by cervical dislocation and the cerebella were homogenized (2×20 sec) in 50 vols of cold 50 mM Tris buffer pH 7.4, using a Politron homogenizer (Kinematica). Homogenates were centrifuged at 48000×g for 15 min, resuspended in 50 vols of the same buffer, incubated at 37° C. for 15 min and centrifuged and resuspended two more times. The final pellets were frozen and stored at −80° C. until use.

b) Binding assay: pellets from rat cerebellum were resuspended in 50 mM Tris, 1.2 mM MgCl$_2$, 2 mM CaCl$_2$, pH 7.4; membranes were incubated in a final volume of 1 ml for 30 min at 0° C. with 1.5 nM [$^3$H] R214127 in absence or presence of competing drugs. Non-specific binding was determined in the presence of 1 μM R214127 (Lavreysen H et al Mol. Pharmacol. 63:1082-1093, 2003). The incubation was stopped by the addition of cold Tris buffer pH 7.4 and rapid filtration through 0.5% polyethyleneimine pretreated Filtermat 1204-401 (Wallac) filters. The filters were then washed with cold buffer and the radioactivity retained on the filters was counted by liquid scintillation spectrometry.

c) Data Analysis: the inhibition of specific binding of the radioligands by the tested compounds was analyzed to estimate the inhibitory concentration 50% (IC$_{50}$) value by using the non-linear curve-fitting software Prism 4.0 (Graphpad, San Diego, Calif.). The IC$_{50}$ value was converted to an affinity constant (Ki) by the equation of Cheng & Prusoff (Cheng, Y. C. & Prusoff, W. H. Biochem. Pharmacol. 22, 3099-3108, 1973).

Results

The affinity of the compounds of the instant invention for mGlu1 receptor is at least 10 times lower than their affinity for mGlu5 receptor.

Example 129

Affinity of Selected Antagonists for Group II (mGlu2+mGlu3) Receptor Subtypes

Radioligand Binding Assay at Group II Metabotropic Glutamate Receptors in Rat brain.
Methods
a) Membrane preparation: male Sprague Dawley rats (200-300 g, Charles River, Italy) were killed by cervical dislocation and the forebrain (cortex, striatum and hippocampus) was homogenized (2×20 sec) in 50 vols of cold 50 mM Tris buffer pH 7.4, using a Politron homogenizer (Kinematica). Homogenates were centrifuged at 48000×g for 15 min, resuspended in 50 vols of the same buffer, incubated at 37° C. for 15 min and centrifuged and resuspended two more times. The final pellets were frozen and stored at −80° C. until use.

b) Binding assay: pellets of rat forebrain were washed three times with ice-cold assay buffer (10 mM potassium phosphate+100 nM potassium bromide, ph 7.6). Final pellets were resuspended in 200 vols of the assay buffer and membranes incubated in a final volume of 1 ml for 30 min at 0° C. with 1 nM [$^3$H]LY341495 in the absence or presence of competing drugs. Non-specific binding was determined in the presence of 1 mM 1-glutamate (Wright R. A. et al. J. Pharmacol. Exp. Ther. 298:453-460, 2001; Mutel V et al. J. Neurochem. 75, 2590-2601, 2000). The incubation was stopped by the addition of cold Tris buffer pH 7.4 and rapid filtration through 0.5% polyethyleneimine pretreated Filtermat 1204-401 (Wallac) filters. The filters were then washed with cold buffer and the radioactivity retained on the filters was counted by liquid scintillation spectrometry.

c) Data Analysis: the inhibition of specific binding of the radioligands by the tested compounds was analyzed to estimate the inhibitory concentration 50% ($IC_{50}$) value by using the non-linear curve-fitting software Prism 4.0 (Graphpad, San Diego, Calif.). The $IC_{50}$ value was converted to an affinity constant (Ki) by the equation of Cheng & Prusoff (Cheng, Y. C. & Prusoff, W. H. Biochem. Pharmacol. 22, 3099-3108, 1973).
Results The compounds of the instant invention did not affect [$^3$H]LY341495 binding to Group II (mGlu2+mGlu3) metabotropic glutamate receptors up to 1000 nM.

Example 130

Determination of Functional Activity at mGlu5 Receptor as Accumulation of Inositol Phosphate To determine the mode of action (agonist, antagonist or inverse agonist) of the test compounds at mGlu5 receptor, the concentration dependence of the stimulation of inositol phosphate production in response to the agonist (glutamate or quisqualic acid) is compared in the absence and presence of different concentrations of the test compounds themselves, measured in cells expressing mGlu5 receptor.

The cells are preincubated with the glutamate-degrading enzyme (1 U/ml glutamate pyruvate transaminase) and 2 mM pyruvate to avoid the possible action of glutamate released from the cells. The stimulation is then conducted in a medium containing 10 mM LiCl, and different concentrations of the agonist (glutamate or quisqualic acid) or compounds to be tested for agonistic activity.

When antagonist activity is studied, test compounds are added to cell cultures 20 min prior to the addition of the agonist and further incubated in the presence of the agonist. The incubation is stopped by adding ice cold perchloric acid then samples are neutralized, centrifuged and the supernatant utilized for the determination of inositol phosphate (IP) accumulation using the The Biotrak D-myo-Inositol 1,4,5-trisphosphate assay system from Amersham Biosciences. D-myo-Inositol 1,4,5-trisphosphate ($IP_3$) may be measured in the range 0.19-25 pmol (0.08-10.5 ng) per tube. In the assay, unlabelled $IP_3$ competes with a fixed amount of [$^3$H]-labelled $IP_3$ for a limited number of bovine adrenal $IP_3$ binding proteins. The bound $IP_3$ is then separated from the free $IP_3$ by centrifugation, which brings the binding protein to the bottom of the tube. The free $IP_3$ in the supernatant can then be discarded by simple decantation, leaving the bound fraction adhering to the tube. Measurement of the radioactivity in the tube enables the amount of unlabelled $IP_3$ in the sample to be determined by interpolation from a standard curve.

$EC_{50}/IC_{50}$ are determined by nonlinear regression analysis using the software Prism 4.0 (Graphpad, San Diego, Calif.).
Results The exemplary compounds of the instant invention will show antagonistic activity.

Example 131

Effect on Cystometry in Conscious Rats

Methods.

Male Sprague-Dawley rats [Crl: CD® (SD) IGS BR] of 300-400 g b.w. supplied by Charles River Italia were used. The animals were housed with free access to food and water and maintained on a forced 12-hour-light/12-hour-dark cycle at 22-24° C. of temperature, except during the experiment. To quantify urodynamic parameters in conscious rats, cystometrographic studies were performed according to the procedure previously reported (Guarneri et al., Pharmacol. Res. 24: 175, 1991).

Briefly, the rats were anaesthetised by intraperitoneal administration of 3 ml/kg of Equithensin solution (pentobarbital 30 mg/kg and chloral hydrate 125 mg/kg) and placed in a supine position. An approximately 10 mm long midline incision was made in the shaved and cleaned abdominal wall. The urinary bladder was gently freed from adhering tissues, emptied and then cannulated via an incision in the bladder body, using a polyethylene cannula (0.58 mm internal diameter, 0.96 mm external diameter) which was permanently sutured with silk thread. The cannula was exteriorised through a subcutaneous tunnel in the retroscapular area, where it was connected to a plastic adapter in order to avoid the risk of removal by the animal. For drug testing, the rats were utilised one day after implantation.

On the day of the experiment, the rats were placed in modified Bollman cages, i.e., restraining cages that were large enough to permit the rats to adopt a normal crouched posture, but narrow enough to prevent turning around. After a stabilisation period of about 20 minutes, the free tip of the bladder cannula was connected through a T-shaped tube to a pressure transducer (Statham P23XL) and to a peristaltic pump (Gilson Minipuls 2) for continuous infusion of a warm (37° C.) saline solution into the urinary bladder, at a constant rate of 0.1 ml/minute. The intraluminal-pressure signal during infusion of saline into the bladder (cystometrogram) was continuously recorded on a polygraph (Rectigraph-8K San-ei with BM614/2 amplifier from Biomedica Mangoni) or stored on PC by data acquisition system (PowerLab, Chart 4 software, AD Instruments). From the cystometrogram, bladder volume capacity (BVC) was evaluated. BVC (in ml) is defined as the volume of saline infused into the bladder necessary to induce detrusor contraction followed by micturition.

Basal BVC value was evaluated as the mean of the values observed in the cystometrograms recorded in an initial period of 30-60 minutes. At this point in the assay, the infusion was interrupted and the test compounds were administered orally by a stomach tube. The bladder infusion restarted and changes in BVC were evaluated from the mean values obtained in the cystometrograms observed during 1, 2, and 3 hours after treatment. The compounds were administered in a volume of 2 ml/kg. Groups of control animals received the same amount of vehicle corresponding to a solution 0.5% methocel in water.

Under the given test conditions, measurement of BVC is equivalent to measurement of interval time between micturitions.

Statistical Analysis

Each experimental group was composed of 4-11 animals. All data were expressed as mean±standard error. The percent change of BVC versus the basal value, as well as Δ value (difference in ml) of BVC (BVC at time "x" minus basal value), were also evaluated for each rat/time. In the figures, data are reported as % change versus the basal value.

Statistical analysis on BVC values, as well as on Δ values, was performed by S.A.S./STAT software, version 6.12. The difference between vehicle and active treatment effect was evaluated on Δ values of BVC, whereas the difference between the values at different times versus the basal values was evaluated on original BVC data.

Results

The compound of the invention, administered at 0.1 to 10 mg/kg p.o. proved effective in increasing the bladder volume capacity.

The reference compound MTEP, orally administered at the dose of 1 mg/kg showed only a slight increase of bladder volume capacity, whereas the dose of 3 mg/kg induced a sustained increase of this parameter, which resulted statistically significant from the vehicle group after 3 hours from treatment.

The activity of compounds of the invention and reference standard was expressed as MED (i.e. Minimal Effective Dose that induces statistically significant increase of bladder volume capacity). MTEP showed a MED of 3. For some compounds of the invention MED was equal or better. For instance the Compound of Example 78 showed a MED of 3.

Example 132

Plasma Extravasation in the Dura Mater of Rats Induced by Electrical Stimulation of the Trigeminal Ganglion Electrical stimulation of the trigeminal ganglion induces inflammation in the dura mater which causes plasma extravasation. This animal model is widely accepted for testing drugs useful in migraine.

Male Wistar rats weighing 175-190 g are anaesthetised with 50 mg/kg i.p. of pentobarbital and the jugular vein is cannulated for injection of drugs. The animals are placed in a stereotaxic frame. Symmetrical boreholes are drilled 3.0 mm laterally and 3.2 mm posteriorly from bregma and the electrodes are lowered 9.5 mm from dura mater. The test compound or control-vehicle solution are administered intravenously 10 min prior to electrical stimulation of the right trigeminal ganglion (5 min; 2.0 mA, 5 Hz, 5 ms duration and Evans blue (30 mg/kg i.v.), is given 5 min prior to electrical stimulation as a marker of plasma protein extravasation. 15 minutes after the end of the stimulation period the animals are perfused with 50 ml saline via the left cardiac ventricle to remove intravascular Evans blue. The dura mater is removed, blotted dry and weighed. Tissue Evans blue is extracted in 0.3 ml formamide at 50° C. for 24 h. Dye concentrations are measured with a spectrophotometer at 620 nm wavelength, interpolated on a standard curve and expressed as ng Evans blue content per mg tissue weight.

Extravasation is Expressed as the Quotient Calculated by Dividing the Evan's Blue Content Of the Stimulated Side by the Evan's Blue Content of the Unstimulated Side.

Example 133

GERD Model in Dogs

Beagle dogs are equipped with a chronic esophagostomy to allow passage of a manometric catheter and a pH probe along the esophagus and the stomach.

Following recording of the basal pressure of the Lower Esophageal Sphincter and the stomach, compounds under evaluation and vehicle for control are administered by intravenous route.

Transient Lower Esophageal Sphincter Relaxations (TLESRs) and acid reflux are induced by infusion of an acidified meal followed by stomach distension using a peristaltic pump infusing air at 40 ml/min, in accordance to Stakeberg J. and Lehmann A., (Neurogastroenterol. Mot. (1999) 11: 125-132). Active compounds reduce dose-dependently the frequency of TLESRs and TLESRs associated with acid reflux. The activity is determined as % inhibition of both parameters as compared to vehicle control.

Example 134

Vogel Conflict Test in Rat

The method, which detects anxiolytic activity, follows that described by Vogel et al. as "Anxiolytics increase punished drinking" (Vogel J. R., Beer B., Clody D. E. A simple and reliable conflict procedure for testing anti-anxiety agents Psychopharmacologia, 21, 1-7, 1971).

Rats are deprived of water for approximately 48 hours and are then placed individually into a transparent Plexiglas enclosure (15×32×34 cm) with a floor consisting of stainless steel bars (0.4 cm) spaced 1 cm apart. The back wall of the enclosure is made of opaque Plexiglas thereby concealing the observer from the experimental animal. In the centre of the opposite wall, 5 cm above the floor, a metal water spout protrudes into the cage and is connected to one pole of a shock generator. The other pole of the shock generator is connected to the metal grid floor.

The rat is left to explore until it founded the water spout. Then, every time it drinks, it receives a slight electric shock (1.7 mA, 1 s) 2 seconds after it starts lapping. The number of punished drinks is counted during a 3 minute test.

The test is performed blind.

The test compounds are administered p.o. 60 minutes before the test, and compared with a vehicle control group.

Example 135

Operant Alcohol Self-Administration Training

The method is used to assess a substance abuse model and to detect the activity of the compounds of the invention in preventing this behavior.

Rats are trained to orally self-administer ethanol by using a modification of a training protocol described previously by Samson (1986). Briefly, rats are deprived of water for 12 h prior to training sessions for three consecutive days and are trained to respond for a 0.1-ml drop of 0.2% (w/v) saccharin solution on both levers under a fixed ratio 1 (FR1) schedule of reinforcement. After this initial training, water deprivation is terminated, and animals have free access to food and water in their home cages throughout the subsequent training and testing. Non-deprived rats are given two additional saccharin sessions to confirm that they have acquired responding for saccharin before ethanol self administration training starts. Then, during the next three sessions, responses at the right lever result in the delivery of 0.1 ml of 5% (w/v) ethanol+ 0.2% saccharin solution. Responses at the left lever are recorded but had no programmed consequences. Thereafter, the concentration of ethanol is increased first to 8% and then to 10% w/v and the concentration of saccharin is decreased until saccharin is eliminated completely from the drinking solution.

The final schedule of reinforcement for the 10% w/v ethanol concentration is similar to the training schedule except that a stimulus light is added. Thus, during the 30-min sessions responses on the active lever results in the delivery of 0.1 ml of ethanol and, in addition, in the illumination of the stimulus light for 3 s. The left lever remains inactive. When rats have reached stable ethanol self-administration under these conditions, the effects of the tested compounds after i.p. administration on ethanol self administration are examined. The agonists are administered 30 min before start of the self-administration session.

Example 136

Neuropathic Pain Test (Bennett) in the Rat

The method, which detects analgesic activity in rats with neuropathic pain, follows that described by Bennett and Xie (Bennett G. J., Xie Y. K., A peripheral mononeuropathy in rat that produces disorders of pain sensation like those seen in man, Pain, 33, 87-107, 1988).

Chronic constriction injury of the common sciatic nerve in rats is associated with hyperalgesia, allodynia and spontaneous pain, and constitutes therefore a model for peripheral neuropathic pain in humans. Antihyperalgesics reduce these chronic signs of pain hypersensitivity.

Rats (150-200 g) are anesthetized (sodium pentobarbital 40 mg/kg i.p.) and an incision at mid-thigh level is performed to expose the common left sciatic nerve. Four ligatures spaced 1 mm apart are loosely tied around the sciatic nerve. The wound is then sutured. The rats are allowed to recover. One week after the surgery, when the chronic pain state is fully installed, rats are submitted consecutively to tactile and thermal stimulation of both hindpaws.

For tactile stimulation, the animal is placed under an inverted acrylic plastic box (17×11×14 cm) on a grid floor. The tip of an electronic Von Frey probe is then applied with increasing force to the non-inflamed and inflamed hindpaws and the force inducing paw-withdrawal is automatically recorded. This procedure is carried out 3 times and the mean force per paw is calculated.

For thermal stimulation, the apparatus consists of individual acrylic plastic boxes (17×11×14 cm) placed upon an elevated glass floor. A rat is placed in the box and left free to habituate for 10 minutes. A mobile infrared radiant source ($96\pm10$ mW/cm$^2$) is then focused first under the non-lesioned and then the lesioned hindpaw and the paw-withdrawal latency is automatically recorded. In order to prevent tissue damage the heat source is automatically turned off after 45 seconds.

Prior to receiving drug treatment all animals are submitted to tactile stimulation of the hindpaws and assigned to treatment groups matched on the basis of the pain response of the lesioned hindpaw.

8 rats are studied per group. The test is performed blind.

Test compounds are administered p.o. 60 minutes before the test, and compared with a vehicle control group (0.5% carboxymethylcellulose (CMC) in distilled water).

Example 137

Limbic Epileptogenesis in a Mouse Model

FMRP (fragile X mental retardation protein) plays a critical role in suppressing limbic epileptogenesis and predict that the enhanced susceptibility of patients with FXS to epilepsy is a direct consequence of the loss of an important homeostatic factor that mitigates vulnerability to excessive neuronal excitation.

Kindling experiments are conducted in FMRI mutant mice (knockout mice with reduced expression of mGluR5) during the light phase of the cycle on 12-week-old adult mice.

A twisted bipolar electrode is implanted into the right amygdale (coordinates: 2.9 mm lateral and 1.2 mm posterior to bregma, 4.6 mm below dura) of animals under pentobarbital (60 mg/kg) anesthesia. Animals are then given 10 days to recover. The electrographic seizure threshold (EST) for each individual mouse is determined by applying 1-s train of 1-ms biphasic rectangular pulses at 60 Hz beginning at 50 IA. Additional stimulations increasing by 10 IA are administered at 2-min intervals until an electrographic seizure lasting at least 5 s was evoked. Stimulations at the EST intensity are subsequently applied once daily. EEGs and behavioral seizures are observed and recorded. The severity of the behavioral manifestations of seizures is classified according to the criteria of Racine (1972). Fully kindled is defined by the occurrence of 3 consecutive seizures of class 4 or greater. All surgery and kindling procedures are performed blind to genotype.

Unstimulated control animals of each genotype undergo surgical implantation of an electrode in the amygdala and are handled identically but are not stimulated. Electrode placement is confirmed by methyl green pyronine-Y staining. Data derived from animals with correct electrode placement are analyzed.

Tested drugs are administered by intraperitoneal injection 30 min before a class 5 seizure-inducing stimulation.

Example 138

6-hydroxydopamine-lesioned rats

This model is a reliable and robust model for reproducing Parkinson's lesions in the brain and for studying the protecting effects of drugs.

Female Sprague-Dawley rats (180-220 g) undergo stereotaxic surgery to produce lesions of the nigrostriatal system. Within each experimental group, half of the animals receive an intrastriatal injection of 6-hydroxydopamine (6-OHDA) with 0.01% ascorbic acid in saline (lesioned animals) while the remaining animals receive an intrastriatal injection of 0.01% ascorbic acid in saline (control animals). Surgical procedure for unilateral intrastriatal injection of 6-OHDA: rats are anaesthetized with sodium pentobarbitone (60 mg/kg, i.p.) and placed in a Kopf stereotaxic apparatus, where the head is constrained to a tilted skull position (−3.0 mm). An incision is made on the midline of the scalp and a burr hole drilled through the skull at the appropriate coordinates. Through this, an intracerebral injection is delivered into the left striatum using a 30 gauge blunt-tipped cannula. Stereotaxic coordinates for injection are: 0.3 mm anterior and 3.0 mm lateral from Bregma, and 5.2 mm ventral from the cortical surface, according to the atlas of Paxinos & Watson Lesioned rats receive 4 μl of 2.5 μg/μl 6-OHDA/0.01% (w/v) ascorbic acid, while control rats receive 4 μl of saline/0.01% (w/v) ascorbic acid. Injections are delivered at a rate of 0.6 μl/min and the needle left in position for 10 min following injection before being withdrawn slowly. After sealing the skull, the incision is closed and the animals are allowed to recover.

Tested compounds are administered for 14 days before the induced lesions. Protection of tested compound from loss of striatal dopaminergic nerve terminals is assessed by [$^3$H]-mazindol autoradiography.

Seven days after stereotaxic surgery, rats are lightly anaesthetized ($CO_2/O_2$: 80/20) and are decapitated. Brains are rapidly removed and frozen over liquid nitrogen, then stored at −40° C. prior to sectioning.

A Reichert Jung cryostat is used to cut consecutive coronal 14 μm sections of striatum at level+0.30 mm from Bregma according to the atlas of Paxinos & Watson. Sections are thaw mounted onto poly-L-lysine coated slides, then stored at −20° C. until use. [$^3$H]-mazindol autoradiography is used to visualize dopaminergic nerve terminals within sections of striatum taken from rat brains. All autoradiographic steps are carried out at 4° C. to reduce non-specific binding.

Slide mounted sections of striatum are preincubated for 15 min in 50 mm Tris-HCl solution (pH 7.9) containing 120 mm NaCl and 5 mm KCl. Sections are then incubated for 60 min with 4 nM [$^3$H]-mazindol in 50 mm Tris-HCl solution (pH 7.9) containing 300 mM NaCl and 5 mM KCl. Desipramine (DM1; 300 nM) is included in all incubation solutions to prevent non-selective [$^3$H]-mazindol binding at noradrenergic uptake sites. Nomifensine (100 μm), a selective inhibitor of dopamine uptake sites, is used to determine non-specific binding. Sections are washed twice (2×3 min) in ice-cold incubation buffer to remove excess [$^3$H]-mazindol and are dried under a stream of cold, dry air.

Once dry, radiolabelled sections are apposed to Hyperfilm-$^3$H and are exposed for 21 days to allow an image of striatal dopaminergic nerve terminal density to develop on the film. Following the exposure period, films are developed for 5 min in Phenisol X-ray developer, rinsed briefly in a weak solution of stopbath and fixed in Hypam X-ray fixer for 10 min. Computer-assisted densitometry is used to quantify the optical density of film images. The system is calibrated using [$^3$H]-standards, so that optical density measurements are made in nCi mm$^{-2}$. Specific binding is determined by subtracting the non-specific binding image from that of total binding, and is measured in the entire striatum.

Data Analysis

The mean optical density and standard error of the mean are determined from independent measurements taken in at least three consecutive coronal sections of striatum for each animal.

The invention claimed is:

1. A compound of Formula I

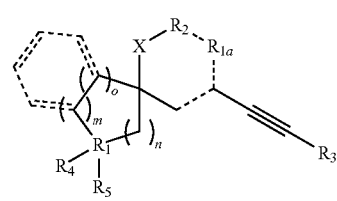

wherein:

X is oxygen or sulfur;

$R_1$ is carbon, nitrogen, oxygen or sulfur;

$R_{1a}$ is CH, $CH_2$, N, or NH;

$R_2$ is a bond, a CH group or a $CH_2$ group;

$R_3$ is an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group;

$R_4$ is absent is hydrogen, or is an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, an optionally substituted alkyl group, hydroxy, alkoxy, thiol, thioalkyl, amino, N-alkylamino, or N,N-dialkylamino or a halogen atom;

$R_5$ is absent is hydrogen, hydroxyl, thiol, amino, or is optionally substituted alkyl, alkoxy, thioalkyl, alkylamino, dialkylamino, cyano, aminocarbonyl, alkylaminocarbonyl, arylcarbonyl, dialkylaminocarbonyl, N-alkoxy-N-alkylaminocarbonyl, alkoxycarbonyl, aryloxycarbonyl, heteroaryloxycarbonyl, heterocyclylcarbonyl, heteroarylcarbonyl, or heterocyclylaminocarbonyl, or a halogen atom; or when $R_1$ is a carbon atom, R4 and R5 are joined together to form an optionally substituted methylene group, a keto group, an oxime each one optionally substituted with alkyl, cycloalkyl, halogen or a heterocyclic group; or when $R_1$ is a carbon atom, $R_4$ and $R_5$ are each carbon, oxygen, nitrogen, or sulfur linked to each other through an optionally substituted $C_1$-$C_3$ alkylene group;

m is 1-2;

n is 1-2;

o is 0-1; and

---- is a single or double bond;

is an optionally substituted phenyl group which is optionally present when m is 1, n is 1 or 2, and o is 1; or enantiomers, diastereomers, or N-oxides thereof; or pharmaceutically acceptable salts thereof.

2. The compound of claim 1, wherein the compound is of Formula Ia,

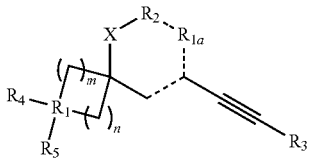

wherein:
X is oxygen or sulfur;
$R_1$ is carbon, nitrogen, oxygen or sulfur;
$R_{1a}$ is CH, $CH_2$, N, or NH;
$R_2$ is a bond, a CH group or a $CH_2$ group;
$R_3$ is an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group;
$R_4$ is absent or is an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, an optionally substituted alkyl group, hydroxy, alkoxy, thiol, thioalkyl, amino, N-alkylamino, or N,N-dialkylamino or a halogen atom;
$R_5$ is absent or is optionally substituted alkyl, hydroxy, alkoxy, thiol, thioalkyl, amino, alkylamino, dialkylamino, cyano, aminocarbonyl, alkylaminocarbonyl, dialkylaminocarbonyl, N-alkoxy-N-alkylaminocarbonyl, alkoxycarbonyl, aryloxycarbonyl, heteroaryloxycarbonyl, heterocyclylcarbonyl, heteroarylcarbonyl, heterocyclyaminocarbonyl heterocyclyaminocarbonyl, each one optionally substituted or a halogen atom; or
when $R_1$ is a carbon atom, $R_4$ and $R_5$ are joined together to form an optionally substituted methylene group, a keto group, an oxime each one optionally substituted with alkyl, cycloalkyl, halogen or a heterocyclic group; or
when $R_1$ is a carbon atom, $R_4$ and $R_5$ are each oxygen, nitrogen, or sulfur linked to each other through an optionally substituted $C_2$-$C_3$ alkylene group;
m is 1-3;
n is 1-2; and
---- is a single or double bond; and
enantiomers, diastereomers, and N-oxides thereof; and pharmaceutically acceptable salts thereof.

3. The compound of claim 2, wherein the optional substituents are independently selected from one or more of hydroxy, nitro, cyano, amino, thiol, alkoxy, N-alkylamino, or N,N-dialkylamino, halogen, oxo, aryloxy or heteroaryloxy, carbamoyl, sulfamoyl, (di)alkylaminocarbonyl, (di)alkylaminosulphonyl, alkoxycarbonyl, (poly)haloalkyl, $C_1$-$C_6$ alkylsulphonyl, $C_1$-$C_6$ alkylthio, (di)$C_1$-$C_6$ alkylthio, (di)$C_1$-$C_6$ alkylcarbonylamino, $C_1$-$C_6$ alkylcarbonyl or $C_1$-$C_6$ alkylcarbonyl-($C_1$-$C_6$)alkyl group, or or a group of the formula —NR*R* wherein each R* independently represents a hydrogen atom or a $C_1$-$C_6$ alkyl, $C_1$-$C_6$ alkylcarbonyl, phenyl or benzyl group, or $C_1$-$C_6$ alkyl, $C_2$-$C_6$ alkenyl, $C_2$-$C_6$ alkynyl or $C_1$-$C_6$ alkoxy group, each of which may optionally bear from 1 to 8 substitutents independently selected from oxo, halo, cyano, nitro, amino, hydroxy and phenyl; or $C_3$-$C_9$ mono- or bicycloalkyl group each of which may be optionally bear from 1 to 3 substituents independently selected from $C_1$-$C_6$ alkyl, oxo, halo, cyano, nitro, amino, hydroxy and phenyl substituents; or an optionally substituted mono- or bicyclic $C_1$-$C_9$ heterocyclic group containing from 1 to 3 heteroatoms selected from nitrogen, oxygen and sulfur; or an optionally substituted mono-, bi- or tricyclic $C_6$-$C_{14}$ aryl group, or an optionally substituted $C_3$-$C_7$ cycloalkyl group; or a group of the formula -A, —O-A, —C(O)-A, —($CH_2$)q-A, —NR-A, —C(O)NR-A, —NR**C(O)-A or —OC(O)-A, wherein A is a phenyl group or a $C_1$-$C_8$ heterocyclic group containing from 1 to 3 heteroatoms selected from N, O, and S; each group A of being optionally substituted with from 1 to 3 groups independently selected from halo, hydroxy, cyano, nitro and $C_1$-$C_6$ alkyl;

R** is independently selected from hydrogen and $C_1$-$C_6$ alkyl, and q is 0 or an integer from 1 to 6.

4. The compound of claim 2, wherein $R_1$ is nitrogen, $R_5$ is absent, and $R_4$ is an optionally substituted mono- or bicyclic or tricyclic $C_1$-$C_{13}$ heterocyclic group containing from 1 to 5 heteroatoms selected from N, O, and S.

5. The compound of claim 4, wherein $R_4$ represents an optionally substituted mono-, bi- or tricyclic $C_1$-$C_9$ heterocyclic group containing 1 to 5 heteroatoms selected from N, O, and S, Even more preferably, $R_4$ is an optionally substituted group selected from phenyl, furanyl, thienyl, isoxazolyl, pyridinyl, and pyrazinyl.

6. The compound of claim 5, wherein the optional substituent on the $R_4$ group is selected from one or more of halogen, alkyl, alkoxy, nitro, amino, hydroxyl, carboxyl, cyano, and trifluoromethyl.

7. The compound of claim 2, wherein $R_1$ is carbon, and $R_4$ and $R_5$ are linked together to form an optionally substituted methylene, an optionally substituted oxime, or a keto group.

8. The compound of claim 7, wherein $R_4$ and $R_5$ are linked together to form an methylene optionally substituted with pyridyl, an oxime optionally substituted with alkyl, or a lactone, or a keto group.

9. The compound of claim 2, wherein $R_1$ is carbon and $R_4$ and $R_5$ are independently oxygen, NH, or S joined together through a $C_2$-$C_3$ alkenyl group to form a spirocycle, or $R_4$ is cyano and $R_5$ is a monocyclic heteroaromatic containing 1-3 nitrogens.

10. The compound of claim 9, wherein $R_4$ and $R_5$ are oxygen and the spirocyclic ring is an optionally substituted 1,3-dioxolanyl or 1,3-dioxanyl ring.

11. The compound of claim 2, wherein $R_3$ is $C_1$-$C_6$ alkyl, optionally substituted phenyl or optionally substituted monocyclic $C_1$-$C_5$ heteroaromatic group containing from 1 to 4 heteroatoms selected from the group consisting of N, S, and O.

12. The compound of claim 11, wherein $R_3$ is optionally substituted phenyl, thienyl, furanyl, thiozolyl, pyrazinyl, oxadiazolyl or pyridinyl.

13. A compound of Formula II

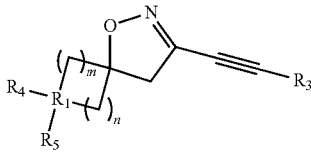

$R_1$ is carbon, nitrogen, oxygen or sulfur;
$R_3$ is an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group;
$R_4$ is absent or is an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, an optionally substituted alkyl group, hydroxy, alkoxy, thiol, thioalkyl, amino, N-alkylamino, or N,N-dialkylamino or a halogen atom;
$R_5$ is absent or is optionally substituted alkyl, hydroxy, alkoxy, thiol, thioalkyl, amino, alkylamino, dialkylamino, cyano, aminocarbonyl, alkylaminocarbonyl, dialkylaminocarbonyl, N-alkoxy-N-alkylaminocarbonyl, alkoxycarbonyl, aryloxycarbonyl, heteroaryloxycarbonyl, heterocyclylcarbonyl, heteroarylcarbonyl, heterocyclyaminocarbonyl heterocyclyaminocarbonyl, each one optionally substituted or a halogen atom; or
when $R_1$ is a carbon atom, $R_4$ and $R_5$ are joined together to form an optionally substituted methylene group, a keto group, an oxime each one optionally substituted with alkyl, cycloalkyl, halogen or a heterocyclic group; or
when $R_1$ is a carbon atom, $R_4$ and $R_5$ are each oxygen, nitrogen, or sulfur linked to each other through an optionally substituted $C_2$-$C_3$ alkylene group;
m is 1-3;
n is 1-2; and
---- is a single or double bond; and
enantiomers, diastereomers, and N-oxides thereof; and pharmaceutically acceptable salts thereof.

14. A compound of Formula III

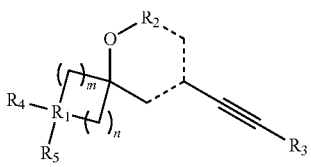

wherein:
$R_1$ is carbon, nitrogen, oxygen or sulfur;
$R_2$ is a bond, a CH group or a $CH_2$ group;
$R_3$ is an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group;
$R_4$ is absent or is an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, an optionally substituted alkyl group, hydroxy, alkoxy, thiol, thioalkyl, amino, N-alkylamino, or N,N-dialkylamino or a halogen atom;
$R_5$ is absent or is optionally substituted alkyl, hydroxy, alkoxy, thiol, thioalkyl, amino, alkylamino, dialkylamino, cyano, aminocarbonyl, alkylaminocarbonyl, dialkylaminocarbonyl, N-alkoxy-N-alkylaminocarbonyl, alkoxycarbonyl, aryloxycarbonyl, heteroaryloxycarbonyl, heterocyclylcarbonyl, heteroarylcarbonyl, heterocyclyaminocarbonyl heterocyclyaminocarbonyl, each one optionally substituted or a halogen atom; or
when $R_1$ is a carbon atom, R4 and R5 are joined together to form an optionally substituted methylene group, a keto group, an oxime each one optionally substituted with alkyl, cycloalkyl, halogen or a heterocyclic group; or
when $R_1$ is a carbon atom, $R_4$ and $R_5$ are each oxygen, nitrogen, or sulfur linked to each other through an optionally substituted $C_2$-$C_3$ alkylene group;
m is 1-3;
n is 1-2; and
---- is a single or double bond; and
enantiomers, diastereomers, and N-oxides thereof; and pharmaceutically acceptable salts thereof.

15. A pharmaceutical composition comprising a pharmaceutically acceptable excipient or diluent and a compound of claim 1.

16. A compound selected from the group consisting of:
8-(6-Methyl-3-nitropyridin-2-yl)-3-(phenylethynyl)-1-oxa-2,8-diazaspiro[4.5]dec-2-ene
8-(3-Nitropyridin-2-yl)-3-(phenylethynyl)-1-oxa-2,8-diazaspiro[4.5]dec-2-ene
8-(6-Methyl-3-nitropyridin-2-yl)-3-[(6-methylpyridin-2-yl)ethynyl]-1-oxa-2,8-diazaspiro[4.5]dec-2-ene
8-(6-Methyl-3-nitropyridin-2-yl)-3-(thien-2-ylethynyl)-1-oxa-2,8-diazaspiro[4.5]dec-2-ene
8-(6-Methyl-3-nitropyridin-2-yl)-3-(pyridin-2-ylethynyl)-1-oxa-2,8-diazaspiro[4.5]dec-2-ene
3-[(2-Fluorophenyl)ethynyl]-8-(6-methyl-3-nitropyridin-2-yl)-1-oxa-2,8-diazaspiro[4.5]dec-2-ene
3-[(3-Fluorophenyl)ethynyl]-8-(6-methyl-3-nitropyridin-2-yl)-1-oxa-2,8-diazaspiro[4.5]dec-2-ene
3-[(4-Fluorophenyl)ethynyl]-8-(6-methyl-3-nitropyridin-2-yl)-1-oxa-2,8-diazaspiro[4.5]dec-2-ene
3-(2-Furylethynyl)-8-(6-methyl-3-nitropyridin-2-yl)-1-oxa-2,8-diazaspiro[4.5]dec-2-ene
8-(6-Methyl-3-nitropyridin-2-yl)-3-[(2-methyl-1,3-thiazol-4-yl)ethynyl]-1-oxa-2,8-diazaspiro[4.5]dec-2-ene
8-(6-Methyl-3-nitropyridin-2-yl)-3-prop-1-ynyl-1-oxa-2,8-diazaspiro[4.5]dec-2-ene
3-[(3-Chlorophenyl)ethynyl]-8-(6-methyl-3-nitropyridin-2-yl)-1-oxa-2,8-diazaspiro[4.5]dec-2-ene
8-(6-Methyl-3-nitropyridin-2-yl)-3-[(3-methylphenyl)ethynyl]-1-oxa-2,8-diazaspiro[4.5]dec-2-ene
3-[(3-Methoxyphenyl)ethynyl]-8-(6-methyl-3-nitropyridin-2-yl)-1-oxa-2,8-diazaspiro[4.5]dec-2-ene
3-{[8-(6-Methyl-3-nitropyridin-2-yl)-1-oxa-2,8-diazaspiro[4.5]dec-2-en-3-yl]ethynyl}benzonitrile
8-(6-Methyl-3-nitropyridin-2-yl)-3-(thien-3-ylethynyl)-1-oxa-2,8-diazaspiro[4.5]dec-2-ene
8-(6-Methyl-3-nitropyridin-2-yl)-3-(pyridin-3-ylethynyl)-1-oxa-2,8-diazaspiro[4.5]dec-2-ene
8-(6-Methyl-3-nitropyridin-2-yl)-3-[3-(3-methyl-[1,2,4]oxadiazol-5-yl)phenylethynyl]-1-oxa-2,8-diaza-spiro[4.5]dec-2-ene 3-(3-Methylbut-1-ynyl)-8-(6-methyl-3-nitropyridin-2-yl)-1-oxa-2,8-diaza-spiro[4.5]dec-2-ene
3-Hex-1-ynyl-8-(6-methyl-3-nitropyridin-2-yl)-1-oxa-2,8-diazaspiro[4.5]dec-2-ene
2-{[8-(6-Methyl-3-nitropyridin-2-yl)-1-oxa-2,8-diaza-spiro[4.5]dec-2-en-3-yl]ethynyl}benzonitrile
3-[3-(3-Chlorophenylethynyl)-1-oxa-2,8-diazaspiro[4.5]dec-2-en-8-yl]pyrazine-2-carbonitrile
8-(6-Methyl-3-nitropyridin-2-yl)-3-[(2-methylphenyl)ethynyl]-1-oxa-2,8-diazaspiro[4.5]dec-2-ene
3-[(2-Chlorophenyl)ethynyl]-8-(6-methyl-3-nitropyridin-2-yl)-1-oxa-2,8-diazaspiro[4.5]dec-2-ene
8-(6-Methyl-3-nitropyridin-2-yl)-3-(pyrazin-2-ylethynyl)-1-oxa-2,8-diazaspiro[4.5]dec-2-ene
8-(6-Methyl-3-nitropyridin-2-yl)-3-(phenylethynyl)-1-oxa-8-azaspiro[4.5]dec-3-ene
3-[(3-Chlorophenyl)ethynyl]-7-(6-methyl-3-nitropyridin-2-yl)-1-oxa-2,7-diazaspiro[4.4]non-2-ene
7-[(3-Chlorophenyl)ethynyl]-2-(6-methyl-3-nitropyridin-2-yl)-5-oxa-2,6-diazaspiro[3.4]oct-6-ene
9-(6-Methyl-3-nitropyridin-2-yl)-4-(2-phenylethynyl)-1-oxa-9-azaspiro[5.5]undec-4-ene
9-(6-Methyl-3-nitropyridin-2-yl)-4-(2-phenylethynyl)-1-oxa-9-azaspiro[5.5]undec-3-ene
3-[(3-Chlorophenyl)ethynyl]-1,9,12-trioxa-2-azadispiro[4.2.4.2]tetradec-2-ene
3-[(3-Chlorophenyl)ethynyl]-1-oxa-2-azaspiro[4.5]dec-2-en-8-one
3-[(3-Chlorophenyl)ethynyl]-8-methylene-1-oxa-2-azaspiro[4.5]dec-2-ene
3-[(3-Chlorophenyl)ethynyl]-1-oxa-2-azaspiro[4.5]dec-2-en-8-one O-methyloxime
7-(6-Methyl-3-nitropyridin-2-yl)-3-[(6-methylpyridin-2-yl)ethynyl]-1-oxa-2,7-diazaspiro[4.4]non-2-ene
7-(6-Methyl-3-nitropyridin-2-yl)-3-(phenylethynyl)-1-oxa-2,7-diazaspiro[4.4]non-2-ene
3-[(3-Fluorophenyl)ethynyl]-7-(6-methyl-3-nitropyridin-2-yl)-1-oxa-2,7-diazaspiro[4.4]non-2-ene
2-(6-Methyl-3-nitropyridin-2-yl)-7-(phenylethynyl)-5-oxa-2,6-diazaspiro[3.4]oct-6-ene
3-{[7-(6-Methyl-3-nitropyridin-2-yl)-1-oxa-2,7-diazaspiro[4.4]non-2-en-3-yl]ethynyl}phenol
7-[(3-Fluorophenyl)ethynyl]-2-(6-methyl-3-nitropyridin-2-yl)-5-oxa-2,6-diazaspiro[3.4]oct-6-ene
3-[(3-Chlorophenyl)ethynyl]-8-(pyridin-2-ylmethylene)-1-oxa-2-azaspiro[4.5]dec-2-ene
3-[(3-Chlorophenyl)ethynyl]-8-(pyridin-2-ylmethyl)-1-oxa-2-azaspiro[4.5]dec-2-en-8-ol
3-[(3-Chlorophenyl)ethynyl]-8-(pyridin-2-ylmethyl)-1-oxa-2-azaspiro[4.5]dec-2-en-8-ol
3-(Phenylethynyl)-1,9,12-trioxa-2-azadispiro[4.2.4.2]tetradec-2-ene
3-(2-Phenylethynyl)-1-oxa-2-azaspiro[4.5]dec-2-en-8-one
3-(2-Phenylethynyl)-1-oxa-2-azaspiro[4.5]dec-2-en-8-one oxime
3-(Phenylethynyl)-1-oxa-2-azaspiro[4.5]dec-2-en-8-one O-(2-oxotetrahydrofuran-3-yl)oxime
3-[(6-Methylpyridin-2-yl)ethynyl]-8-pyridin-2-yl-1-oxa-2-azaspiro[4.5]dec-2-ene-8-carbonitrile
3-[(5-Fluoropyridin-2-yl)ethynyl]-1,9,12-trioxa-2-azadispiro[4.2.4.2]tetradec-2-ene
3-[(6-Methylpyridin-2-yl)ethynyl]-1,9,12-trioxa-2-azadispiro[4.2.4.2]tetradec-2-ene
3-[(6-Fluoropyridin-2-yl)ethynyl]-1,9,12-trioxa-2-azadispiro[4.2.4.2]tetradec-2-ene
3-[(6-Fluoropyridin-3-yl)ethynyl]-1,9,12-trioxa-2-azadispiro[4.2.4.2]tetradec-2-ene
3-[(3-Nitrophenyl)ethynyl]-1,9,12-trioxa-2-azadispiro[4.2.4.2]tetradec-2-ene
3-[(2-Methyl-1,3-thiazol-4-yl)ethynyl]-1,9,12-trioxa-2-azadispiro[4.2.4.2]tetradec-2-ene
3-[(3-Methoxyphenyl)ethynyl]-1,9,12-trioxa-2-azadispiro[4.2.4.2]tetradec-2-ene
3-[(3-Chloro-5-fluorophenyl)ethynyl]-1,9,12-trioxa-2-azadispiro[4.2.4.2]tetradec-2-ene
3-[(3-Methyphenyll)ethynyl]-1,9,12-trioxa-2-azadispiro[4.2.4.2]tetradec-2-ene
3-[(3-Ethoxyphenyll)ethynyl]-1,9,12-trioxa-2-azadispiro[4.2.4.2]tetradec-2-ene
3-[(3-Trifluoromethoxyphenyll)ethynyl]-1,9,12-trioxa-2-azadispiro[4.2.4.2]tetradec-2-ene
3-[(3-tert-Butylphenyl)ethynyl]-1,9,12-trioxa-2-azadispiro[4.2.4.2]tetradec-2-ene
3-(1,9,12-Trioxa-2-azadispiro[4.2.4.2]tetradec-2-en-3-ylethynyl)benzonitrile
3-[(3-Fluorophenyl)ethynyl]-1,9,12-trioxa-2-azadispiro[4.2.4.2]tetradec-2-ene
3-[(3-Ethylphenyl)ethynyl]-1,9,12-trioxa-2-azadispiro[4.2.4.2]tetradec-2-ene
3-[(3-Isopropylphenyl)ethynyl]-1,9,12-trioxa-2-azadispiro[4.2.4.2]tetradec-2-ene
3-[(4-Chloropyridin-2-yl)ethynyl]-1,9,12-trioxa-2-azadispiro[4.2.4.2]tetradec-2-ene
3-[(4-Methylpyridin-2-yl)ethynyl]-1,9,12-trioxa-2-azadispiro[4.2.4.2]tetradec-2-ene
3-[(3-Trifluoromethylphenyl)ethynyl]-1,9,12-trioxa-2-azadispiro[4.2.4.2]tetradec-2-ene
3-{[4-(Trifluoromethyl)pyridin-2-yl]ethynyl}-1,9,12-trioxa-2-azadispiro[4.2.4.2]tetradec-2-ene
3-[(5-Chloropyridin-3-yl)ethynyl]-1,9,12-trioxa-2-azadispiro[4.2.4.2]tetradec-2-ene
1-(2-Furyl)-3-(1,9,12-trioxa-2-azadispiro[4.2.4.2]tetradec-2-en-3-yl)prop-2-yn-1-one
4-Hydroxy-2-({[3-(phenylethynyl)-1-oxa-2-azaspiro[4.5]dec-2-en-8-ylidene]amino}oxy)butanoic acid
3-[(3-Chlorophenyl)ethynyl]-1,8-dioxa-2-azaspiro[4.5]dec-2-ene
3-[(6-Methylpyridin-2-yl)ethynyl]-1,8-dioxa-2-azaspiro[4.5]dec-2-ene
3-[(4-Chloropyridin-2-yl)ethynyl]-1,8-dioxa-2-azaspiro[4.5]dec-2-ene
3-[(3-Chlorophenyl)ethynyl]-1-oxa-8-thia-2-azaspiro[4.5]dec-2-ene 8,8-dioxide
3-[(3-Chlorophenyl)ethynyl]-1,7-dioxa-2-azaspiro[4.5]dec-2-ene
3-[(3-Chlorophenyl)ethynyl]-1,9-dioxa-2-azadispiro[4.2.4.2]tetradec-2-ene
3-[(3-Chlorophenyl)ethynyl]-1,9-dioxa-2-azadispiro[4.2.4.2]tetradec-2-ene
3-[(3-Methylphenyl)ethynyl]-1,9-dioxa-2-azadispiro[4.2.4.2]tetradec-2-ene
3-{[2-(6-Methyl-3-nitropyridin-2-yl)-5-oxa-2,6-diazaspiro[3.4]oct-6-en-7-yl]ethynyl}phenol
3-{[2-(6-Methyl-3-nitropyridin-2-yl)-5-oxa-2,6-diazaspiro[3.4]oct-6-en-7-yl]ethynyl}benzonitrile
3'-[(3-Chlorophenyl)ethynyl]-2,3-dihydro-4'H-spiro[indene-1,5'-isoxazol]-3-ol
3'-[(3-Chlorophenyl)ethynyl]-4'H-spiro[indene-1,5'-isoxazol]-3(2H)-one
3'-[(3-Chlorophenyl)ethynyl]-N-methoxy-4'H-spiro[indene-1,5'-[1,2]oxazol]-3(2H)-imine 10-[(3-Chlorophenyl)ethynyl]-1,8-dioxa-9-azadispiro[3.2.4.2]tridec-9-ene (isomer 1)
10-[(3-Chlorophenyl)ethynyl]-1,8-dioxa-9-azadispiro[3.2.4.2]tridec-9-ene (isomer 2)
3-[(3-Chlorophenyl)ethynyl]-1,9,13-trioxa-2-azadispiro[4.2.5.2]pentadec-2-ene
3'-[(6-Methylpyridin-2-yl)ethynyl]-2,3-dihydro-4'H-spiro[indene-1,5'-[1,2]oxazol]-3-ol
3-[(3-Chlorophenyl)ethynyl]-1-oxa-2-azadispiro[4.2.4.2]tetradec-2-ene
3-[(3-Chlorophenyl)ethynyl]-8,8-difluoro-1-oxa-2-azaspiro[4.5]dec-2-ene
3-[(3-Methylphenyl)ethynyl]-1-oxa-2-azadispiro[4.2.4.2]tetradec-2-ene
3-[(6-Methoxypyridin-3-yl)ethynyl]-1,9,12-trioxa-2-azadispiro[4.2.4.2]tetradec-2-ene
3'-[(6-Methylpyridin-2-yl)ethynyl]-4'H-spiro[indene-1,5'-[1,2]oxazol]-3(2H)-one
N-Methoxy-3'-[(6-methylpyridin-2-yl)ethynyl]-4'H-spiro[indene-1,5'-[1,2]oxazol]-3(2H)-imine
3-[(3-Chlorophenyl)ethynyl]-N,N-dimethyl-1-oxa-2,7-diazaspiro[4.4]non-2-ene-7-carboxamide
3-[(3-Chlorophenyl)ethynyl]-1-oxa-2,7-diazaspiro[4.4]non-2-ene-7-carboxamide
9-[(3-Chlorophenyl)ethynyl]-7-oxa-8-azadispiro[3.1.4.1]undec-8-ene
3-[(3-Methylphenyl)ethynyl]-1,9,13-trioxa-2-azadispiro[4.2.5.2]pentadec-2-ene
7-[(3-Chlorophenyl)ethynyl]-5-oxa-6-azaspiro[3.4]oct-6-ene
10-[(3-Chlorophenyl)ethynyl]-2,8-dioxa-9-azadispiro[3.2.4.2]tridec-9-ene
3-[(4-Chloropyridin-2-yl)ethynyl]-8,8-difluoro-1-oxa-2-azaspiro[4.5]dec-2-ene
Ethyl 3-[(6-methylpyridin-2-yl)ethynyl]-1-oxa-2-azaspiro[4.5]dec-2-ene-8-carboxylate
3'-[(3-Chlorophenyl)ethynyl]-1H,4'H-spiro[isochromene-4,5'-[1,2]oxazole]
{3-[(3-Chlorophenyl)ethynyl]-1-oxa-2,7-diazaspiro[4.4]non-2-en-7-yl}(4-methylpiperazin-1-yl)methanone
1-({3-[(3-Chlorophenyl)ethynyl]-1-oxa-2,7-diazaspiro[4.4]non-2-en-7-yl}carbonyl)imidazolidin-2-one
[7-[2-(3-Chlorophenyl)ethynyl]-9-oxa-3,8-diazaspiro[4.4]non-7-en-3-yl]-pyrrolidin-1-yl-methanone
[7-[2-(3-Chlorophenyl)ethynyl]-9-oxa-3,8-diazaspiro[4.4]non-7-en-3-yl]-(1-piperidyl)methanone
1-[7-[2-(3-Chlorophenyl)ethynyl]-9-oxa-3,8-diazaspiro[4.4]non-7-ene-3-carbonyl]-3-methylsulfonyl-imidazolidin-2-one
3-[(3-Chlorophenyl)ethynyl]-N-ethyl-N-(propan-2-yl)-1-oxa-2,7-diazaspiro[4.4]non-2-ene-7-carboxamide
7-[2-(3-Chlorophenyl)ethynyl]-N-methoxy-N-methyl-9-oxa-3,8-diazaspiro[4.4]non-7-ene-3-carboxamide
7-[2-(3-Chlorophenyl)ethynyl]-N-(4-pyridyl)-9-oxa-3,8-diazaspiro[4.4]non-7-ene-3-carboxamide
Ethyl 3-[(3-chlorophenyl)ethynyl]-1-oxa-2,7-diazaspiro[4.4]non-2-ene-7-carboxylate
8,8-Difluoro-2-[2-(6-methyl-2-pyridyl)ethynyl]-4-oxa-3-azaspiro[4.5]dec-2-ene
6-[2-(3-Chlorophenyl)ethynyl]-2,8-dioxa-7-azaspiro[3.4]oct-6-ene
2-[2-(3-Chlorophenyl)ethynyl]-4-oxa-3-azaspiro[4.5]dec-2-ene
2-[2-(3-Chlorophenyl)ethynyl]-8-(difluoromethylene)-4-oxa-3-azaspiro[4.5]dec-2-ene
2-[2-(3-Chlorophenyl)ethynyl]-4-oxa-3,8-diazaspiro[4.5]dec-2-ene-8-carboxamide
[2-[2-(3-Chlorophenyl)ethynyl]-4-oxa-3,8-diazaspiro[4.5]dec-2-en-8-yl]-(2-furyl)methanone
2-[2-(3-Chlorophenyl)ethynyl]-N-methoxy-N-methyl-4-oxa-3,8-diazaspiro[4.5]dec-2-ene-8-carboxamide
2-[2-(3-Chlorophenyl)ethynyl]-N,N-diethyl-4-oxa-3,8-diazaspiro[4.5]dec-2-ene-8-carboxamide
(3-Chlorophenyl)-[2-[2-(3-chlorophenyl)ethynyl]-4-oxa-3,8-diazaspiro[4.5]dec-2-en-8-yl]methanone
Ethyl 2-[2-(3-chlorophenyl)ethynyl]-4-oxa-3,8-diazaspiro[4.5]dec-2-ene-8-carboxylate
[2-[2-(3-Chlorophenyl)ethynyl]-4-oxa-3,8-diazaspiro[4.5]dec-2-en-8-yl]-pyrrolidin-1-yl-methanone
2-[2-(3-Chlorophenyl)ethynyl]-N,N-dimethyl-4-oxa-3,8-diazaspiro[4.5]dec-2-ene-8-carboxamide.

\* \* \* \* \*